(12) United States Patent
Jeong et al.

(10) Patent No.: US 9,931,400 B2
(45) Date of Patent: Apr. 3, 2018

(54) METHOD OF COMBINATION THERAPY FOR PREVENTION OR TREATMENT OF C-MET OR ANGIOGENESIS FACTOR INDUCED DISEASES

(71) Applicant: Samsung Electronics Co., Ltd., Suwon-si, Gyeonggi-do (KR)

(72) Inventors: Yun Ju Jeong, Anyang-si (KR); Kyung Ah Kim, Seongnam-si (KR); Yun Jeong Song, Seongnam-si (KR); Ji Min Lee, Seoul (KR); Hyo Seon Lee, Hwaseong-si (KR); Jae Hyun Choi, Seongnam-si (KR); Saet Byoul Lee, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1122 days.

(21) Appl. No.: 14/025,403

(22) Filed: Sep. 12, 2013

(65) Prior Publication Data

US 2014/0086926 A1 Mar. 27, 2014

(30) Foreign Application Priority Data

Sep. 12, 2012 (KR) .................. 10-2012-0101177
Sep. 11, 2013 (KR) .................. 10-2013-0108913

(51) Int. Cl.
*A61K 39/395* (2006.01)
*A61K 45/06* (2006.01)
*C07K 16/28* (2006.01)

(52) U.S. Cl.
CPC .......... *A61K 39/3955* (2013.01); *A61K 45/06* (2013.01); *C07K 16/2863* (2013.01); *C07K 2317/24* (2013.01)

(58) Field of Classification Search
None
See application file for complete search history.

(56) References Cited

U.S. PATENT DOCUMENTS

| | | |
|---|---|---|
| 6,300,065 B1 | 10/2001 | Kieke et al. |
| 6,699,658 B1 | 3/2004 | Wittrup et al. |
| 7,615,529 B2 | 11/2009 | Kong-Beltran et al. |
| 7,632,926 B2 | 12/2009 | Kim et al. |
| 7,687,063 B2 | 3/2010 | Kim et al. |
| 8,066,994 B2 | 11/2011 | Gillies et al. |
| 8,217,148 B2 | 7/2012 | Davies et al. |
| 8,398,974 B2 | 3/2013 | Davies et al. |
| 2006/0270594 A1 | 11/2006 | Kong-Beltran et al. |
| 2010/0028337 A1 | 2/2010 | Kong-Beltran et al. |
| 2010/0226925 A1 | 9/2010 | Dillon et al. |
| 2010/0278815 A1 | 11/2010 | Kim et al. |
| 2011/0064653 A1 | 3/2011 | Hansen et al. |
| 2011/0097262 A1 | 4/2011 | Goetsch et al. |
| 2011/0104161 A1 | 5/2011 | Burgess et al. |
| 2011/0104176 A1 | 5/2011 | Cheong et al. |
| 2011/0239316 A1 | 9/2011 | Goetsch et al. |
| 2011/0262436 A1 | 10/2011 | Bender et al. |
| 2011/0262439 A1 | 10/2011 | Kufer et al. |
| 2011/0263830 A1 | 10/2011 | Goetsch et al. |
| 2012/0034228 A1 | 2/2012 | Kufer et al. |
| 2012/0064066 A1 | 3/2012 | Kim et al. |
| 2012/0263723 A1 | 10/2012 | Davies et al. |
| 2013/0089556 A1 | 4/2013 | Cheong et al. |
| 2013/0089557 A1 | 4/2013 | Cheong et al. |
| 2013/0109839 A1 | 5/2013 | Goetsch et al. |
| 2013/0109840 A1 | 5/2013 | Goetsch et al. |
| 2013/0109841 A1 | 5/2013 | Goetsch et al. |
| 2013/0109844 A1 | 5/2013 | Goetsch et al. |
| 2013/0164281 A1 | 6/2013 | Cheong et al. |

FOREIGN PATENT DOCUMENTS

| | | |
|---|---|---|
| EP | 2316484 A1 | 5/2011 |
| KR | 1020070012711 A | 1/2007 |
| KR | 1020080000613 A | 1/2008 |
| KR | 1020110047698 A | 5/2011 |
| KR | 1020110066960 A | 6/2011 |
| KR | 1020110069092 A | 6/2011 |
| KR | 1020110074612 A | 6/2011 |
| KR | 1020110091519 A | 8/2011 |
| KR | 1020110097839 A | 8/2011 |
| KR | 1020130036992 A | 4/2013 |
| KR | 1020130036993 A | 4/2013 |
| KR | 2013-0079219 A1 | 7/2013 |
| WO | WO 2007/115049 A2 | 10/2007 |
| WO | WO 2009/140549 A1 | 11/2009 |
| WO | WO 2010/037837 A2 | 4/2010 |
| WO | WO 2010/045344 A1 | 4/2010 |
| WO | WO 2010/059654 A1 | 5/2010 |
| WO | WO 2010/063746 A1 | 6/2010 |
| WO | WO 2010/064090 A1 | 6/2010 |

(Continued)

OTHER PUBLICATIONS

US 6,331,391, 12/2001, Wittrup et al. (withdrawn)
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Lamminmaki et al. (JBC 2001, 276:36687-36694).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Jiao et al., "Construction of Human Naïve Fab Library and Characterization of Anti-Met Fab Fragment Generated From the Library", *Molecular Biotechnology*, 31(1): 41-54 (2005).
Sennino et al., "Suppression of Tumor Invasion and Methstasis by Concurrent Inhibition of c-Met and VEGF Signaling in Pancreatic Neuroendocrine Tumors", *Cancer Discovery*, 2(3): 270-287 (2012).

(Continued)

*Primary Examiner* — Sharon X Wen
(74) *Attorney, Agent, or Firm* — Leydig, Voit & Mayer, Ltd.

(57) ABSTRACT

Provided is a method of combination therapy for prevention or treatment of c-Met-induced or angiogenesis factor-induced diseases including co-administering an angiogenesis inhibitor and an anti-c-Met antibody or an antigen-binding fragment thereof to a patient.

10 Claims, 9 Drawing Sheets

(56) References Cited

FOREIGN PATENT DOCUMENTS

| WO | WO 2010/069765 A1 | 6/2010 |
|---|---|---|
| WO | WO 2011/143665 A1 | 11/2011 |
| WO | WO 2012/059562 A1 | 5/2012 |
| WO | WO 2013/051878 A2 | 4/2013 |
| WO | WO 2013/051891 A1 | 4/2013 |

OTHER PUBLICATIONS

You et al., "The hepatocyte growth factor/c-Met signaling pathway as a therapeutic target to inhibit angiogenesis", *BMB Reports, Korean Society for Biochemistry and Molecular Biology*, KR, 41(12): 833-839 (2008).

You et al., "VEGF and c-Met Blockade Amplify Angiogenesis Inhibition in Pancreatic Islet Cancer", *Cancer Research*, 71(14); 4758-4768 (2011).

European Search Report, European Application No. 13184072.0, dated Nov. 5, 2013.

Barderas et al., "Affinity maturation of antibodies assisted by in silico modeling," *Proceedings of the National Academy of Sciences 150*(26): 9029-9034 (Jul. 1, 2008).

Fermér et al., "Specificity Rescue and Affinity Maturation of a Low-Affinity IgM Antibody against Pro-Gastrin-Releaseing Peptide using Phage Display and DNA Shuffling," *Tumor Biology 25*(1-2): 7-13 (2004).

Yau et al., "Affinity maturation of a $V_H H$ by mutational hotspot randomization," *Journal of Immunological Methods 297*(1-2): 213-224 (2005).

\* cited by examiner

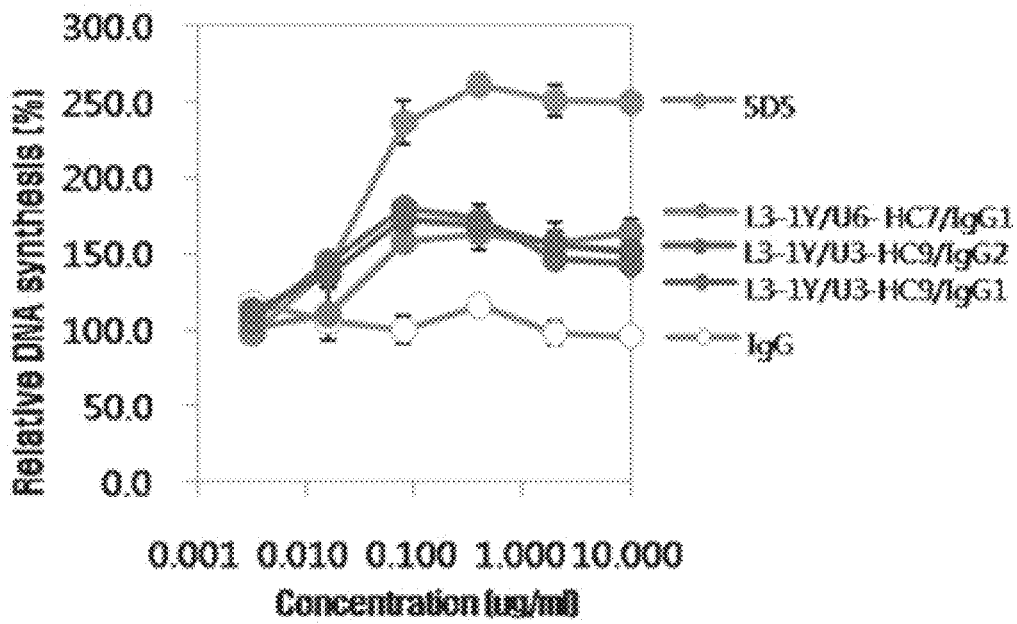
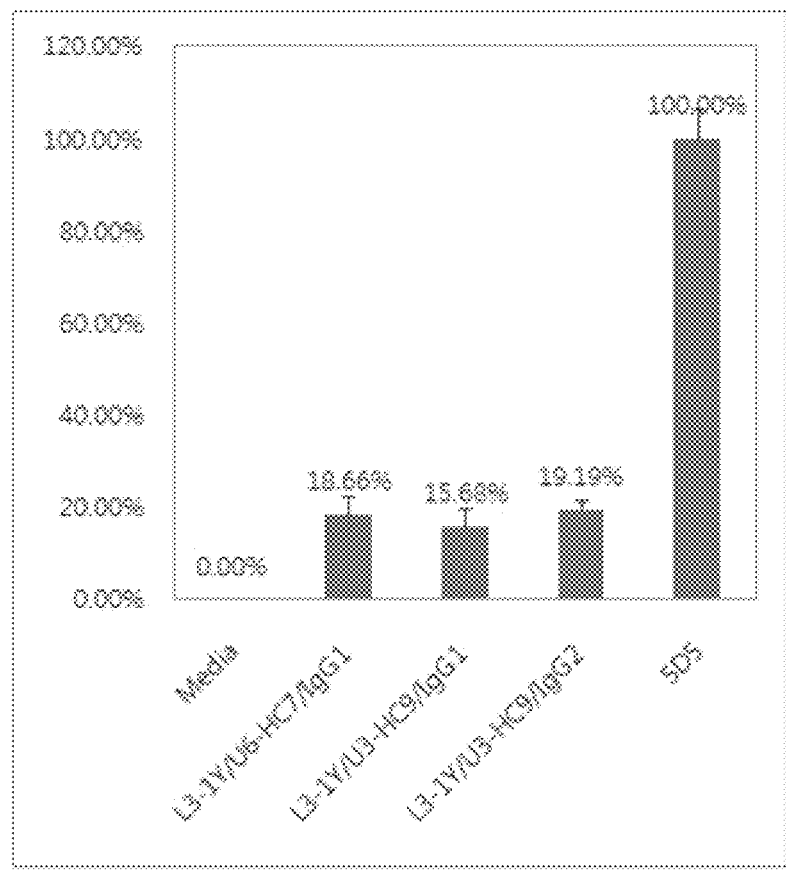

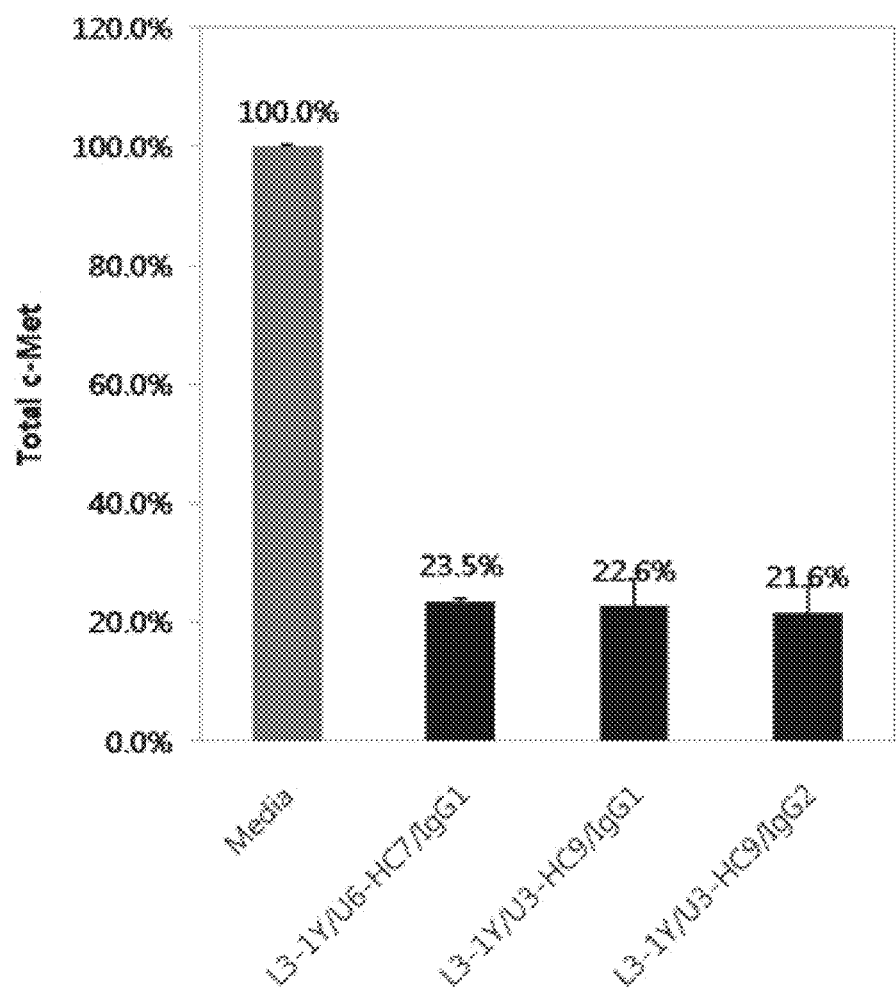

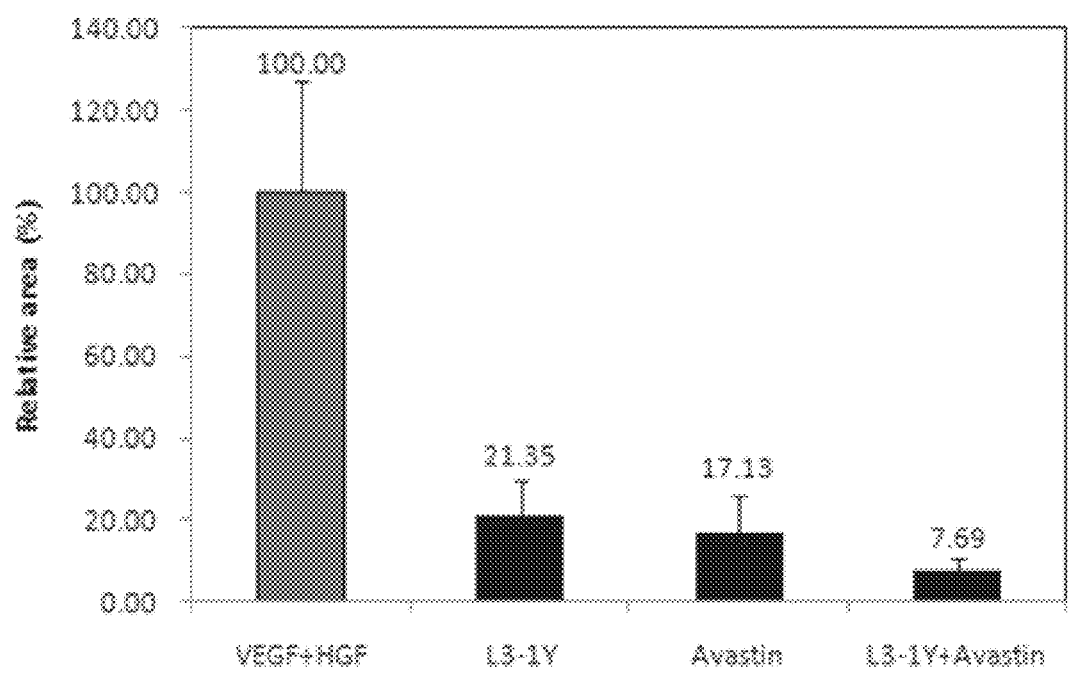

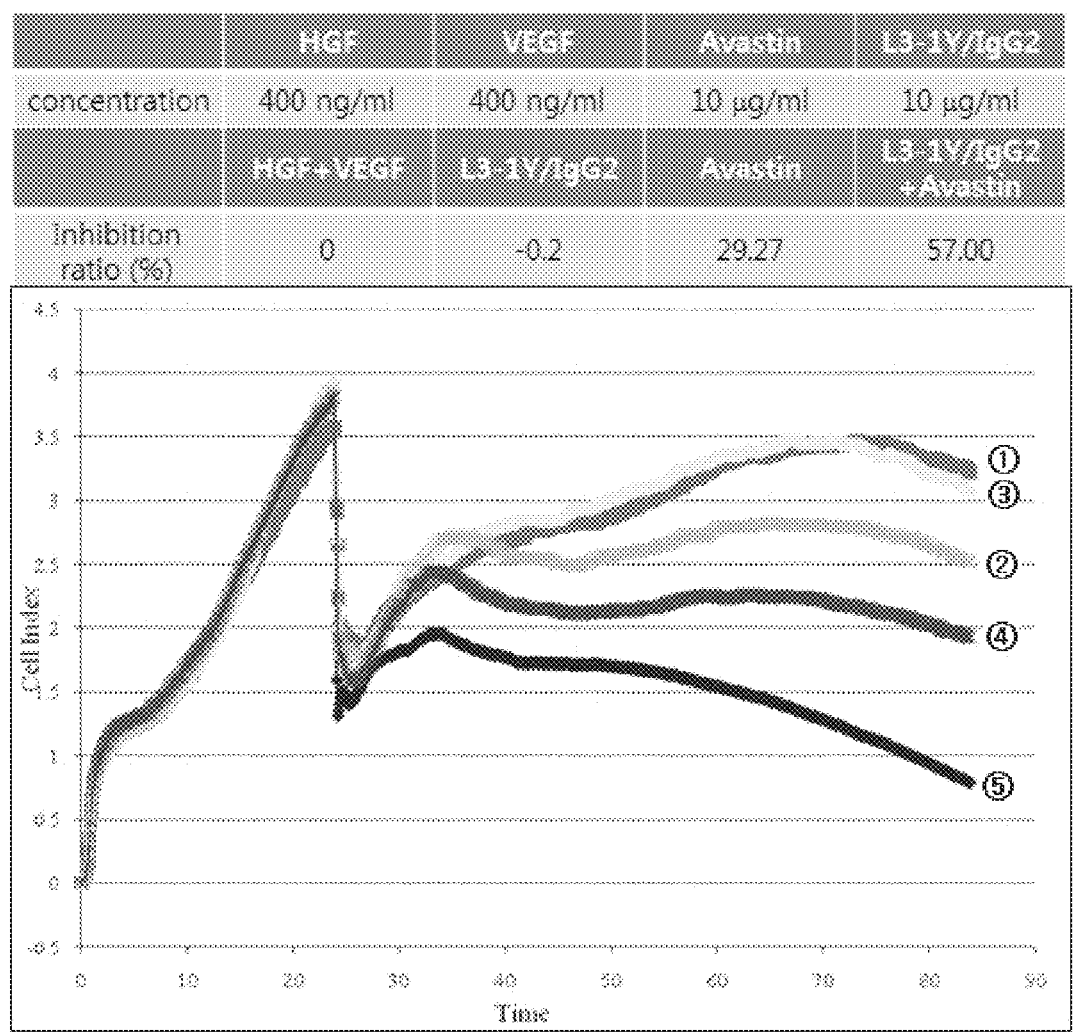

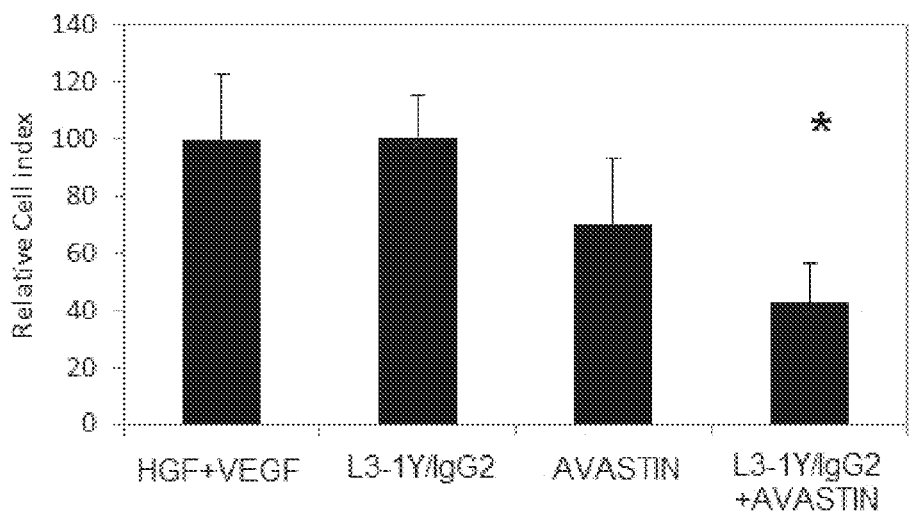

VH : the amino acid sequence from the 18th to 468th positions of SEQ ID NO: 66

```
                10         20         30         40      5052abc      60
huAbF46    EVQLVESGGGLVQPGGSLRLSCAASGFTFTDYYMSWVRQAPGKGLEWLGFIRNKANGYTTEYS
-H4-A1
                70      8082abc       90               110113
huAbF46    ASVKGRFTISRDNSKNTLYLQMNSLRAEDTAVYYCARDNWFAYWGQGTLVTVSS
-H4-A1
```

VL: the amino acid sequence from the 21st to 240th positions of SEQ ID NO: 68

```
                10         20      27abcdef 30         40         50
huAbF46    DIQMTQSPSSLSASVGDRVTITCRSSQSLLASGNQKNYLAWYQQKPGKAPKMLIIWASTR
-H4-A1
                60         70         80        90  95  100       107
huAbF46    VSGVPSRFSGSGSGTDFTLTISSLQPEDFATYYCQQSYSRPRTFGQGTKVEIK
-H4-A1
```

CDRs are underlined

METHOD OF COMBINATION THERAPY FOR PREVENTION OR TREATMENT OF C-MET OR ANGIOGENESIS FACTOR INDUCED DISEASES

CROSS-REFERENCE TO RELATED APPLICATIONS

This application claims the benefit of Korean Patent Application No. 10-2012-0101177 filed on Sep. 12, 2012, and Korean Patent Application No. 10-2013-0108913 filed on Sep. 11, 2013, in the Korean Intellectual Property Office, the disclosures of which are herein incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 272,815 Byte ASCII (Text) file named "713595 ST25 Revised.TXT" created on Aug. 8, 2016.

BACKGROUND

1. Field

A method of combination therapy for prevention and/or treatment of c-Met and/or angiogenesis factor induced diseases including co-administering an angiogenesis inhibitor and an anti-c-Met antibody or an antigen-binding fragment thereof to a patient in need thereof is provided.

2. Description of the Related Art c-Met, a typical receptor tyrosine kinase (RTK) present at the surface of cells, binds to its ligand, hepatocyte growth factor (HGF) to promote intracellular signal transduction thereby not only promoting the growth of cells but also being over-expressed in cancer cells so that it is widely implicated in cancer incidence, cancer metastasis, cancer cell migration, cancer cell penetration, angiogenesis, etc. c-Met is over-expressed in many kinds of cancers and in particular, most of the patients with over-expressed c-Met tend to have poor prognosis.

Angiogenesis inhibitors refer to any drugs designed to suppress the growth of cancer by blocking blood supply into cancer cells, and typical examples thereof may include a vascular endothelial cell growth factor (VEGF) antagonist (inhibitor). The vascular endothelial cell growth factor (VEGF) is also present in normal cells and in particular, it is secreted from cancer cells and binds to its receptor, VEGFR to induce angiogenesis, through which the cancer cells are provided with nutrients necessary for their growth.

Therefore, both of c-Met and VEGF related to angiogenesis are of great importance as a target in developing anticancer drugs.

Up to now, however, there haven't been suggested any technologies of treating cancer by concurrently administering a medicine having c-Met as its target and a medicine having angiogenesis factors (e.g., VEGF) as its target.

SUMMARY

Applicants have discovered that the combined therapy of a medicine targeting c-Met and an angiogenesis inhibitor (e.g., a medicine targeting VEGF) could achieve significant synergy effects. In particular, cancer treatment technologies having synergic anticancer effects and good prognosis were identified.

Accordingly, the invention provides a method of combined therapy for prevention and/or treatment of c-Met- and/or angiogenesis factor-induced diseases comprising co-administering a pharmaceutically effective amount of an angiogenesis inhibitor (e.g., VEGF antagonist) and a pharmaceutically effective amount of anti-c-Met antibody or an antigen-binding fragment thereof to a subject in need of prevention and/or treatment of c-Met- and/or angiogenesis factor-induced diseases. In a particular embodiment, the anti-c-Met antibody or antigen-binding fragment thereof specifically binds to an epitope comprising 5 or more amino acids (e.g., consecutive amino acids) within the SEMA domain of c-Met protein (e.g., SEQ ID NO: 79).

One embodiment provides a pharmaceutical composition for the use in a combined therapy for prevention and/or treatment of c-Met- and/or angiogenesis factor-induced diseases, containing an angiogenesis inhibitor (e.g., VEGF antagonist) and an anti-c-Met antibody or an antigen-binding fragment thereof as active ingredients.

Another embodiment provides a kit for prevention and/or treatment of c-Met- and/or angiogenesis factor-induced diseases, comprising a first pharmaceutical composition containing a pharmaceutically effective amount of an angiogenesis inhibitor (e.g., VEGF antagonist) as an active ingredient, a second pharmaceutical composition containing a pharmaceutically effective amount of anti-c-Met antibody or an antigen-binding fragment thereof as an active ingredient, and a package container.

Another embodiment provides a pharmaceutical composition or a kit containing an angiogenesis inhibitor (e.g., VEGF antagonist) and an anti-c-Met antibody or an antigen-binding fragment thereof as active ingredients.

BRIEF DESCRIPTION OF THE DRAWINGS

FIG. 1 is a graph showing the results of a BrdU assay after NCI-H441 lung cancer cell lines were treated with anti-c-Met antibodies. Agonism levels of the anti-c-Met antibodies are demonstrated. Relative DNA synthesis (%) is indicated on the y-axis, and concentration (μg/mL) is indicated on the x-axis.

FIG. 2 is a graph showing ELISA measurement results with regard to the levels of phosphorylation of Atk after Caki-1 cell lines were treated with anti-c-Met antibodies. 5D5 (American Type Culture Collection (ATCC, Manassas, Va.), a previously developed c-Met antibody, was used as a positive control (assigned 100% value, all other values are relative to 5D5).

FIG. 3 is a graph showing ELISA measurement results with regard to the total amounts of c-Met remaining after the treatment of anti-c-Met antibodies to MKN45 cell lines. Degradation levels of c-Met are shown. Total c-Met relative to the media control (assigned 100% value) is indicated on the y-axis.

FIG. 11 is a graph showing the penetration areas of HUVEC cells according to treatment drugs. Relative area (%) is indicated on the y-axis for the particular therapy (x-axis).

FIG. 12 is a graph showing real time cell analysis results with regard to a cell growth level when L3-1Y/IgG2 and avastin were co-administered (①: treated with VEGF+HGF, ②: treated with avastin alone with VEGF+HGF, ③: treated with antibody L3-1Y/IgG2 alone with VEGF+HGF, ④: co-treated with antibody L3-1Y/IgG2 and avastin with VEGF+HGF, ⑤: no treatments (media only)). Cell index is indicated on the y-axis, and time (hours) is indicated on the x-axis.

FIG. 13 is a graph showing the relative cell index (%) after administration of L3-1Y/IgG2, avastin, or both L3-1Y/IgG2 and avastin (with 71 hours, 54 minutes, and 17 seconds as an end point in the real time cell analysis).

FIG. 14 depicts amino acid sequences of select portions of the $V_H$ and $V_L$ regions of an anti-c-Met antibody (L3-1Y/IgG2) according to an embodiment. The first amino acid sequence corresponds to positions 18-134 of SEQ ID NO: 66, and the second amino acid sequence corresponds to positions 21-133 of SEQ ID NO: 68. The complementarity determining regions (CDRs) of each of the amino acid sequences are underlined.

DETAILED DESCRIPTION

Figure 4:
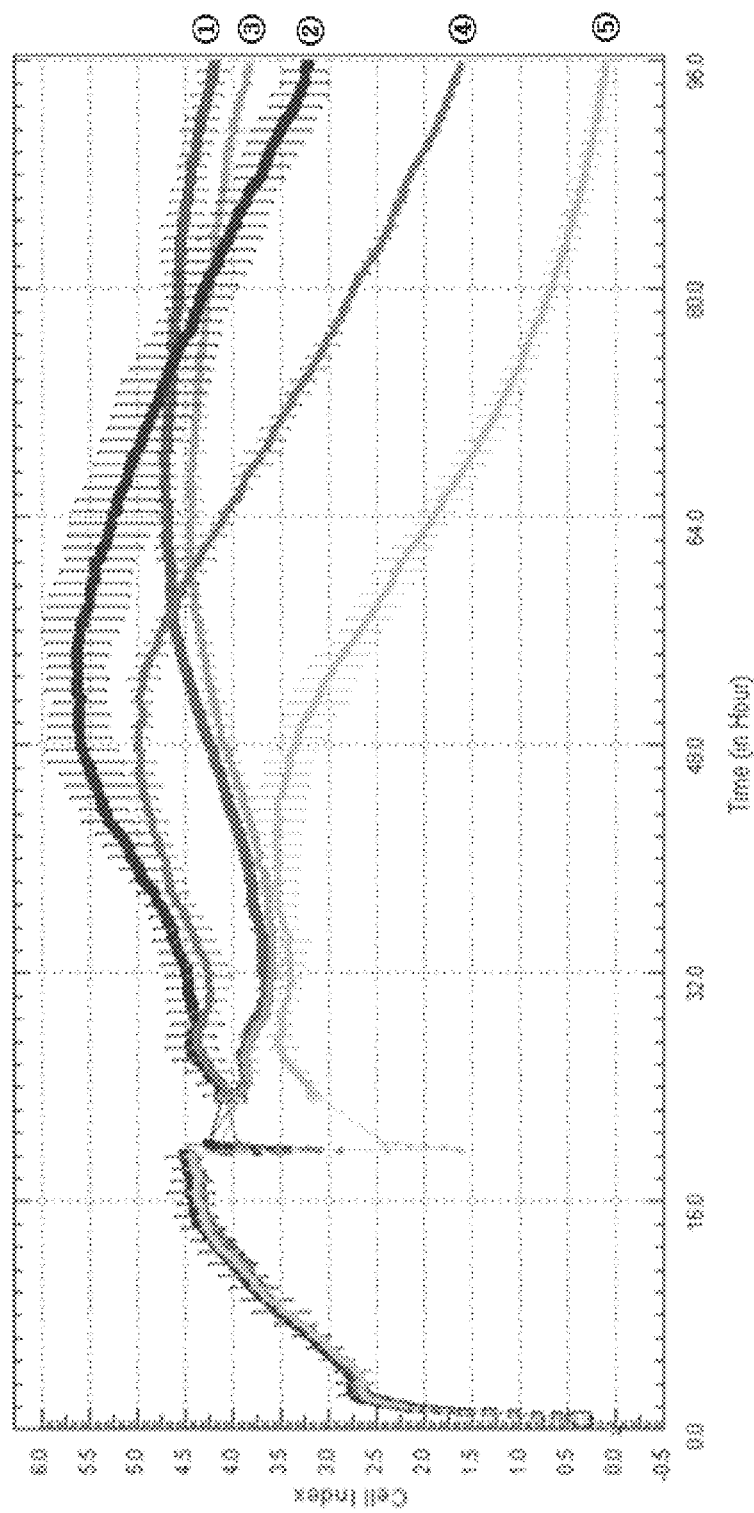
FIG. 4 is a graph showing real time cell analysis results with regard to a cell growth level when L3-1Y and avastin were co-administered (①: treated with VEGF+HGF, ②: treated with avastin alone with VEGF+HGF, ③: treated with antibody L3-1Y alone with VEGF+HGF, ④: co-treated with antibody L3-1Y and avastin with VEGF+HGF, ⑤: no treatments (media only)). Cell index is indicated on the y-axis, and time (hours) is indicated on the x-axis.

Applicants have discovered that targeting both of the c-Met and angiogenesis factors (e.g., VEGF) could efficiently inhibit the growth of cancer cells, resulting in the development of anticancer drugs having improved effects. Therefore, in this invention, the growth of cancer cells itself is inhibited by targeting c-Met, and, at the same time, angiogenesis is suppressed by targeting VEGF, thereby blocking the supply of nutrients necessary for the growth of the cancer cells so that the growth of the cancer cells is inhibited. Thus, in inhibiting the growth of cancer cells, a considerable synergistic effect can be obtained by targeting both of the factors. Furthermore, since angiogenesis is an essential element of primary metastatic cancers by providing a new passage so that cancer cells travel near or far distance, the suppression of VEGF may result in desirable effects in suppressing the metastasis of cancer by blocking VEGF/VEGFR signal systems, thereby suppressing angiogenesis.

Accordingly, the concurrent targeting of the two factors of c-Met and angiogenesis factor (e.g., VEGF) enables the inhibition of the growth of cancer tissues and, at the same time, the inhibition of cancer growth and metastasis due to angiogenesis.

Thus, in one embodiment, there is provided a pharmaceutical composition for combined therapy (co-administration) for prevention and/or treatment of c-Met- and angiogenesis factor-induced diseases containing an angiogenesis inhibitor and an anti-c-Met antibody or an antigen-binding fragment thereof as active ingredients. In another embodiment, there is provided a pharmaceutical composition containing an angiogenesis inhibitor and an anti-c-Met antibody or an antigen-binding fragment thereof as active ingredients.

In one particular embodiment, the pharmaceutical composition for combined therapy may be formulated by mixing a pharmaceutically effective amount of an angiogenesis inhibitor and a pharmaceutically effective amount of an anti-c-Met antibody or an antigen-binding fragment thereof to be simultaneously administered as a combined mixture.

In another particular embodiment, the pharmaceutical composition for combined therapy may be one where a pharmaceutically effective amount of an angiogenesis inhibitor and a pharmaceutically effective amount of an anti-c-Met antibody or an antigen-binding fragment thereof are formulated, respectively, and they are administered simultaneously or sequentially. The pharmaceutical composition for combined therapy may be a pharmaceutical composition for pharmaceutical combined therapy for simultaneous or sequential administration comprising a first pharmaceutical composition containing a pharmaceutically effective amount of an angiogenesis inhibitor as an active ingredient and a second pharmaceutical composition containing a pharmaceutically effective amount of an anti-c-Met antibody or an antigen-binding fragment thereof as an active ingredient. For sequential administration, the sequence of administration (which active ingredient is administered first or second) does not matter.

In another embodiment, a kit for prevention and/or treatment of c-Met and angiogenesis-induced diseases is provided, wherein the kit comprises (a) a first pharmaceutical composition containing a pharmaceutically effective amount of an angiogenesis inhibitor as an active ingredient, (b) a second pharmaceutical composition containing a pharmaceutically effective amount of an anti-c-Met antibody or an antigen-binding fragment thereof as an active ingredient, and (c) a package container. In another embodiment, a kit includes (a) a first pharmaceutical composition containing a pharmaceutically effective amount of an angiogenesis inhibitor as an active ingredient, (b) a second pharmaceutical composition containing a pharmaceutically effective amount of an anti-c-Met antibody or an antigen-binding fragment thereof as an active ingredient, and (c) a package container.

The combined therapy of an angiogenesis inhibitor, for example, a drug having VEGF as its target (VEGF antagonist), and an anti-c-Met antibody or an antigen-binding fragment thereof can achieve excellent synergy effects when compared to using a single drug alone.

Moreover, the combined therapy of an angiogenesis inhibitor, for example, a drug having VEGF as its target (VEGF antagonist) and an anti-c-Met antibody or an antigen-binding fragment thereof may achieve excellent effects even in patients with resistance against angiogenesis inhibitors (e.g., VEGF antagonists). Accordingly, in another embodiment, there is provided a pharmaceutical composition for combined therapy for overcoming resistance against angiogenesis inhibitors (e.g., VEGF antagonists) containing an angiogenesis inhibitor (e.g., VEGF antagonist) and an anti-c-Met antibody or an antigen-binding fragment thereof as active ingredients.

The anti-c-Met antibodies or antigen-binding fragments thereof are not dependent upon Cbl, which is a typical RTK negative regulator, and exhibit c-Met degradation activity via a lysosome pathway and not via a proteasome pathway, which is mediated by Cbl. Thus, even if the anti-c-Met antibodies or antigen-binding fragments thereof are administered to patients where Cbl does not normally function due to such factors such as a mutation in Cbl, low expression levels of Cbl, or mutation of the Cbl binding site of c-Met, c-Met can be suppressed through LRIG1 as a mediator, which is another negative regulator that functions independently from Cbl. Accordingly, the combined therapy of a VEGF antagonist and an anti-c-Met antibody or an antigen-binding fragment thereof may be particularly advantageous to the patients where Cbl does not function normally.

The "angiogenesis inhibitors" as used herein refer to all the substances known for inhibiting angiogenesis. Typical examples include, but are not limited to, drugs (VEGF antagonists) that suppress the function of vascular endothelial cell growth factor (VEGF) as their target.

Vascular endothelial cell growth factor (VEGF) is present in normal cells and, particularly, is secreted from cancer cells and binds to its receptor (VEGFR) to induce angiogenesis. Cancer cells are supplied with nutrients necessary for their growth through newly induced blood vessels. The over-expression of VEGF causes various diseases and is involved with not only cancer incidence but also its bad prognosis such as invasion, metastasis, and so on. For such reasons, VEGF has become a key target in anticancer therapy.

VEGF may be selected from the group consisting of VEGFs from mammals including primates such as humans and monkeys, and rodents such as mice and rats. For example, VEGF proteins may be polypeptides encoded by nucleotide sequences (mRNA) provided by GenBank Accession Number Nos. NM_001025366.2 (SEQ ID NO: 109), NM_001025367.2 (SEQ ID NO: 110), NM_001025368.2 (SEQ ID NO: 111), NM_001025369.2 (SEQ ID NO: 112), NM_001025370.2 (SEQ ID NO: 113), NM_001033756.2 (SEQ ID NO: 114), NM_001171622.1 (SEQ ID NO: 115), NM_001171623.1 (SEQ ID NO: 116), NM_001171624.1 (SEQ ID NO: 117), NM_001171625.1 (SEQ ID NO: 118), NM_001171626.1 (SEQ ID NO: 119), NM_001171627.1 (SEQ ID NO: 120), NM_001171628.1 (SEQ ID NO: 121), NM_001171629.1 (SEQ ID NO: 122), NM_001171630.1 (SEQ ID NO: 123), NM 001204384.1 (SEQ ID NO: 124), NM_001204385.1 (SEQ ID NO: 125), or NM_003376.5 (SEQ ID NO: 126).

The drugs having VEGF as their target (VEGF antagonists) include, but are not limited to, VEGF antibodies and small molecule drugs. In particular, the drugs may be at least one selected from the group consisting of avastin, VEGF-trap, sunitinib (Sugen and Pfizer; SU-11248, SU-011248, SU-11248J, SUTENT®), sunitinib malate, AEE-788 (Novartis; AE-788 or NVP-AEE-788), axitinib (Pfizer; AG-13736 or AG-013736), AG-028262 (Pfizer), combretastatin A4 analog (AVE-8062; Ajinomoto Co. and Sanofi-aventis; AC-7700), cediranib (AZD-2171; AstraZeneca; AZ-2171), BMS-387032 (Sunesis and Bristol-Myers Squibb; SNS-032 or CAS Registry Number 345627-80-7), CEP-7055 (Cephalon and Sanofi-aventis; CEP-11981 or SSR-106462), CHIR-258 (Chiron; CAS Registry Number 405169-16-6, GFKI, or GFKI-258), CP-547632 (OSI Pharmaceuticals and Pfizer; CAS Registry Number 252003-65-9) or its pseudo inhibitors CP-564959, E-7080 (Eisai Co.; CAS Registry Number 417716-92-8, ER-203492-00), Pazopanib (GlaxoSmithKline), GW-654652 (GlaxoSmithKline) or its associated indazolylpyrimidine Kdr inhibitors, KRN-951 (Kirin Brewery Co.) or its associated quinoline-urea VEGF inhibitors, midostaurin (PKC-412; Novartis; CAS Registry Number 120685-11-2, benzoylstaurosporine, CGP-41251, STI-412), vatalanib (PTK-787; Novartis and Schering; CAS Registry Numbers 212141-54-3 and 212142-18-2; PTK/ZK, PTK-787/ZK-222584, ZK-22584, VEGF-TKI, VEGF-RKI, PTK-787A, DE-00268, CGP-79787, CGP-79787D, ZK-222584) or its associated anilinophthalazine derivative VEGF inhibitors, semaxanib (SU-5416; Sugen and Pfizer/Pharmacia; CAS Registry Number 194413-58-6, 204005-46-9), SU-6668 (Sugen and Taiho; CAS Registry Number 252916-29-3, SU-006668, TSU-68), thalidomide (Celgene; CAS Registry Number 50-35-1, Synovir, Thalidomide Pharmion, Thalomid), XL-647 (Exelixis; EXEL-7647), XL-999 (Exelixis; EXEL-0999), vandetanib (ZD-6474 AstraZeneca; CAS Registry Number 443913-73-3, Zactima, AZD-6474) or its associated anilinoquinazoline VEGF inhibitors, ZK-304709 (Schering; CDK inhibitors (indirubin derivatives), ZK-CDK, MTGI, multi-target tumor growth inhibitor) or indirubin derivative VEGF inhibitors (see WO 00/234717, WO 02/074742, WO 02/100401, WO 00/244148, WO 02/096888, WO 03/029223, WO 02/092079, WO 02/094814), CDP791, Enzastaurin, BIBF 1120 (Boehringer Ingelheim), BAY 573952, BAY 734506, XL 184, IMC-1121B, CEP 701, SU 014813, SU 10944, SU 12662, OSI-930, BMS 582664, and so on.

In addition to the VEGF antagonists, angiogenesis inhibitors which indirectly suppress VEGF may be used. Such angiogenesis inhibitors include, but are not limited to, N-acetylcolchinol phosphate (ZD-6126; AstraZeneca and Angiogene; CAS Registry Number 219923-05-4, ANG-453, AZD-6126, ZD-6126 derivatives, ZM-445526) or ANG-400 series medications, Imatinib (Novartis; CAS Registry Numbers 152459-95-5, 220127-57-1, Glivec, STI-571, CGP-57148), everolimus (RAD-001; Novartis; CAS Registry Number 159351-69-6, RAD-001, SDZ-RAD, Certican), dasatinib (BMS-354825; Bristol-Myers Squibb; CAS Registry Number 302962-49-8, Src/Abl kinase inhibitor), and so on.

"c-Met" or "c-Met protein" refers to a receptor tyrosine kinase (RTK) which binds hepatocyte growth factor (HGF). c-Met may be derived from any species, particularly a mammal, for instance, primates such as human c-Met (e.g., NP_000236; SEQ ID NO: 127), monkey c-Met (e.g., *Macaca mulatta*, NP_001162100; SEQ ID NO: 128), or rodents such as mouse c-Met (e.g., NP_032617.2; SEQ ID NO: 129), rat c-Met (e.g., NP_113705.1; SEQ ID NO: 130), and the like. The c-Met protein may include a polypeptide encoded by the nucleotide sequence identified as GenBank Accession Number NM_000245 (SEQ ID NO: 131), a polypeptide including the amino acid sequence identified as GenBank Accession Number NP_000236 or extracellular domains thereof. The receptor tyrosine kinase c-Met participates in various mechanisms, such as cancer incidence, metastasis, migration of cancer cell, invasion of cancer cell, angiogenesis, and the like.

The antigen-binding fragment of the anti-c-Met antibody may refer to a fragment including an antigen binding region of the anti-c-Met antibody, and can be selected from the group consisting of a complementarity determining region (CDR), fragment including CDR and Fc region, scFv, (scFv)$_2$, Fab, Fab', and F(ab')$_2$ of the anti-c-Met antibody.

The anti-c-Met antibody may also include a variant of the antibody. The variant of the antibody may be any isotype of antibodies derived from human and other animals found in nature and/or one including any Fc region of antibodies derived from human and other animals, including a mutated hinge wherein at least one amino acid is changed, deleted, inserted, or added. Unless stated otherwise, the anti-c-Met antibody may include the variants of the antibody as well as the antibody with no variation.

The anti c-Met antibody may recognize a specific region of c-Met, e.g., a specific region in the SEMA domain, as an epitope. It may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may include the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti c-Met antibody provided in the present invention.

The term "epitope," as used herein, refers to an antigenic determinant, a part of an antigen recognized by an antibody. In one embodiment, the epitope may be a region comprising 5 or more contiguous (consecutive or non-consecutive) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide including 5 to 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73. The term 'contiguous amino acids' or 'contiguous amino acid residues' may refer to amino acid residues which contiguously locate on 1-, 2- or 3-dimensional structure.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti c-Met antibody may specifically bind to an epitope which includes 5 to 19 consecutive or non-consecutive amino acids selected from among partial combinations of the amino acid sequence of SEQ ID NO: 71, including SEQ ID NO: 73 as an essential element. For example, the anti c-Met antibody may specifically bind to an epitope including the amino acid sequence of SEQ ID NO: 71, SEQ ID NO: 72, or SEQ ID NO: 73.

In one embodiment, the anti c-Met antibody may be an antibody or antigen-binding fragment which includes:

a heavy chain variable region including at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5 or SEQ ID NO: 2, or including an amino acid sequence of 8 to 19 consecutive amino acids including amino acid residues 3 to 10 within the amino acid sequence of SEQ ID NO: 2; and (c) a CDR-H3 including the amino acid sequence of SEQ ID NO: 6 or SEQ ID NO: 85, or including an amino acid sequence of 6 to 13 consecutive amino acids including amino acid residues 1 to 6 within the amino acid sequence of SEQ ID NO: 85; and a light chain variable region including at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9 or SEQ ID NO: 86, or including an amino acid sequence of 9 to 17 consecutive amino acids including amino acid residues 1 to 9 within the amino acid sequence of SEQ ID NO: 89.

Herein, the amino acid sequences of SEQ ID NOS: 4 to 9 are respectively represented by following Formulas I to VI, below:

```
Formula I                         (SEQ ID NO: 4)
Xaa1-Xaa2-Tyr-Tyr-Met-Ser,
``` wherein Xaa$_1$ is absent or Pro or Ser, and Xaa$_2$ is Glu or Asp,

```
Formula II                        (SEQ ID NO: 5)
Arg-Asn-Xaa3-Xaa4-Asn-Gly-Xaa5-Thr,
``` wherein Xaa$_3$ is Asn or Lys, Xaa$_4$ is Ala or Val, and Xaa$_5$ is Asn or Thr,

```
Formula III                       (SEQ ID NO: 6)
Asp-Asn-Trp-Leu-Xaa6-Tyr,
``` wherein Xaa$_6$ is Ser or Thr,

```
Formula IV                        (SEQ ID NO: 7)
Lys-Ser-Ser-Xaa7-Ser-Leu-Leu-Ala-Xaa8-Gly-Asn-
Xaa9-Xaa10-Asn-Tyr-Leu-Ala
``` wherein Xaa$_7$ is His, Arg, Gln, or Lys, Xaa$_8$ is Ser or Trp, Xaa$_9$ is His or Gln, and Xaa$_{10}$ is Lys or Asn,

```
Formula V                         (SEQ ID NO: 8)
Trp-Xaa11-Ser-Xaa12-Arg-Val-Xaa13
``` wherein Xaa$_{11}$ is Ala or Gly, Xaa$_{12}$ is Thr or Lys, and Xaa$_{13}$ is Ser or Pro, and

```
Formula VI                        (SEQ ID NO: 9)
Xaa14-Gln-Ser-Tyr-Ser-Xaa15-Pro-Xaa16-Thr
``` wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include a heavy variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

In one embodiment, the antibody may be an antigen-binding fragment selected from the group consisting of scFv, (scFv)$_2$, Fab, Fab', and F(ab')$_2$.

The term "antigen-binding fragment" used herein refers to fragments of an intact immunoglobulin including portions of a polypeptide including antigen-binding regions having the ability to specifically bind to the antigen. For example, the antigen-binding fragment may be scFv, (scFv)$_2$, Fab, Fab', or F(ab')$_2$, but is not limited thereto. Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The antigen-binding fragments may be attainable using protease (for example, the Fab fragment may be obtained by restricted cleavage of a whole antibody with papain, and the F(ab')$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge or IgG2 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100, 101, 102, 103, or 104, or a hinge region including the amino acid sequence of SEQ ID NO: 105 (non-modified human hinge). Preferably, the hinge region includes the amino acid sequence of SEQ ID NO: 100 or 101.

In one embodiment of the anti c-Met antibody or antigen-binding fragment, the variable domain of the heavy chain includes the amino acid sequence of SEQ ID NO: 17, 74, 87, 90, 91, 92, 93, or 94 and the variable domain of the light chain includes the amino acid sequence of SEQ ID NO: 18, 19, 20, 21, 75, 88, 95, 96, 97, 98, 99, or 107.

In one embodiment, the anti c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference).

The anti c-Met antibody may include all the antibodies defined in Korean Patent Publication No. 2011-0047698.

In the anti-c-Met antibody, the portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

According to an embodiment, the anti c-Met antibody may include a heavy chain including the amino acid sequence from the $18^{th}$ to $460^{th}$ positions of SEQ ID NO: 66 and a light chain including the sequence from the $21^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In an embodiment, the anti c-Met antibody may include a heavy chain with the amino acid sequence from 18$^{th}$ to 460$^{th}$ positions of SEQ ID NO: 66 and a light chain with the amino acid sequence from 21$^{st}$ to 240$^{th}$ positions of SEQ ID NO: 68; or a heavy chain with the amino acid sequence from 18$^{th}$ to 460$^{th}$ positions of SEQ ID NO: 66 and a light chain with the amino acid sequence of SEQ ID NO: 108.

In another embodiment, the anti c-Met antibody may include a light chain complementarity determining region including the amino acid sequence of SEQ ID NO: 106, a variable domain of a light chain including the amino acid sequence of SEQ ID NO: 107, or a light chain including the amino acid sequence of SEQ ID NO: 108.

The composition comprising an antibody or an antigen-binding fragment can be formulated into immunoliposomes. Additionally, the pharmaceutical composition or the combined mixture may be formulated into immunoliposomes. Liposomes comprising an antibody may be prepared using methods that are well-known in the art. The immunoliposomes may be produced from a lipid composition comprising phosphatidylcholine, cholesterol, and PEGylated phosphatidylethanolamine by reverse-phase evaporation. In a particular example, Fab' may be conjugated to liposomes by disulfide reformation. The liposome may further contain an anticancer agent such as doxorubicin.

In one embodiment, the antibody may act as an antagonist of c-Met protein.

As used herein, the term "antagonist" is intended to encompass all molecules that at least partially block, suppress, or neutralize at least one of the biological activities of a target (e.g., c-Met). By way of example, an "antagonist" antibody means an antibody suppresses or inhibits the biological activity of the antigen to which the antibody binds (e.g., c-Met). An antagonist may function to reduce ligand-induced receptor phosphorylation or to incapacitate or kill cells which have been activated by ligands. Also, an antagonist may completely interfere with receptor-ligand interaction or substantially reduce the interaction by changing the three-dimensional structure of the receptor or by down regulation.

The combined mixture is obtained by mixing a pharmaceutically effective amount of an angiogenesis inhibitor (e.g., VEGF antagonist) and a pharmaceutically effective amount of an anti-c-Met antibody or an antigen-binding fragment thereof. Alternatively, a first pharmaceutical composition containing a pharmaceutically effective amount of an angiogenesis inhibitor (e.g., VEGF antagonist) as an active ingredient, and a second pharmaceutical composition containing a pharmaceutically effective amount of an anti-c-Met antibody or an antigen-binding fragment thereof as an active ingredient may be provided optionally together with a pharmaceutically acceptable carrier, diluent, and/or excipient.

The pharmaceutically acceptable carriers that may be included in the combined mixture or the pharmaceutical compositions may be those commonly used in formulations of drugs, and may be, but not limited to, at least one selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil. Besides these components, the combined mixture or the pharmaceutical compositions may further include at least one selected from the group consisting of a diluent, an excipient, a lubricant, a wetting agent, a sweetener, a flavor enhancer, an emulsifying agent, a suspension agent, and a preservative.

The mixture or the pharmaceutical compositions may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The term "the pharmaceutically effective amount" as used in this specification refers to an amount at which each active ingredient can exert pharmaceutically significant effects.

For one-time administration, a pharmaceutically effective amount of the angiogenesis inhibitors (e.g., VEGF antagonists) and a pharmaceutically effective amount of the anti-c-Met antibodies or antigen-binding fragments thereof may be prescribed in a variety of ways, depending on many factors including formulation methods, administration manners, ages of patients, body weight, gender, pathologic conditions, diets, administration time, administration interval, administration route, excretion speed, and reaction sensitivity. For example, the effective amount of the angiogenesis inhibitors (e.g., VEGF antagonists) may be, but not limited to, in ranges of 0.001 to 1000 mg/kg, particularly 0.01 to 100 mg/kg, more particularly 0.1 to 50 mg/kg for their one-time administration and the effective amount of the anti-c-Met antibodies or antigen-binding fragments thereof may be, but not limited to, in ranges of 0.001 to 1000 mg/kg, particularly 0.01 to 100 mg/kg, more particularly 0.1 to 50 mg/kg for their one-time administration. The effective amount for one-time administration may be formulated into a single formulation in a unit dosage form or formulated in suitably divided dosage forms, or it may be manufactured to be contained in a multiple dosage container. For the kit, the effective amount of the angiogenesis inhibitors (e.g., VEGF antagonists) and the effective amount of the anti-c-Met antibodies or antigen-binding fragments thereof for one-time administration (single dose) may be contained in a package container as a base unit.

The administration interval between the administrations is defined as a period between the first administration and the following administration. The administration interval may be, but is not limited to, 5 hours to 30 days (e.g., 10 hours, 15 hours, 20 hours, 1 day, 2 days, 3 days, 4 days, 5 days, 6, days, 7 days, 10 days, 14 days, 21 days, or 28 days) and particularly 5 to 14 days or so. For the combined therapy, the first pharmaceutical composition containing a pharmaceutically effective amount of an angiogenesis inhibitor (e.g., VEGF antagonist) as an active ingredient, and the second pharmaceutical composition containing a pharmaceutically effective amount of an anti-c-Met antibody or an antigen-binding fragment thereof as an active ingredient may be co-administered in a given time interval (e.g., several minutes, several hours or several days, or several weeks) to be determined by a type of diseases, a patient's conditions, etc. For example, the first pharmaceutical composition and the second pharmaceutical composition may be simultaneously administered (administration interval within 1 minute) or sequentially administered (administration interval of 1 minute or over), and in case of sequential administration, the administration interval between the first pharmaceutical composition and the second pharmaceutical composition may be 1 minute to 30 days, particularly, 1 minute to 7 days, 1 minute to 24 hours, or 1 minute to 60 minutes, and more particularly, 1 minute to 10 minutes, and their administration order may be reversed.

The combined mixture or the pharmaceutical compositions may be a solution in oil or an aqueous medium, a suspension, a syrup, an emulsifying solution form, or they may be formulated into a form of an extract, elixirs, powders, granules, a tablet or a capsule, and they may further include a dispersing agent or a stabilizing agent for their formulation.

In accordance with another embodiment, there is provided a method of combined therapy for prevention and/or treatment of c-Met and angiogenesis factors (e.g., VEGF) induced diseases comprising co-administering to a patient a pharmaceutically effective amount of an angiogenesis inhibitor (e.g., VEGF antagonist) and a pharmaceutically effective amount of an anti-c-Met antibody or an antigen-binding fragment thereof, to a patient in need of prevention and/or treatment of c-Met- and/or angiogenesis factor-induced diseases. The method may further comprise a step of identifying a patient who is in need of the prevention and/or treatment of c-Met- and angiogenesis factor (e.g., VEGF)-induced diseases, prior to the co-administration step.

In the method of combined therapy, the step of co-administering may conducted by simultaneously or sequentially administering a pharmaceutically effective amount of an angiogenesis inhibitor and a pharmaceutically effective amount of an anti-c-Met antibody or an antigen-binding fragment thereof. In the case of sequential administration, the order of administration of each effective ingredient is not specially restricted.

In one embodiment, the method of combined therapy may be performed by administering a mixture where a pharmaceutically effective amount of an angiogenesis inhibitor (e.g., VEGF antagonist) and a pharmaceutically effective amount of an anti-c-Met antibody or an antigen-binding fragment thereof are mixed. In another embodiment, the method of combined therapy may simultaneously or sequentially perform a first step of administration of a pharmaceutically effective amount of an angiogenesis inhibitor (e.g., VEGF antagonist) as an active ingredient, and a second step of administration of a pharmaceutically effective amount of an anti-c-Met antibody or an antigen-binding fragment thereof as an active ingredient. In the sequential manner, the administration order may be reversed.

The patients may be mammals including primates such as humans and monkeys and rodents such as mice and rats. Furthermore, the patients may be cancer patients, or patients having resistance against angiogenesis inhibitors (e.g., VEGF antagonists). Hence, the prevention and/or treatment method may further include a step of identifying a patient having resistance against angiogenesis inhibitors (e.g., VEGF antagonists), prior to the administration step.

In one embodiment, the patients may be those where existing c-Met antibody does not exhibit c-Met degradation activities because Cbl is not present or it is present at a low concentration (for example, when Cbl is subject to immunohistochemistry staining using an anti Cbl antibody available for immunohistochemistry staining, it is present at a concentration of '+1' or '−'), a functional mutation is induced, or an interaction site of c-Met with Cbl is mutated. Further, the patients may be those capable of degrading c-Met by their intrinsic c-Met antibody via an independent pathway from Cbl by a mediation of LRIG1 due to a high expression amount of LRIG1.

Therefore, the prevention and/or treatment method may further comprise a step of identifying a patient with inactivated Cbl and/or high expression amount of LRIG1.

The step of identifying the patients may include:

(1) a step of identifying a Cbl concentration in a cell specimen isolated from patients, whether Cbl is mutated or not, and/or whether an interaction site of c-Met with Cbl is mutated or not; and (2) a step of determining, in cases that the Cbl concentration falls under '+1' or '−,' when it is subject to immunohistochemistry staining using an anti Cbl antibody available for immunohistochemistry staining, a Cbl mutation is present, and/or a mutation at the interaction site of c-Met with Cbl is present, that these cells or a patient from which the cells are derived, are suitable subjects for administration of the pharmaceutical compositions for combined therapy.

In a particular embodiment, the step of identifying a patient may further include a step of identifying an LRIG1 concentration in a cell specimen isolated from patients, and, when the LRIG1 concentration falls under +2 or +3 when it is subject to immunohistochemistry staining using an anti LRIGI antibody available for immunohistochemistry staining, a step of determining that the patient is suitable for administration of the pharmaceutical compositions for combined therapy.

"Cbl," "Cbl proteins," or "Cbl enzymes" are also referred to E3 ligase, a protein involved in a cell signal transduction and protein ubiquitination. The proteins function in the degradation of c-Met proteins by internalizing them within cells. The proteins may be polypeptides encoded by nucleotide sequences deposited under GenBank Accession Numbers NM_005188, NM_007619, NM_170662, or NM_001033238, or polypeptides including amino acid sequences of GenBank Accession Numbers NP_005199, NP_031645, NP_733762, or NP_001028410.

"LRIG1" (Leucine-rich repeats and immunoglobulin-like domains protein 1) is a transmembrane protein that interacts with receptor tyrosine kinases such as EGFR-class, MET, and RET proteins. LRIG1 may be derived from mammals including primates such as humans and monkeys and rodents such as mice and rats and in particular, it may be human LRIG1 (Accession No. NM_015541 or NP_056356).

The identification of Cbl concentration or LRIG1 concentration may be carried out by measuring the concentration by common protein quantity analysis means, and/or evaluating the measured results. For example, Cbl concentration or LRIG1 concentration may be measured through common enzyme reaction, fluorescence, luminescence, and/or radiation detection using an antibody or an aptamer specifically binding to Cbl or LRIG1, respectively. In particular, the concentration may be measured by a method selected from the group consisting of immunochromatography, immunohistochemistry staining, enzyme linked immunosorbent assay (ELISA), radioimmunoassay (RIA), enzyme immunoassay (EIA), fluorescence immunoassay (FIA), luminescence immunoassay (LIA), and western blotting, but it is not limited thereto. The detection substances for the measurement of Cbl concentration or LRIG1 concentration may be at least one selected from the group consisting of an antibody, an aptamer, etc. specifically binding to Cbl or LRIG1.

The Cbl mutations may be any mutations at Cbl genes that cause a loss in functions associated with an interaction with c-Met (e.g., binding), and/or the cell internalization of c-Met and/or the degradation of c-Met, and/or any sequential or structural mutations of Cbl proteins. In a particular embodiment, the Cbl mutations may be a deletion of a successive 51 or more nucleotides (for example, 51 to 200 nucleotides) or a substitution with different nucleotides within a region from the $1169^{th}$ to $1414^{th}$ positions of nucleotide sequences deposited under GenBank Accession Number NM_005188. Alternatively, the Cbl mutations may be a deletion of a successive 17 or more amino acids (for example, a successive 17 to 100 amino acids) or a substitution with different amino acids within a region from the $343^{rd}$ to $424^{th}$ of the amino acid sequences of GenBank Accession Number NP_005179. Such mutations induce the modification of RING Finger Motif of Cbl and result in function loss as an E3 ligase enzyme. Thus, the ability to degrade other proteins vanishes due to the mutations of these nucleotides or amino acids.

Whether such Cbl mutations occur or not may be identified by direct analysis of nucleotide sequences or amino acid sequences, by measuring them via RT-PCR or DNA sequencing methods, etc., and/or by evaluating the measured results, but not limited thereto.

A substance capable of detecting Cbl mutations may be at least one selected from the group consisting of a primer capable of detecting such mutations, an anti-Cbl antibody or an aptamer specifically binding to Cbl, etc., but not limited thereto. The primers capable of detecting Cbl mutations may be successive 20 to 50 sequences containing mutated sites among the nucleotide sequences of mutated Cbl genes and/or sequences complementary thereto or sequences having 80% or more, particularly 90% or more, and more particularly 95% or more of sequence identity/homology that can hybridize therewith.

The c-Met mutations refer to mutations of c-Met occurring at a site recognized and/or bound by Cbl, and encompass mutations that prevent Cbl from interacting with c-Met (e.g., binding) although Cbl is sufficiently present in quantities or no function loss change occurs.

"The interaction site of c-Met with Cbl" is a site recognized and interacted by Cbl among the structures of c-Met and it enables the intracellular migration and degradation of c-Met by Cbl. The typical interaction site of c-Met with Cbl may be the $1003^{th}$ amino acid residue, tyrosine (Y1003), which is an interaction site with Cbl, or a site encoded by exon 14 of c-Met genes. The exon 14 region of c-Met genes may be a site from the $3075^{th}$ to $3215^{th}$ positions of the full-length nucleotide sequences of GenBank Accession No. NM_000245, or a site from the $964^{th}$ to $1009^{th}$ positions of the full-length amino acid sequences of GenBank Accession No. NP_000236. The c-Met mutations may be a deletion of the $1003^{th}$ amino acid residue, tyrosine (Y1003), from c-Met, or a substitution with other amino acids (for example, amino acid selected from the group consisting of alanine, isoleucine, leucine, methionine, phenylalanine, proline, tryptophan, valine, asparagine, cysteine, glutamine, glycine, serine, threonine, aspartate, glutamate, arginine, histidine and lycine, and particularly, phenylalanine), or a deletion of a successive 141 or more nucleotides (for example, a successive 141 to 300 nucleotides) from exon 14 region of the c-Met genes, or a substitution with other nucleotides. Additionally or alternatively, the c-Met mutations may be a deletion of a successive 46 or more amino acids (for example, a successive 46 to 100 amino acids) from the polypeptide encoded by exon 14 region or a substitution with other amino acids. In a particular embodiment, the c-Met mutations may be a deletion of the $1003^{th}$ amino acid residue, tyrosine (Y1003), of c-Met or a substitution with phenylalanine (that is, Y1003F), a deletion of the exon 14 region of the c-Met genes, or a deletion of polypeptides encoded by the exon 14 region from the c-Met proteins.

Whether such c-Met mutations occur or not may be identified by direct analysis of nucleotide sequences or amino acid sequences, by measuring them via RT-PCR or DNA sequencing methods, etc., and/or by evaluating the measured results, but not limited thereto. A substance capable of detecting c-Met mutations may be a primer capable of detecting such mutations (successive 20 to 50 sequences containing mutated sites among the nucleotide sequences of mutated Cbl genes and/or sequences complementary thereto or sequences having 80% or more, particularly 90% or more, and more particularly 95% or more of sequence identity/homology that can hybridize therewith), an antibody or an aptamer specifically binding to mutated c-Met, etc., but not limited thereto.

The pharmaceutical compositions may be used for the prevention and/or treatment of c-Met and angiogenesis factors (e.g., VEGF) induced diseases such as those induced by increase in copy number and/or expression amount of c-Met and/or over-expression of angiogenesis factors (e.g., VEGF), typically cancers. The cancers may be those that over-express c-Met and angiogenesis factors (e.g., VEGF) or solid cancers, or they may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, osteosarcoma, and soft-tissue sarcoma, but not limited thereto. In another embodiment, the diseases induced by c-Met and angiogenesis factors may be gestational diabetes, diabetic retinopathy, macular degeneration (e.g., wet age-related macular degeneration: wet AMD) and so on.

The prevention and/or treatment effects of the cancers may include effects of not only suppressing the growth of the cancer cells but also suppressing deterioration of cancers due to migration, invasion, and metastasis thereof. Therefore, the curable cancers by the co-therapy of the invention include both primary cancers and metastatic cancers.

By virtue of the combined therapy of anti-c-Met antibody and angiogenesis inhibitors (e.g., VEGF antagonists), remarkably increased synergistic effects have been achieved, compared to administration of anti-c-Met antibody or angiogenesis inhibitors alone. Further, the combined therapy enables the reduction of dosage amounts of each drug, has an excellent effect on patients on whom existing anti-c-Met antibodies have had no effect because of mutations in Cbl and/or c-Met, and has an excellent effect against not only primary cancers but also metastatic cancers. Diseases that can be treated (cured) can be, besides cancers, other diseases associated with c-Met/HGF signal transduction system and VEGF/VEGFR signal transduction system.

Hereafter, the present invention will be described in detail by examples.

The following examples are intended merely to illustrate the invention and are not construed to restrict the invention.

EXAMPLES

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1 \sim 2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment including the heavy chain nucleotide sequence (SEQ ID NO: 38) and a DNA fragment including the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the vectors thus constructed was amplified with the aid of a Qiagen Maxiprep kit (Cat no. 12662). The vectors which respectively carried the heavy chain and the light chain were co-transfected at a ratio of 4:1 (80 μg:20 μg) into 293T cells ($2.5 \times 10^7$). The transfection into 293T cells ($2.5 \times 10^7$) was performed in the presence of 360 μL of 2M $CaCl_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1.

Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments including the heavy chain nucleotide sequences (H1-heavy: SEQ ID NO: 47, H3-heavy: SEQ ID NO: 48, H4-heavy: SEQ ID NO: 49) and DNA fragments including the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the recombinant vectors was amplified using Qiagen Maxiprep kit (Cat no. 12662). The vectors which respectively carried the heavy chain and the light chain were co-transfected at a ratio of 4:1 (80 μg:20 μg) into 293T cells ($2.5 \times 10^7$). The transfection into 293T cells ($2.5 \times 10^7$) was performed in the presence of 360 μL of 2 M $CaCl_2$. Afterwards, the cells were incubated in DMEM supplemented with 10% (v/v) FBS for 5 hours at 37° C. under a 5% $CO_2$ condition, and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 1, below.

TABLE 1

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 2

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the recombinant vectors was amplified using a Qiagen Maxiprep kit (Cat no. 12662). The vectors which respectively carried the heavy chain and the light chain were co-transfected at a ratio of 4:1 (80 μg:20 μg) into 293T cells (2.5×10⁷). The transfection into 293T cells (2.5×10⁷) was performed in the presence of 360 μL of 2 M CaCl₂. Afterwards, the cells were incubated in DMEM supplemented with 10% (v/v) FBS for 5 hours at 37° C. under a 5% CO₂ condition and then in FBS-free DMEM for 48 hours at 37° C. under a 5% CO₂ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 constant region, a polynucleotide (SEQ ID NO: 67) encoding a polypeptide (SEQ ID NO: 66) composed of the heavy chain variable region of huAbF46-H4-A1, a human IgG2 hinge region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the vectors thus constructed was amplified with the aid of a Qiagen Maxiprep kit (Cat no. 12662). The vectors which respectively carried the heavy chain and the light chain were co-transfected at a ratio of 4:1 (80 μg:20 μg) into 293T cells (2.5×10⁷). The transfection into 293T cells (2.5×10⁷) was performed in the presence of 360 μL of 2 M CaCl₂. Afterwards, the cells were incubated in DMEM supplemented with 10% (v/v) FBS for 5 hours at 37° C. under a 5% CO₂ condition and then in FBS-free DMEM for 48 hours at 37° C. under a 5% CO₂ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). In the following examples, the 3 antibodies are named as follows:

huAbF46-H4-A1 (U6-HC7): L3-1Y/U6-HC7/IgG1 or L3-1Y huAbF46-H4-A1 (IgG2 hinge): L3-1Y/U3-HC9/IgG1 or L3-1Y/U3HC9 huAbF46-H4-A1 (IgG2 Fc): L3-1Y/U3-HC9/IgG2 or L3-1Y/IgG2

Example 1

Agonism Test of c-Met Antibodies

The agonism levels of c-Met antibody L3-1Y, its modified forms L3-1Y/U3HC9/IgG1 (a hinge part of L3-1Y modified by U3HC9), and L3-1Y/U3HC9/IgG2 (a hinge of L3-1Y and Fc modified) prepared in the above reference examples were measured and compared with 5D5 (American Type Culture Collection (ATCC, Manassas, Va.) which was a previously developed c-Met antibody, as a positive control.

In order to investigate agonism (weakness to the safety of the antibody), a BrdU assay was performed.

The BrdU assay was as follows. Human lung cancer cells, NCI-H441 cells (ATCC Cat. #HTB-174) were suspended in serum-free RPMI 1640 media (Gibco) at 2×10⁵ cells/mL and the suspensions were seeded onto a 96-well tissue culture plate (Corning, Lowell, Mass.) with 100 μL per well. For 24 hours, the cells were cultured at 37° C. under the condition of 5% CO₂. After the complete removal of the media, RPMI 1640 media was added with antibodies (L3-1Y, L3-1Y/U3HC9, L3-1Y/IgG2, 5D5, IgG (eBioscience)) serially diluted from 10 μg/mL to 0.001 μg/mL. After culture for 21 hours at 37° C. under the condition of 5% CO₂, 5-bromo-2'-deoxyuridine (BrdU) was added and then cultured for additional 3 hours, followed by the BrdU assay (Roche, Indianapolis, Ind.). After the denaturation/fixation of cells on plates, anti-BrdU antibody was added and after 1 hour, substrates were added, and then, luminescence reactions were measured using ELISA spectraMax reader (Molecular Devices, Sunnyvale, Calif.) at 370 nm. Comparisons were made based on the functionality of mouse AbF46 antibody. As a negative control, IgG of mouse was used and as a positive control, 5D5 antibody (ATCC Cat. no. HB11895 isolated and purified from hybridoma cells), which was well known as an agonist, was used.

Finally, after the value of cells incorporated with no BrdU was deducted as a background control, the relative DNA synthesis (%) was calculated as relative values with regard to the control group value (100%) treated with no anti-c-Met antibody and shown in FIG. 1.

As shown in FIG. 1, antibody L3-1Y and its modified forms exhibited remarkably low agonism in comparison with their positive control 5D5. In FIG. 1, L3-1Y/U6-HC7/IgG1, L3-1Y/U3-HC9/IgG1, and L3-1Y/U3-HC9/IgG2 refer to L3-1Y, L3-1Y/U3HC9, and L3-1Y/IgG2, respectively.

DNA synthesis is essential for cell division as cells grow. DNA replication takes place at S phase, where the bonding of A-T and G-C occurs and bromide is required for this. Hence, the growth of cells can be measured by the amounts of bromide and in the case that cells grow a lot for the same period of time, it is considered that agonism exists and thus, a BrdU assay can be used as an agonism assay. That is, it is interpreted that if the value of BrdU is small, the amount of DNA synthesized within the same amount of time is also small and the growth of cells is accordingly slow and thus, it can be considered to be a reduction in agonism.

Example 2

AKT Phosphorylation Inhibition Test of c-Met Antibodies

A low agonism of anti-c-Met antibodies proposed in this invention has been verified once again by mechanism-based experiments concerning safety and efficiency.

In order to see the safety of the antibodies, the phosphorylation level of AKT was quantified by ELISA. Cellular mechanisms to be regulated by AKT may be cell proliferation, cell survival, cell size control, reactivity to available nutrients, intermediate metabolic process, angiogenesis, tissue invasion, etc. These processes are typical characteristics of cancer cells, and numerous oncoproteins and tumor suppressors mutually affect each other in AKT pathways and play a role in finely regulating the functions of cells at connection points of signal transduction and classic metabolic regulation. Hence, since the fact that AKT is phosphorylated and thus activated highly means having a high tumor-forming potential, the anticancer effects of antibodies can be tested by measuring the phosphorylation inhibition levels of AKT according to antibody treatment.

A site of AKT to be phosphorylated is Ser473, and the phosphorylation of AKT was measured using PathScan phospho-AKT1 (Ser473) chemiluminescent Sandwich ELISA kit (Cell signaling Co.).

On the day before the test, Caki-1 kidney cancer cell lines (HTB-46; American Type Culture Collection (ATCC), Manassas, Va.) cultured at $2 \times 10^5$ cells/mL were mixed with 5 μg/mL of antibodies in serum-free DMEM media and treated for 30 minutes and then, the ELISA kit was employed.

The phosphorylation levels of the antibodies were calculated as relative values with regard to the phosphorylation level of 5D5 as a positive control (100%).

The obtained results are shown in FIG. 2. As shown in FIG. 2, the antibody L3-1Y and its modified forms exhibited remarkably high AKT phosphorylation inhibition effects in comparison with their positive control, 5D5.

Example 3 c-Met Degradation Induction Test of c-Met Antibodies

The fact that the antibody L3-1Y and its modified forms have low agonism and, at the same time, have an excellent c-Met degradation efficacy was verified by measuring the total amounts of c-Met. Since the bonding of c-Met and HGF has already known to promote the growth of cancer cells, a reduction in the total amounts of c-Met by antibody treatment would indicate a decrease in the growth of the cancer cells, and through this, the anticancer activities of the antibodies can be verified.

The c-Met degradation induction activities of c-Met antibody L3-1Y and its modified forms L3-1Y/U3HC9 (hinge modified), and L3-1Y/IgG2 (hinge and Fc modified) prepared in the above reference examples were measured. The c-Met degradation levels in this example are shown through the total amounts of c-Met measured using ELISA.

$2 \times 10^5$ cells/mL of MKN45 stomach cancer cell lines were mixed with 5 μg/mL of each antibody and cultured for 24 hours (RPMI media, GIBCO) and then, they were subject to ELISA experiments using human total HGF R/c-Met ELISA kit (R&D systems). Finally, Super Aquablue (eBiosciences) was added, and colorimetric signals were measured as OD values at the wavelength of 450 nm. The values measured with regard to each antibody were converted into relative values with regard to the control group treated with no antibodies (media only, 100%) and shown in FIG. 3.

As shown in FIG. 3, the c-Met antibody and its modified forms exhibited a remarkably superior c-Met degradation efficacy in comparison with the control group treated with no antibodies.

Example 4

Cell Growth Inhibition Effects by Combined Therapy of an Anti-c-Met Antibody and a VEGF Antagonist In order to investigate a cell growth inhibition level by combined therapy of anti-c-Met antibody L3-1Y or L3-1Y/IgG2, and a VEGF antagonist, avastin (Roche), real time cell analysis was carried out using xCelligence system (Roche).

10000 cells/well of cells (HuVEC, ATCC) were treated with 0.4 μg/mL of HGF (R&D systems), a ligand of c-Met and VEGFR, and 0.4 μg/mL of VEGF (PENGEN), and it was observed how the improved growth of the cells could be inhibited by the anti-c-Met antibody L3-1Y, L3-1Y/IgG2, avastin, or the combined therapy thereof.

The apparatus used in this analysis has xCelligence-RTCA (Real time cell analyzer) DP system, and it enables counting the number of cells by measuring real time impedences occurring whenever cells are attached onto a gold microelectrode array.

E-plate 16 was employed, and 10000 cells/well of cells (HuVEC, ATCC) and 10 μg/mL of each antibody, 10 μg/mL of avastin (Roche), or a mixture thereof were added into each well of the plate and then, the occurring impedance values were measured in real time. A cell index refers to a relative impedence value occurring by the attachment of cells to the bottom and is shown in FIG. 4 and FIG. 12.

In FIG. 4, ① indicates the result from the cells treated with VEGF+HGF, ② indicates the result from the cells treated with avastin alone, ③ indicates the result from the cells treated with antibody L3-1Y alone, ④ indicates the result from the cells co-treated with antibody L3-1Y and avastin, and ⑤ indicates the result from the cells with no treatments (media only). As shown in FIG. 4, cell growth was more obviously inhibited when co-treated than when treated with either antibody L3-1Y or avastin alone.

Figure 5:
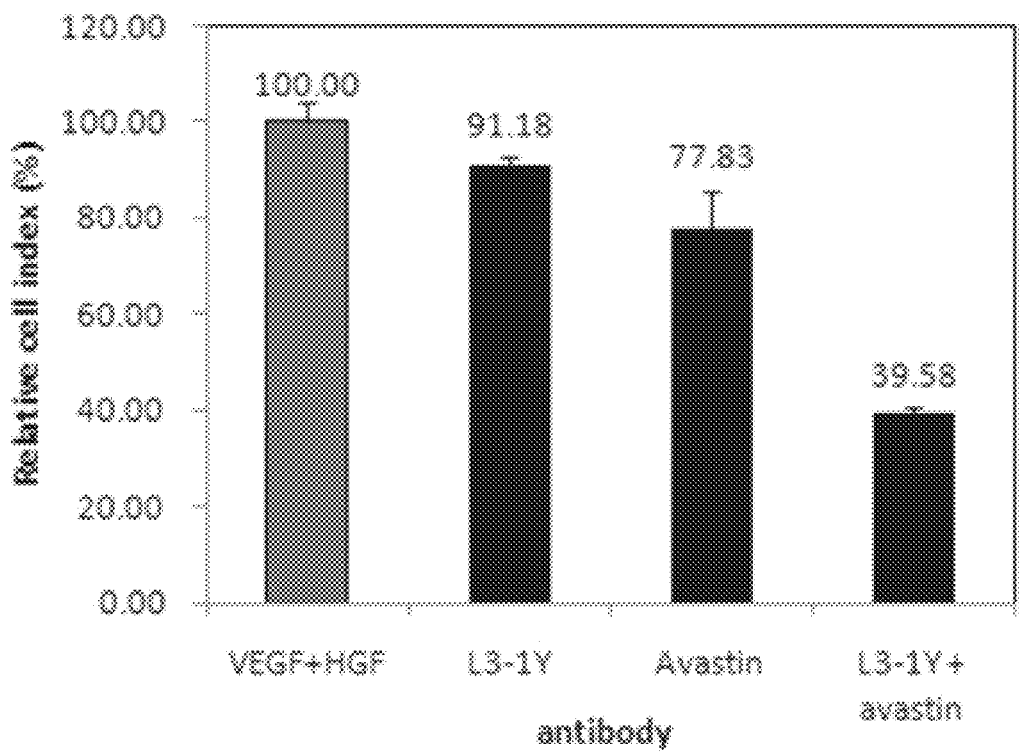
FIG. 5 is a graph showing the relative cell index (%) after administration of L3-1Y, avastin, or both L3-1Y and avastin (with 92 hours and 18 minutes and 9 seconds as an end point in the real time cell analysis).

Further, at the point at which the positive control (VEGF+ HGF treatment group) reached its maximum growth as a result of real time cell analysis of FIG. 4 (92 hours and 18 minutes and 9 seconds), the inhibition levels of the antibody L3-1Y, avastin, and the co-treatment thereof were calculated as relative values with regard to the positive control-negative control (no treat group) (100%) and shown in FIG. 5.

In FIG. 12, ① indicates the result from the cells treated with VEGF+HGF, ② indicates the result from the cells treated with avastin alone, ③ indicates the result from the cells treated with antibody L3-1Y/IgG2 alone, ④ indicates the result from the cells co-treated with antibody L3-1Y/ IgG2 and avastin, and ⑤ indicates the result from the cells with no treatments (media only). As shown in FIG. 12, cell growth was more obviously inhibited when co-treated than when treated with either antibody L3-1Y/IgG2 or avastin alone.

Further, at the point at which the positive control (VEGF+ HGF treatment group) reached its maximum growth as a result of real time cell analysis of FIG. 13 (71 hours and 54 minutes and 17 seconds), the inhibition levels of the antibody L3-1Y/IgG2, avastin, and the co-treatment thereof were calculated as relative values with regard to the positive control-negative control (no treat group) (100%) and shown in FIG. 13.

As shown in FIG. 5 and FIG. 13, remarkably superior cell growth inhibition effects resulted when the antibody L3-1Y or L3-1Y/IgG2 and avastin were co-administered in comparison with treatment with each of them alone.

After the cell growth inhibition level by the combined therapy of anti-c-Met antibody and avastin was tested using xCelligence system (Roche Co.), patterns of each administrated material according to concentration were investigated using CCK-8 assay at 96-wells.

First, HuVEC cells (ATCC) were seeded onto a 96-well plate with complete media (lonza, cc-3162) at the amount of 10000 per well. After the culture for 24 hours, the media were replaced by serum-free media (lonza, cc-3121), which were mixed with anti-c-Met antibody L3-1Y, avastin, or a mixture thereof having various concentrations (0.05 to 5 µg/mL), and then, after 72 hours, a CCK-8 assay was carried out to read and analyze occurring signals.

Figure 6:
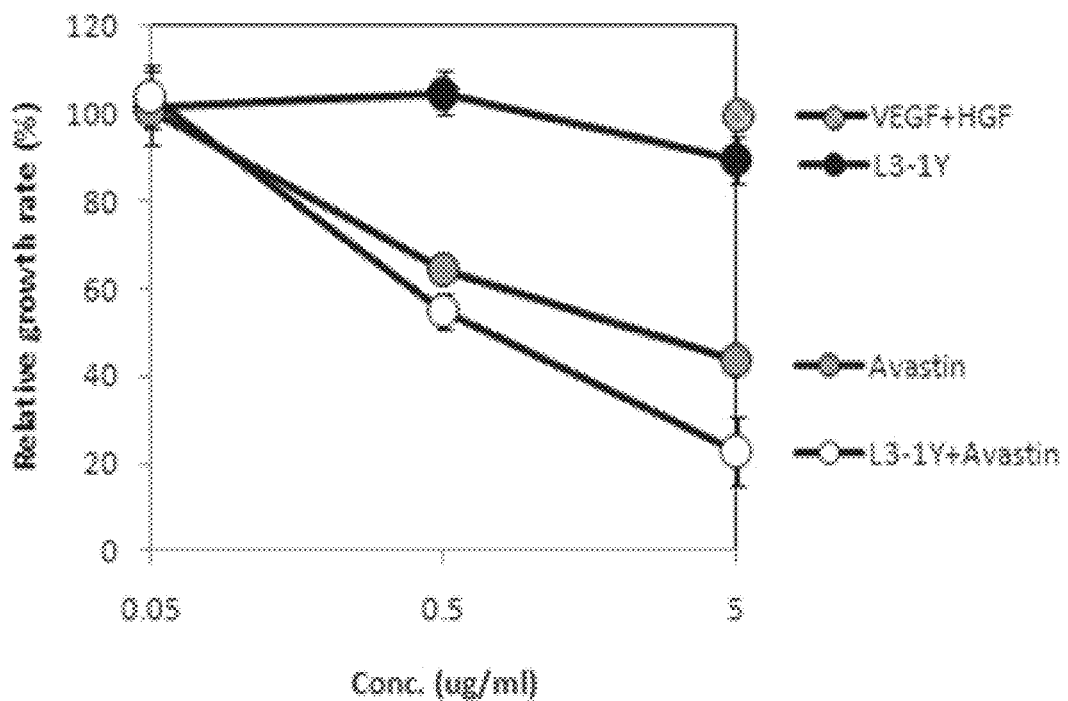
FIG. 6 is a graph showing cell growth inhibition effects in proportion to concentrations when L3-1Y and avastin were co-administered. Relative growth rate (%) is indicated on the y-axis, and concentration (μg/mL) is indicated on the x-axis.

The obtained results are shown in FIG. 6. As shown in FIG. 6, higher cell growth inhibition effects were obtained when anti-c-Met antibody L3-1Y and avastin were co-administered than when each was administered individually, and such effects were observed to increase in proportion to their concentrations.

Example 5

Cell Metastatic Potential Inhibition Effects by Combined Therapy of an Anti-c-Met Antibody and a VEGF Antagonist Both c-Met and VEGF are factors associated with not only cell growth but also the metastasis of cancers. Whether the combined therapy of each inhibitor has synergistic effects on cell mobility related to cancer cell metastatic potential was investigated.

Oris 96-well plate (Platypus, Oris™ Cell migration assay) method was performed. HuVEC cells (ATCC) were seeded onto each well of a 96-well plate equipped with a stopper at 10000 per well and treated with 0.4 µg/mL of HGF and 0.4 µg/mL of VEGF in serum-free media (EBM, Lonza) and then, after the culture for 24 hours, the stoppers were removed. Because the stopper, as a circular rubber material, prevents cells from growing at place where the stopper was put, the removal of the stopper after 24 hours would produce circular space at only that place.

After the removal of the stoppers, the cells were treated with anti-c-Met antibody L3-1Y, avastin, and a mixture thereof in the amount of 10 µg/mL, respectively. After 24 hours, calcein AM (BD), which is a fluorescent substance, was added so that only cells were dyed and portions with no cells remained as spaces. Hence, as cell mobility is inhibited, the size of spaces which are not dyed will increase. Accordingly, cell mobility level can be measured by observing the spaces that are not dyed.

Since the migration of cells is directly associated with the metastasis of cancers, such analysis is a method commonly used to evaluate the metastatic potential of cells. In particular, this analysis is a method used to determine whether cells migrate to neighboring ranges.

Figure 7:
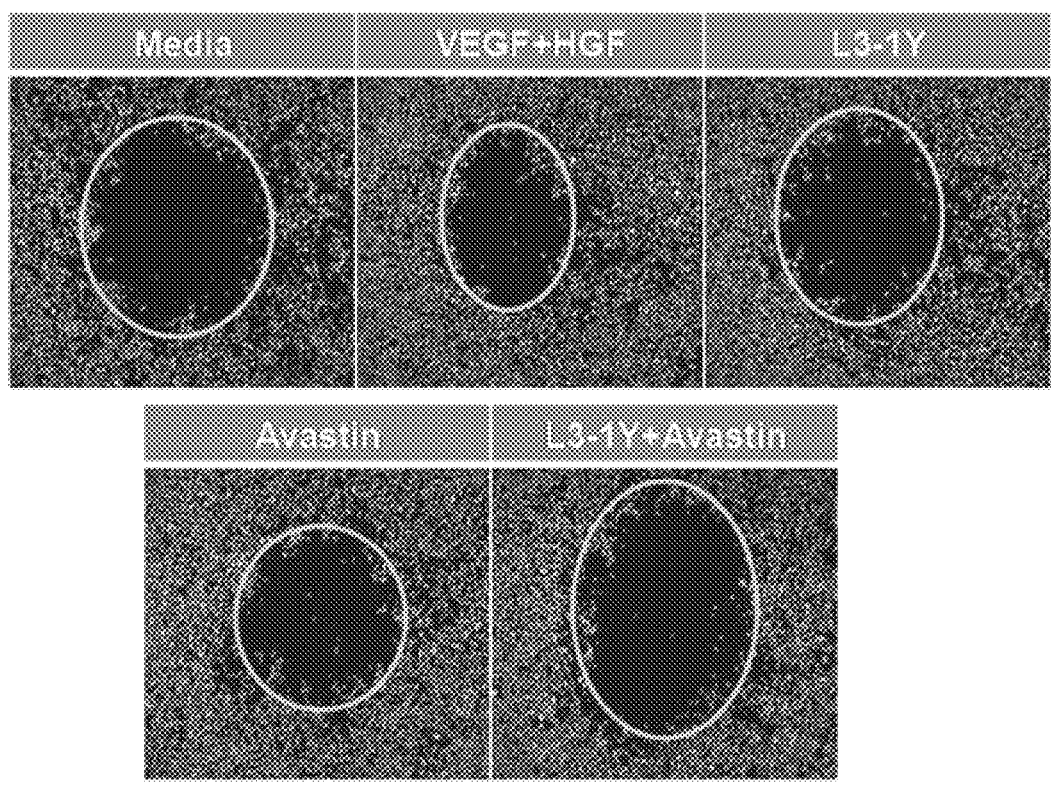
FIG. 7 is a series of images depicting calcein AM dye forms on an Oris 96-well plate of cells (HuVEC, Human Umbilical Vein Endothelial Cells) treated with the antibody and/or avastin, and demonstrating cell metastatic potential evaluation results.

After the test, the images of cell dye and the spaces with no dye were photographed with a fluorescence spectroscopy and the results are shown in FIG. 7. As shown in FIG. 7, the treatment of the growth factors HGF and VEGF in serum-free media improved cell migration. However, the treatment of anti-c-Met antibody L3-1Y, avastin, or the mixture thereof together with the growth factors re-inhibited the cell migration improved by the growth factors and, thus, resulted in large empty spaces with no dyes. Such effects were obvious especially in the combined therapy group of anti-c-Met antibody L3-1Y and avastin.

Figure 8:
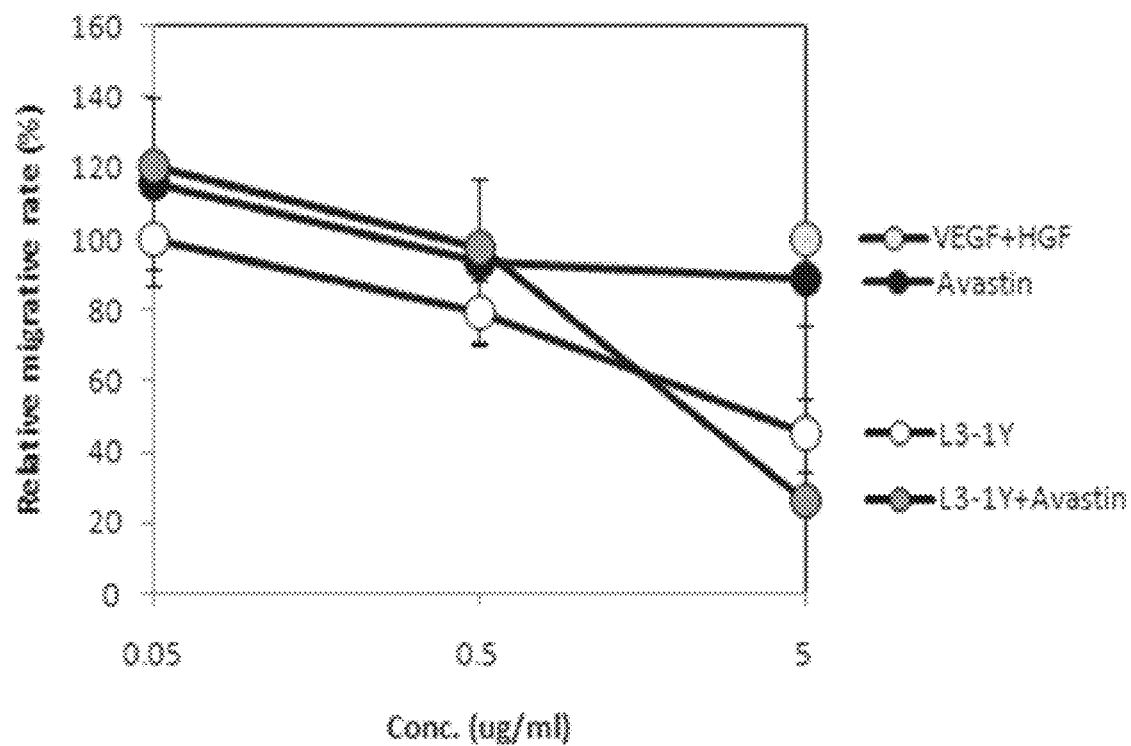
FIG. 8 is a graph showing cell metastatic potential inhibition effects measured using an Oris 96-well plate, in proportion to the concentrations of treatment drugs. Relative migrative rate (%) is indicated on the y-axis, and concentration (μg/mL) is indicated on the x-axis.

In order to see effects in proportion to the concentrations of anti-c-Met antibody L3-1Y and/or avastin, fluorescence signal strengths obtained by the treatment of anti-c-Met antibody L3-1Y, avastin, or the mixture thereof having a variety of concentrations (0.05 to 5 µg/mL) were measured using a multilabel reader (Perkin-Elmer, Envision) according to a method identical to the method used in obtaining the results of FIG. 7, and the measured values were converted with regard to 100% of the signal strength of VEGF+HGF treatment group and shown in FIG. 8. As shown in FIG. 8, the anti-c-Met antibody L3-1Y and avastin exhibited cell growth inhibition effects in a concentration-dependent manner, and such effects were remarkably increased when anti-c-Met antibody L3-1Y and avastin were co-administered.

Figure 9:
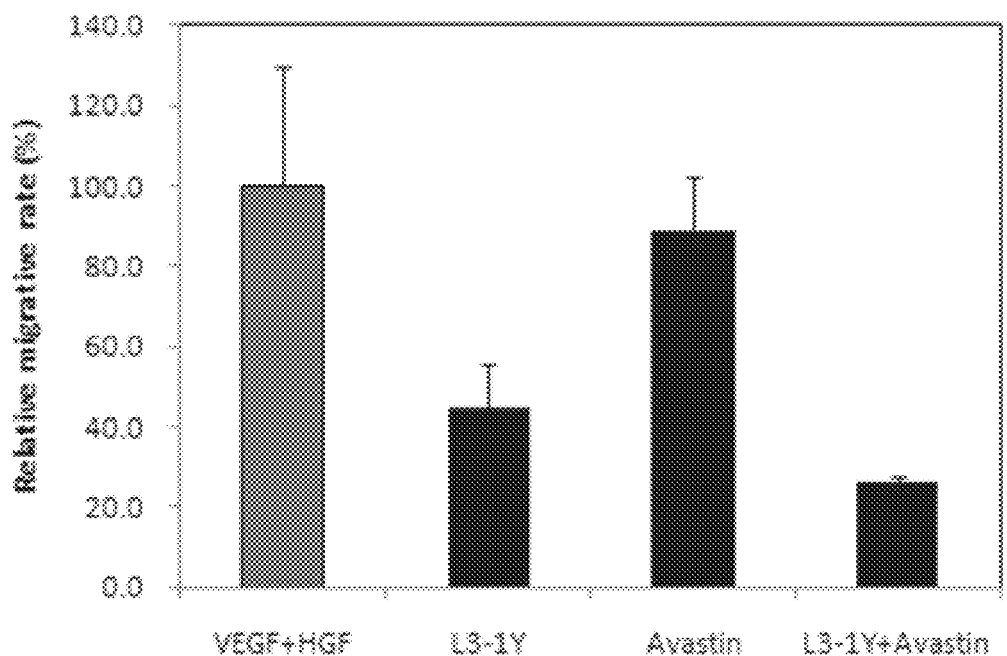
FIG. 9 is a graph showing the results of comparing the cell metastatic potential inhibition effects measured using an Oris 96-well plate at the maximum concentration of treatment drugs. Relative migrative rate (%) is indicated on the y-axis for the particular therapy (x-axis).

The effects at the maximum concentration (5 µg/mL) were summarized in the form of a bar graph and shown in FIG. 9. As shown in FIG. 9, whereas the administration of avastin alone had little cell migration inhibition effect, the co-treatment of the anti-c-Met antibody L3-1Y and avastin obviously enhanced cell migration inhibition efficacy.

Example 6

Cell Penetration Potential Inhibition Effects by Combined Therapy of an Anti-c-Met Antibody and a VEGF Antagonist In order to verify whether the combined therapy of the anti-c-Met antibody L3-1Y and avastin inhibits a cell penetration potential, the cell penetration potential was tested using a plate for cell penetration potential assay (BioCoat Growth Factor Reduced MATRIGEL Invasion Chamber; BD science, Cat no. 354483), which is divided into an upper chamber and a lower chamber and the upper chamber onto which a collagen is coated.

Figure 10:
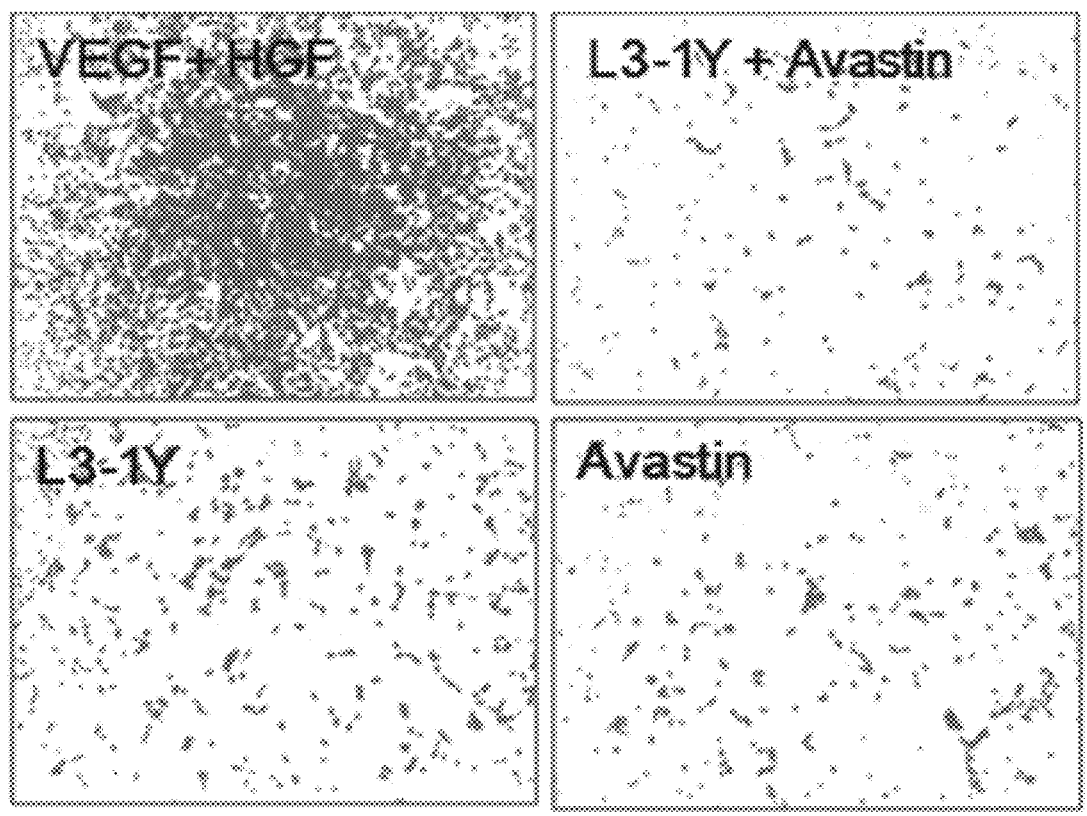
FIG. 10 is a series of images showing the penetration potentials of HUVEC cells according to treatment drugs.

HUVEC cells (ATCC; $5 \times 10^4$) were seeded onto the upper chamber. Mixtures obtained by mixing media (EBM) with the anti-c-Met antibody L3-1Y, avastin, or a mixture thereof in the amount of 10 μg/mL, respectively. were placed in the lower chamber and then cultured (HGF+VEGF was added in the lower chamber at 0.4 μg/mL, respectively). After the culture for 24 hours, cells which went down to the lower chamber by penetrating the upper collagen layer were dyed with calcein and observed using florescence spectroscopy. Such collagen layer penetration potential by cells is largely employed to determine the metastatic potential of cells to distant tissues or organs. The obtained fluorescence images are shown in FIG. 10. As shown in FIG. 10, after both VEGF and HGF were treated, the co-treatment of the anti-c-Met antibody L3-1Y and avastin remarkably inhibited cell penetration potential in comparison with the cases treated with each of them alone.

Further, the fluorescence areas were calculated from the fluorescence images obtained in the above and shown in FIG. 11. As shown in FIG. 11, the co-treatment of the anti-c-Met antibody L3-1Y and avastin obviously reduced the areas occupied by cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A method for treatment of cancer metastasis, the method comprising co-administering (a) a VEGF antagonist and (b) an anti-c-Met antibody or antigen-binding fragment thereof to a subject in need thereof,
wherein the anti-c-Met antibody or the antigen-binding fragment thereof comprises:
a heavy chain variable region comprising a complementarity determining region (CDR)-H1 comprising an amino acid sequence selected from the group consisting of SEQ ID NOs: 1, 22, 23, and 24; a CDR-H2 comprising an amino acid sequence selected from the group consisting of SEQ ID NOs: 2, 25, and 26; and a CDR-H3 comprising an amino acid sequence selected from the group consisting of SEQ ID NOs: 3, 27, and 28; and
a light chain variable region comprising a CDR-L1 comprising an amino acid sequence selected from the group consisting of SEQ ID NOs: 10, 29, 30, 31, 32, 33, and 106, a CDR-L2 comprising an amino acid sequence selected from the group consisting of SEQ ID NOs: 11, 34, 35, and 36, and a CDR-L3 comprising an amino acid sequence selected from the group consisting of SEQ ID NOs: 12, 13, 14, 15, 16, and 37.

2. The method of claim 1, wherein the angiogenesis inhibitor and the anti-c-Met antibody are administered simultaneously or sequentially in any order.

3. The method according to claim 1, wherein the VEGF antagonist comprises at least one selected from the group consisting of bevacizumab, VEGF-trap, sunitinib, sunitinib malate, AEE-788, axitinib, AG-028262, combretastatin A4 analog, cediranib, BMS-387032, CEP-7055, CHIR-258, CP-547632, CP-564959, E-7080, Pazopanib, GW-654652, indazolylpyrimidine Kdr inhibitors, KRN-951, quinoline-urea VEGF inhibitors, midostaurin, vatalanib, anilinophthalazine derivative VEGF inhibitors, semaxanib, SU-6668, thalidomide, XL-647, XL-999, vandetanib, anilinoquinazoline VEGF inhibitors, ZK-304709, indirubin derivative VEGF inhibitors, CDP791, Enzastaurin, BIBF 1120, BAY 573952, BAY 734506, XL 184, IMC-1121B, CEP 701, SU 014813, SU 10944, SU 12662, OSI-930, BMS 582664, N-acetylcolchinol phosphate, ANG-400 series drugs, Imatinib, everolimus, and dasatinib.

4. The method according to claim 1, wherein the anti c-Met antibody or the antigen-binding fragment thereof specifically binds to an epitope consisting of the amino acid sequence of SEQ ID NO: 71, 72, or 73.

5. The method according to claim 1, wherein the heavy chain variable region comprises an amino acid sequence selected from the group consisting of SEQ ID NO: 17, 74, 87, 90, 91, 92, 93, and 94, and the light chain variable region comprises an amino acid sequence selected from the group consisting of SEQ ID NO: 18, 19, 20, 21, 75, 88, 95, 96, 97, 98, 99, 107, and 132.

6. The method according to claim 1, wherein the anti c-Met antibody comprises:
a heavy chain comprising an amino acid sequence selected from the group consisting of SEQ ID NO: 62, SEQ ID NO: 64, SEQ ID NO: 66, the amino acid sequence from the $18^{th}$ to $462^{nd}$ positions of SEQ ID NO: 62, the amino acid sequence from the $18^{th}$ to $461^{st}$ positions of SEQ ID NO: 64, and the amino acid sequence from the $18^{th}$ to $460^{th}$ positions of SEQ ID NO: 66, and
a light chain comprising an amino acid sequence selected from the group consisting of SEQ ID NO: 68, SEQ ID NO: 70, SEQ ID NO: 108, the amino acid sequence from the $21^{st}$ to $240^{th}$ positions of SEQ ID NO: 68, and the amino acid sequence from the $21^{st}$ to $240^{th}$ positions of SEQ ID NO: 70.

7. The method according to claim 6, wherein the anti c-Met antibody comprises:
a heavy chain comprising the amino acid sequence from the $18^{th}$ to $460^{th}$ positions of SEQ ID NO: 66, and
a light chain comprising the amino acid sequence from the $21^{st}$ to $240^{th}$ positions of SEQ ID NO: 68.

8. The method according to claim 1, wherein the anti c-Met antibody is monoclonal.

9. The method according to claim 1, wherein the anti c-Met antibody is an antibody of mouse origin, a mouse-human chimeric antibody, or a humanized antibody.

10. The method according to claim 1, wherein the antigen-binding fragment is selected from the group consisting of scFv, (scFv)$_2$, Fab, Fab', and F(ab')$_2$.

* * * * *

SEQUENCE LISTING

```
<160> NUMBER OF SEQ ID NOS: 132

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
  1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
  1               5                  10                  15

Val Lys Gly
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: misc_feature
<222> LOCATION: (1)
<223> OTHER INFORMATION: X is Pro or Ser or absent
<220> FEATURE:
<221> NAME/KEY: misc_feature
<222> LOCATION: (2)
<223> OTHER INFORMATION: X is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: misc_feature
<222> LOCATION: (3)
<223> OTHER INFORMATION: X is Asn or Lys
<220> FEATURE:
<221> NAME/KEY: misc_feature
<222> LOCATION: (4)
<223> OTHER INFORMATION: X is Ala or Val
<220> FEATURE:
<221> NAME/KEY: misc_feature
<222> LOCATION: (7)
<223> OTHER INFORMATION: X is Asn or Thr

<400> SEQUENCE: 5

Arg Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: misc_feature
<222> LOCATION: (5)
<223> OTHER INFORMATION: X is Ser or Thr

<400> SEQUENCE: 6

Asp Asn Trp Leu Xaa Tyr
 1               5

<210> SEQ ID NO 7
<211> LENGTH: 17
<212> TYPE: PRT
```

<213> ORGANISM: Artificial Sequence
<220> FEATURE:
<223> OTHER INFORMATION: Synthetic light chain CDR1 of c-Met antibody
<220> FEATURE:
<221> NAME/KEY: misc_feature
<222> LOCATION: (4)
<223> OTHER INFORMATION: X is His, Arg, Gln or Lys
<220> FEATURE:
<221> NAME/KEY: misc_feature
<222> LOCATION: (12)
<223> OTHER INFORMATION: X is His or Gln
<220> FEATURE:
<221> NAME/KEY: misc_feature
<222> LOCATION: (13)
<223> OTHER INFORMATION: X is Lys or Asn
<220> FEATURE:
<221> NAME/KEY: misc_feature
<222> LOCATION: (9)
<223> OTHER INFORMATION: X is Ser or Trp

<400> SEQUENCE: 7

Lys Ser Ser Xaa Ser Leu Leu Ala Xaa Gly Asn Xaa Xaa Asn Tyr Leu
 1               5                  10                  15
Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: misc_feature
<222> LOCATION: (2)
<223> OTHER INFORMATION: X is Ala or Gly
<220> FEATURE:
<221> NAME/KEY: misc_feature
<222> LOCATION: (4)
<223> OTHER INFORMATION: X is Thr or Lys
<220> FEATURE:
<221> NAME/KEY: misc_feature
<222> LOCATION: (7)
<223> OTHER INFORMATION: X is Ser or Pro

<400> SEQUENCE: 8

Trp Xaa Ser Xaa Arg Val Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: misc_feature
<222> LOCATION: (1)
<223> OTHER INFORMATION: X is Gly, Ala or Gln
<220> FEATURE:
<221> NAME/KEY: misc_feature
<222> LOCATION: (6)
<223> OTHER INFORMATION: X is Arg, His, Ser, Ala, Gly or Lys
<220> FEATURE:
<221> NAME/KEY: misc_feature
<222> LOCATION: (8)
<223> OTHER INFORMATION: X is Leu, Tyr, Phe or Met

<400> SEQUENCE: 9

Xaa Gln Ser Tyr Ser Xaa Pro Xaa Thr
 1               5

<210> SEQ ID NO 10

```
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
 1               5                  10                  15
Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110
```

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26

```
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
 1               5                   10                  15
```

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
 1               5                  10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
 1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
  1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttcctcg taacactttt aaatggtatc      60
cagtgtgagg tgaagctggt ggagtctgga ggaggcttgg tacagcctgg gggttctctg     120
agactctcct gtgcaactcc tgggttcacc ttcactgatt actacatgag ctgggtccgc     180
cagcctccag aaaggcact tgagtggttg gtttttatta aaacaaagc taatggttac     240 acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggttttgc ttactgggggc caagggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020

| | |
|---|---|
| tacaagtgca aggtctccaa caaagccctc ccagccccca tcgagaaaac catctccaaa | 1080 |
| gccaaagggc agccccgaga accacaggtg tacaccctgc ccccatcccg ggaggagatg | 1140 |
| accaagaacc aggtcagcct gacctgcctg gtcaaaggct tctatcccag cgacatcgcc | 1200 |
| gtggagtggg agagcaatgg gcagccggag aacaactaca agaccacgcc tcccgtgctg | 1260 |
| gactccgacg gctccttctt cctctacagc aagctcaccg tggacaagag caggtggcag | 1320 |
| caggggaacg tcttctcatg ctccgtgatg catgaggctc tgcacaacca ctacacgcag | 1380 |
| aagagcctct ccctgtctcc gggtaaatga ctcgag | 1416 |

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

| | |
|---|---|
| gaattcacta gtgattaatt cgccgccacc atgattcac aggcccaggt cctcatgttg | 60 |
| ctgctgctat cggtatctgg tacctgtgga gacattttga tgacccagtc tccatcctcc | 120 |
| ctgactgtgt cagcaggaga gaaggtcact atgagctgca agtccagtca gagtctttta | 180 |
| gctagtggca accaaaataa ctacttggcc tggcaccagc agaaaccagg acgatctcct | 240 |
| aaaatgctga taatttgggc atccactagg gtatctggag tccctgatcg cttcataggc | 300 |
| agtggatctg ggacggattt cactctgacc atcaacagtg tgcaggctga agatctggct | 360 |
| gtttattact gtcagcagtc ctacagcgct ccgctcacgt tcggtgctgg gaccaagctg | 420 |
| gagctgaaaac gtacggtggc tgcaccatct gtcttcatct tcccgccatc tgatgagcag | 480 |
| ttgaaatctg gaactgcctc tgttgtgtgc ctgctgaata acttctatcc cagagaggcc | 540 |
| aaagtacagt ggaaggtgga taacgccctc caatcgggta actcccagga gagtgtcaca | 600 |
| gagcaggaca gcaaggacag cacctacagc ctcagcagca ccctgacgct gagcaaagca | 660 |
| gactacgaga aacacaaagt ctacgcctgc gaagtcaccc atcagggcct gagctcgccc | 720 |
| gtcacaaaga gcttcaacag gggagagtgt tgactcgag | 759 |

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt tgcttactg gggtcaagga accctggtca ccgtctcctc ggctagcacc      360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320
ctctccctgt ctccgggtaa atgactcgag                                    1350

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy
```

<400> SEQUENCE: 48

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacggt tacaccaca      180
gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg ggcacagcg      420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaccatctc caaagccaaa     1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg     1260
aacgtcttct catgctccgt gatgcatgag gctctgcaca accactacac gcagaagagc    1320
ctctccctgt ctccgggtaa atgactcgag                                     1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg     60
tcctgtgcag cttctggctt caccttcact gattactaca tgagctgggt gcgtcaggcc    120
ccgggtaagg gcctggaatg gttgggtttt attagaaaca agctaatggt tacacaaca     180
gagtacagtg catctgtgaa gggtcgtttc actataagca gagataattc caaaacacac     240
ctgtacctgc agatgaacag cctgcgtgct gaggacactg ccgtctatta ttgtgctaga    300
gataactggt ttgcttactg gggccaaggg actctggtca ccgtctcctc ggctagcacc    360
aagggcccat cggtcttccc cctggcaccc tcctccaaga gcacctctgg ggcacagcg     420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
```

| | |
|---|---|
| aacgtgaatc acaagcccag caacaccaag gtggacaaga aagttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga tgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

| | |
|---|---|
| gacatcgtga tgacccagtc tccagactcc ctggctgtgt ctctgggcga gagggccacc | 60 |
| atcaactgca gtccagcca gagtctttta gctagcggca ccaaaataa ctacttagct | 120 |
| tggcaccagc agaaaccagg acagcctcct aagatgctca tatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

| | |
|---|---|
| gatattgtga tgacccagac tccactctcc ctgcccgtca cccctggaga gccggcctcc | 60 |
| atctcctgca gtccagtca gagtctttta gctagtggca accaaaataa ctacttggcc | 120 |
| tggcacctgc agaagccagg gcagtctcca cagatgctga tcatttgggc atccactagg | 180 |
| gtatctggag tccagacag gttcagtggc agtgggtcag gcactgattt cacactgaaa | 240 |
| atcagcaggg tggaggctga ggatgttgga gtttattact gccagcagtc ctacagcgct | 300 |

| | |
|---|---|
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

| | |
|---|---|
| gacatcgtga tgacccagtc tccagactcc ctggctgtgt ctctgggcga gagggccacc | 60 |
| atcaactgca gtccagcca gagtcttta gctagcggca accaaaataa ctacttagct | 120 |
| tggtaccagc agaaaccagg acagcctcct aagctgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

| | |
|---|---|
| gatatccaga tgacccagtc cccgagctcc ctgtccgcct ctgtgggcga tagggtcacc | 60 |
| atcacctgca gtccagtca gagtcttta gctagtggca accaaaataa ctacttggcc | 120 |
| tggcaccaac agaaaccagg aaaagctccg aaaatgctga ttatttgggc atccactagg | 180 |
| gtatctggag tccttctcg cttctctgga tccgggtctg gacggattt cactctgacc | 240 |
| atcagcagtc tgcagccgga agacttcgca acttattact gtcagcagtc ctacagcgct | 300 |
| ccgctcacgt tcggacaggg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga acacaaaagt ctacgcctgc | 600 |

-continued

| gaagtcaccc atcagggcct gagctcgccc gtcacaaaga gcttcaacag gggagagtgt | 660 |
| tgactcgag | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Ser Gly
1               5                  10                 15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

| gctagcgttt tagcagaagt tcaattggtt gaatctggtg gtggtttggt tcaaccaggt | 60 |
| ggttctttga gattgtcttg tgctgcttct ggttttactt tcaccgatta ttacatgtcc | 120 |
| tgggttagac aagctccagg taaaggtttg aatggttggg ttttcattag aaacaaggct | 180 |
| aacggttaca ctaccgaata ttctgcttct gttaagggta gattcaccat ttctagagac | 240 |
| aactctaaga cacccttgta cttgcaaatg aactccttga gagctgaaga tactgctgtt | 300 |
| tattactgcg ctagagataa ttggtttgct tattgggggtc aaggtacttt ggttactgtt | 360 |
| tcttctggcc tcgggggcct cggaggagga ggtagtggcg gaggaggctc cggtggatcc | 420 |
| agcggtgtgg gttccgatat tcaaatgacc caatctccat cttctttgtc tgcttcagtt | 480 |
| ggtgatagag ttaccattac ttgtaagtcc tcccaatctt tgttggcttc tggtaatcag | 540 |
| aacaattact ggcttggcta tcaacaaaaa ccaggtaaag ctccaaagat gttgattatt | 600 |
| tgggcttcta ccagagtttc tggtgttcca tctagatttt ctggttctgg ttccggtact | 660 |
| gattttactt tgaccatttc atccttgcaa ccagaagatt tcgctactta ctactgtcaa | 720 |
| caatcttact ctgctccatt gacttttggt caaggtacaa aggtcgaaat caagagagaa | 780 |
| ttcggtaagc ctatccctaa ccctctcctc ggtctcgatt ctacgggtgg tggtggatct | 840 |
| ggtggtggtg ttctggtgg tggtggttct caggaactga caactatatg cgagcaaatc | 900 |
| ccctcaccaa ctttagaatc gacgccgtac tctttgtcaa cgactactat tttggccaac | 960 |
| gggaaggcaa tgcaaggagt ttttgaatat tacaaatcag taacgtttgt cagtaattgc | 1020 |
| ggttctcacc cctcaacaac tagcaaaggc agcccataa acacacagta tgttttttga | 1080 |
| gtttaaac | 1088 |

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference

```
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactccct tgagagctga agatactgctg tttattactg cgctagagat aattggtttg     900
cttattgggg tcaaggtact ttggttactg tttcttctgg cctcggggggc ctcggaggag     960 gaggtagtgg cggaggaggc tccgtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
```

```
aaccaggtaa agctccaaag atgttgatta tttgggcttc taccagagtt tctggtgttc    1200
catctagatt ttctggttct ggttccggta ctgattttac tttgaccatt tcatccttgc    1260
aaccagaaga tttcgctact tactactgtc aacaatctta ctctgctcca ttgactttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga gttttgaat    1560
attacaaatc agtaacgttt gtcagtaatt gcggttctca cccctcaaca actagcaaag    1620
gcagccccat aaacacacag tatgtttttt gagtttaaac ccgctgatct gataacaaca    1680
gtgtagatgt aacaaaatcg actttgttcc cactgtactt ttagctcgta caaaatacaa    1740
tatactttc atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttga    2040
cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaaagttca cctgtcccac ctgcttctga atcaaacaag ggaataaacg    2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa acatcctcc ttaggttgat    2460
tacgaaacac gccaaccaag tatttcggag tgcctgaact atttttatat gcttttacaa    2520
gacttgaaat tttccttgca ataaccgggt caattgttct cttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt cttttttcga ccgaatttct tgaagacgaa agggcctcgt    2820
gatacgccta ttttatagg ttaatgtcat gataataatg gttcttagg acggatcgct    2880
tgcctgtaac ttacacgcgc ctcgtatctt ttaatgatgg aataatttgg gaatttactc    2940
tgtgtttatt tatttttatg ttttgtattt ggatttaga aagtaaataa agaaggtaga    3000
agagttacgg aatgaagaaa aaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaatt    3300
ctttttttac tttctatttt taatttatat atttatatta aaaatttaa attataatta    3360
ttttttatagc acgtgatgaa aaggacccag gtggcacttt tcggggaaat gtgcgcggaa    3420
cccctatttg tttattttc taaatacatt caaatatgta tccgctcatg agacaataac    3480
cctgataaat gcttcaataa tattgaaaaa ggaagagtat gagtattcaa catttccgtg    3540
```

```
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta    4440
aaaggatcta ggtgaagatc ctttttgata atctcatgac caaaatccct taacgtgagt    4500
tttcgttcca ctgagcgtca ccccgtag aaaagatcaa aggatcttct tgagatcctt    4560
tttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtcagcagtc ctacagccgc cgtacacgt tcggacaggg taccaaggtg    420
gagatcaaac gtacg                                                    435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtgggcagtc ctacagccgt ccgctcacgt tcggacaggg taccaaggtg   420
gagatcaaac gtacg                                                    435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg    60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300

```
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca gtccagtca gagtcttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, U6-HC7hinge and constant region of
      human IgG1

<400> SEQUENCE: 62

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

```
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
Asn Thr Lys Val Asp Lys Lys Val Glu Pro Lys Ser Cys Asp Cys His
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttttctcg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta taagcagaga taattccaaa     300
aacacactgt acctgcagat gaacagcctg cgtgctgagg acactgccgt ctattattgt     360
gctagagata actggtttgc ttactggggc caagggactc tggtcaccgt ctcctcggct     420
```

```
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, human IgG2 hinge and constant region of
      human IgG1

<400> SEQUENCE: 64

Met Glu Trp Ser Trp Val Phe Leu Val Thr Leu Leu Asn Gly Ile Gln
 1               5                  10                  15

Cys Glu Val Gln Leu Val Glu Ser Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175
```

```
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
Asn Thr Lys Val Asp Lys Lys Val Glu Arg Lys Cys Cys Val Glu Cys
225                 230                 235                 240
Pro Pro Cys Pro Ala Pro Glu Leu Leu Gly Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser His Glu Asp Pro Glu Val Lys
        275                 280                 285
Phe Asn Trp Tyr Val Asp Gly Val Glu Val His Asn Ala Lys Thr Lys
    290                 295                 300
Pro Arg Glu Glu Gln Tyr Asn Ser Thr Tyr Arg Val Val Ser Val Leu
305                 310                 315                 320
Thr Val Leu His Gln Asp Trp Leu Asn Gly Lys Glu Tyr Lys Cys Lys
                325                 330                 335
Val Ser Asn Lys Ala Leu Pro Ala Pro Ile Glu Lys Thr Ile Ser Lys
            340                 345                 350
Ala Lys Gly Gln Pro Arg Glu Pro Gln Val Tyr Thr Leu Pro Pro Ser
        355                 360                 365
Arg Glu Glu Met Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Val Leu Asp Ser Asp Gly
                405                 410                 415
Ser Phe Phe Leu Tyr Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Gly Lys
    450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65

```
gaattcgccg ccaccatgga atggagctgg gttttttctcg taacactttt aaatggtatc     60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
```

```
gctagagata actggtttgc ttactggggc caagggactc tggtcaccgt ctcctcggct    420
agcaccaagg gcccatcggt cttcccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgcccccc ctgcccagca cctgaactcc tggggggacc gtcagtcttc    780
ctcttccccc caaaacccaa ggacaccctc atgatctccc ggaccctga ggtcacatgc    840 gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcagggaac    1320 gtcttctcat gctccgtgat gcatgaggct ctgcacaacc actacacgca gaagagcctc   1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, human IgG2 hinge and constant region
      of human IgG2

<400> SEQUENCE: 66

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
    65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
```

165                 170                 175
Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2
      hinge and constant region of human IgG2

<400> SEQUENCE: 67
gaattcgccg ccaccatgga atggagctgg gttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt     180
caggccccgg gtaagggcct ggaatggttg gttttattta gaaacaaagc taatggttac    240
acaacagagt acagtgcatc tgtgaagggg cgtttcacta taagcagaga taattccaaa    300
aacacactgt acctgcagat gaacagcctg cgtgctgagg acactgccgt ctattattgt    360

```
gctagagata actggtttgc ttactggggc caagggactc tggtcaccgt ctcctcggct    420
agcaccaagg gcccatcggt cttcccctg gcgccctgct ccaggagcac ctccgagagc      480
acagcggccc tgggctgcct ggtcaaggac tacttcccg aaccggtgac ggtgtcgtgg      540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light
      chain of huAbF46-H4-A1(H36Y) and human kappa constant region

<400> SEQUENCE: 68

Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
```

```
                165                 170                 175
Asp Asn Ala Leu Gln Ser Gly Asn Ser Gln Glu Ser Val Thr Glu Gln
                    180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and
      human kappa constant region

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc    120
tgtccgcctc tgtgggcgat agggtcacca tcacctgcaa gtccagtcag agtctttag     180 ctagtggcaa ccaaaataac tacttggcct ggtaccaaca gaaaccagga aaagctccga   240
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc gtacacgtt cggacagggt accaaggtgg    420
agatcaaacg tacggtggct gcaccatctg tcttcatctt cccgccatct gatgagcagt   480
tgaaatctgg aactgcctct gttgtgtgcc tgctgaataa cttctatccc agagaggcca    540
aagtacagtg gaaggtggat aacgccctcc aatcgggtaa ctcccaggag agtgtcacag   600
agcaggacag caaggacagc acctacagcc tcagcagcac cctgacgctg agcaaagcag   660
actacgagaa acacaaagtc tacgcctgcg aagtcaccca tcagggcctg agctcgcccg   720
tcacaaagag cttcaacagg ggagagtgtt gactcgag                           758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn His Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
```

```
                    85                  90                  95
Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of anti-
      c-Met antibody (AbF46 orhuAbF46-H1)
```

-continued

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      nti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)

```
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctctg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata ctggtttgc ttactggggc caagggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
```

<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

| | | | | |
|---|---|---|---|---|
| gaattcacta | gtgattaatt | cgccgccacc | atggattcac aggcccaggt | cctcatgttg | 60 |
| ctgctgctat | cggtatctgg | tacctgtgga | gacattttga tgacccagtc | tccatcctcc | 120 |
| ctgactgtgt | cagcaggaga | gaaggtcact | atgagctgca gtccagtca | gagtctttta | 180 |
| gctagtggca | accaaaataa | ctacttggcc | tggcaccagc agaaaccagg | acgatctcct | 240 |
| aaaatgctga | taatttgggc | atccactagg | gtatctggag tccctgatcg | cttcataggc | 300 |
| agtggatctg | ggacggattt | cactctgacc | atcaacagtg tgcaggctga | agatctggct | 360 |
| gtttattact | gtcagcagtc | ctacagcgct | ccgctcacgt tcggtgctgg | gaccaagctg | 420 |
| gagctgaaac | gtacggtggc | tgcaccatct | gtcttcatct tcccgccatc | tgatgagcag | 480 |
| ttgaaatctg | gaactgcctc | tgttgtgtgc | ctgctgaata acttctatcc | cagagaggcc | 540 |
| aaagtacagt | ggaaggtgga | taacgccctc | caatcgggta actcccagga | gagtgtcaca | 600 |
| gagcaggaca | gcaaggacag | cacctacagc | ctcagcagca ccctgacgct | gagcaaagca | 660 |
| gactacgaga | aacacaaagt | ctacgcctgc | gaagtcaccc atcagggcct | gagctcgccc | 720 |
| gtcacaaaga | gcttcaacag | gggagagtgt | tgactcgag | | 759 |

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

| | | | | |
|---|---|---|---|---|
| atgaaggccc | ccgctgtgct | tgcacctggc | atcctcgtgc tcctgtttac | cttggtgcag | 60 |
| aggagcaatg | gggagtgtaa | agaggcacta | gcaaagtccg agatgaatgt | gaatatgaag | 120 |
| tatcagcttc | ccaacttcac | cgcggaaaca | cccatccaga atgtcattct | acatgagcat | 180 |
| cacattttcc | ttggtgccac | taactacatt | tatgttttaa atgaggaaga | ccttcagaag | 240 |
| gttgctgagt | acaagactgg | gcctgtgctg | gaacacccag attgtttccc | atgtcaggac | 300 |
| tgcagcagca | agccaatttt | atcaggaggt | gtttggaaag ataacatcaa | catggctcta | 360 |
| gttgtcgaca | cctactatga | tgatcaactc | attagctgtg gcagcgtcaa | cagagggacc | 420 |
| tgccagcgac | atgtctttcc | ccacaatcat | actgctgaca tacagtcgga | ggttcactgc | 480 |

```
atattctccc cacagataga agagcccagc cagtgtcctg actgtgtggt gagcgccctg      540
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttgacg gaccagtcct acattgatgt tttacctgag       720
ttcagagatt cttaccccat taagtatgtc catgcctttg aaagcaacaa ttttatttac      780
ttcttgacgg tccaaaggga aactctagat gctcagactt tcacacaag aataatcagg      840 ttctgttcca taaactctgg attgcattcc tacatggaaa tgcctctgga gtgtattctc      900
acagaaaaga gaaaaagag atccacaaag aaggaagtgt taatatact tcaggctgcg      960 tatgtcagca agcctggggc ccagcttgct agacaaatag gagccagcct gaatgatgac      1020
attcttttcg gggtgttcgc acaaagcaag ccagattctg ccgaaccaat ggatcgatct      1080
gccatgtgtg cattccctat caaatatgtc aacgacttct caacaagat cgtcaacaaa      1140 aacaatgtga gatgtctcca gcattttac ggacccaatc atgagcactg ctttaatagg       1200
acacttctga gaaattcatc aggctgtgaa gcgcgccgtg atgaatatcg aacagagttt      1260
accacagctt tgcagcgcgt tgacttattc atgggtcaat tcagcgaagt cctcttaaca      1320
tctatatcca ccttcattaa aggagacctc accatagcta atcttgggac atcagagggt      1380
cgcttcatgc aggttgtggt ttctcgatca ggaccatcaa cccctcatgt gaattttctc      1440
ctggactccc atccagtgtc tccagaagtg attgtggagc atacattaaa ccaaaatggc      1500
tacacactgg ttatcactgg gaagaagatc acgaagatcc cattgaatgg cttgggctgc      1560
agacatttcc agtcctgcag tcaatgcctc tctgccccac cctttgttca gtgtggctgg      1620
tgccacgaca aatgtgtgcg atcggaggaa tgcctgagcg ggacatggac tcaacagatc      1680
tgtctgcctg caatctacaa ggttttccca aatagtgcac cccttgaagg agggacaagg      1740
ctgaccatat gtggctggga ctttggattt cggaggaata taaatttga tttaagaaa      1800 actagagttc tccttggaaa tgagagctgc accttgactt aagtgagag cacgatgaat      1860 acattgaaat gcacagttgg tcctgccatg aataagcatt tcaatatgtc cataattatt      1920
tcaaatggcc acgggacaac acaatacagt acattctcct atgtggatcc tgtaataaca      1980
agtatttcgc cgaaatacgg tcctatggct ggtggcactt tacttacttt aactggaaat      2040
tacctaaaca gtgggaattc tagacacatt tcaattggtg gaaaaacatg tactttaaaa      2100
agtgtgtcaa acagtattct tgaatgttat accccagccc aaaccatttc aactgagttt      2160
gctgttaaat tgaaaattga cttagccaac cgagagacaa gcatcttcag ttaccgtgaa      2220
gatcccattg tctatgaaat tcatccaacc aaatcttta ttagtggtgg gagcacaata       2280
acaggtgttg gaaaaaacct gaattcagtt agtgtcccga gaatggtcat aaatgtgcat      2340
gaagcaggaa ggaactttac agtggcatgt caacatcgct ctaattcaga gataatctgt      2400
tgtaccactc cttccctgca acagctgaat ctgcaactcc ccctgaaaac caaagccttt      2460
ttcatgttag atgggatcct ttccaaatac tttgatctca tttatgtaca taatcctgtg      2520
tttaagcctt ttgaaaagcc agtgatgatc tcaatgggca atgaaaatgt actggaaatt      2580
aagggaaatg atattgaccc tgaagcagtt aaaggtgaag tgttaaaagt tggaaataag      2640
agctgtgaga atatacactt acattctgaa gccgttttat gcacggtccc caatgacctg      2700
ctgaaattga acagcgagct aaatatagag tggaagcaag caatttcttc aaccgtcctt      2760
ggaaaagtaa tagttcaacc agatcagaat ttcacaggat tgattgctgg tgttgtctca      2820
```

| | | |
|---|---|---|
| atatcaacag cactgttatt actacttggg tttttcctgt ggctgaaaaa gagaaagcaa | 2880 | |
| attaaagatc tgggcagtga attagttcgc tacgatgcaa gagtacacac tcctcatttg | 2940 | |
| gataggcttg taagtgcccg aagtgtaagc ccaactacag aaatggtttc aaatgaatct | 3000 | |
| gtagactacc gagctacttt tccagaagat cagtttccta attcatctca gaacggttca | 3060 | |
| tgccgacaag tgcagtatcc tctgacagac atgtccccca tcctaactag tggggactct | 3120 | |
| gatatatcca gtccattact gcaaaatact gtccacattg acctcagtgc tctaaatcca | 3180 | |
| gagctggtcc aggcagtgca gcatgtagtg attgggccca gtagcctgat tgtgcatttc | 3240 | |
| aatgaagtca taggaagagg gcattttggt tgtgtatatc atgggacttt gttggacaat | 3300 | |
| gatggcaaga aaattcactg tgctgtgaaa tccttgaaca gaatcactga cataggagaa | 3360 | |
| gtttcccaat ttctgaccga gggaatcatc atgaaagatt ttagtcatcc caatgtcctc | 3420 | |
| tcgctcctgg gaatctgcct gcgaagtgaa gggtctccgc tggtggtcct accatacatg | 3480 | |
| aaacatggag atcttcgaaa tttcattcga aatgagactc ataatccaac tgtaaaagat | 3540 | |
| cttattggct ttggtcttca agtagccaaa ggcatgaaat atcttgcaag caaaaagttt | 3600 | |
| gtccacagag acttggctgc aagaaactgt atgctggatg aaaaattcac agtcaaggtt | 3660 | |
| gctgattttg gtcttgccag agacatgtat gataaagaat actatagtgt acacaacaaa | 3720 | |
| acaggtgcaa agctgccagt gaagtggatg gctttggaaa gtctgcaaac tcaaaagttt | 3780 | |
| accaccaagt cagatgtgtg gtcctttggc gtgctcctct gggagctgat gacaagagga | 3840 | |
| gccccacctt atcctgacgt aaacaccttt gatataactg tttacttgtt gcaagggaga | 3900 | |
| agactcctac aacccgaata ctgcccagac cccttatatg aagtaatgct aaaatgctgg | 3960 | |
| caccctaaag ccgaaatgcg cccatccttt tctgaactgg tgtcccggat atcagcgatc | 4020 | |
| ttctctactt tcattgggga gcactatgtc catgtgaacg ctacttatgt gaacgtaaaa | 4080 | |
| tgtgtcgctc cgtatccttc tctgttgtca tcagaagata acgctgatga tgaggtggac | 4140 | |
| acacgaccag cctccttctg ggagacatca | 4170 | |

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
            130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

```
Glu Glu Cys Leu Ser Gly Thr Trp Thr Gln Gln Ile Cys Leu Pro Ala
 50                  55                  60

Ile Tyr Lys Val Phe Pro Asn Ser Ala Pro Leu Glu Gly Gly Thr Arg
 65                  70                  75                  80

Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450
```

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

```
Val His Phe Asn Glu Val Ile Gly Arg Gly His Phe Gly Cys Val Tyr
  1               5                  10                  15

His Gly Thr Leu Leu Asp Asn Asp Gly Lys Lys Ile His Cys Ala Val
             20                  25                  30

Lys Ser Leu Asn Arg Ile Thr Asp Ile Gly Glu Val Ser Gln Phe Leu
         35                  40                  45

Thr Glu Gly Ile Ile Met Lys Asp Phe Ser His Pro Asn Val Leu Ser
     50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain of c-Met

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtcctttca tctgtaaagg accggttcat caacttcttt     420
gtaggcaata ccataaattc ttcttatttc ccagatcatc cattgcattc gatatcagtg     480
agaaggctaa aggaaacgaa agatggtttt atgtttttga cggaccagtc ctacattgat     540
gttttacctg agttcagaga ttcttacccc attaagtatg tccatgcctt tgaaagcaac     600
aatttttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaaggaagt gtttaatata     780
cttcaggctg cgtatgtcag caagcctggg gcccagcttg ctagacaaat aggagccagc     840
ctgaatgatg acattctttt cggggtgttc gcacaaagca agccagattc tgccgaacca     900
atggatcgat ctgccatgtg tgcattccct atcaaatatg tcaacgactt cttcaacaag     960
atcgtcaaca aaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aaccccctcat    1260
gtgaattttc tcctggactc ccatccagtg tctccagaag tgattgtgga gcatacatta    1320
aaccaaaatg gc                                                        1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca atgtgtgcg atcggaggaa tgcctgagcg ggacatggac tcaacagatc     180
tgtctgcctg caatctacaa ggttttccca aatagtgcac cccttgaagg agggacaagg     240
ctgaccatat gtggctggga ctttggattt cggaggaata taaatttga tttaaagaaa     300
actagagttc tccttggaaa tgagagctgc accttgactt aagtgagag cacgatgaat     360
acattgaaat gcagttgg tcctgccatg aataagcatt caatatgtc cataattatt     420
tcaaatggcc acgggacaac acaatacagt acattctcct atgtggatcc tgtaataaca     480
agtatttcgc cgaaatacgg tcctatggct ggtggcactt tacttacttt aactggaaat     540
tacctaaaca gtgggaattc tagacacatt tcaattggtg gaaaaacatg tactttaaaa     600
```

| | |
|---|---|
| agtgtgtcaa acagtattct tgaatgttat accccagccc aaaccatttc aactgagttt | 660 |
| gctgttaaat tgaaaattga cttagccaac cgagagacaa gcatcttcag ttaccgtgaa | 720 |
| gatcccattg tctatgaaat tcatccaacc aaatctttta ttagtggtgg gagcacaata | 780 |
| acaggtgttg ggaaaaacct gaattcagtt agtgtcccga gaatggtcat aaatgtgcat | 840 |
| gaagcaggaa ggaactttac agtggcatgt caacatcgct ctaattcaga gataatctgt | 900 |
| tgtaccactc cttccctgca acagctgaat ctgcaactcc ccctgaaaac caaagccttt | 960 |
| ttcatgttag atgggatcct ttccaaatac tttgatctca tttatgtaca taatcctgtg | 1020 |
| tttaagcctt ttgaaaagcc agtgatgatc tcaatgggca atgaaaatgt actggaaatt | 1080 |
| aagggaaatg atattgaccc tgaagcagtt aaaggtgaag tgttaaaagt tggaaataag | 1140 |
| agctgtgaga atatacactt acattctgaa gccgttttat gcacggtccc caatgacctg | 1200 |
| ctgaaattga acagcgagct aaatatagag tggaagcaag caatttcttc aaccgtcctt | 1260 |
| ggaaaagtaa tagttcaacc agatcagaat ttcacagga | 1299 |

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

| | |
|---|---|
| gtgcatttca atgaagtcat aggaagaggg cattttggtt gtgtatatca tgggactttg | 60 |
| ttggacaatg atggcaagaa aattcactgt gctgtgaaat ccttgaacag aatcactgac | 120 |
| ataggagaag tttcccaatt tctgaccgag ggaatcatca tgaaagattt tagtcatccc | 180 |
| aatgtcctct cgctcctggg aatctgcctg cgaagtgaag ggtctccgct ggtggtccta | 240 |
| ccatacatga acatggaga tcttcgaaat tcattcgaa atgagactca taatccaact | 300 |
| gtaaaagatc ttattggctt tggtcttcaa gtagccaaag gcatgaaata tcttgcaagc | 360 |
| aaaaagtttg tccacagaga cttggctgca agaaactgta tgctggatga aaaattcaca | 420 |
| gtcaaggttg ctgattttgg tcttgccaga gacatgtatg ataaagaata ctatagtgta | 480 |
| cacaacaaaa caggtgcaaa gctgccagtg aagtggatgg ctttggaaag tctgcaaact | 540 |
| caaaagttta ccaccaagtc agatgtgtgg tcctttggcg tgctcctctg ggagctgatg | 600 |
| acaagaggag ccccacctta tcctgacgta aacacctttg atataactgt ttacttgttg | 660 |
| caagggagaa gactcctaca acccgaatac tgcccagacc ccttatatga agtaatgcta | 720 |
| aaatgctggc accctaaagc cgaaatgcgc ccatcctttt ctgaactggt gtcccggata | 780 |
| tcagcgatct tctctacttt cattggggag cactatgtcc atgtgaacgc tacttatgtg | 840 |
| aacgtaaaat gtgtcgctcc gtatccttct ctgttgtcat cagaagataa cgctgatgat | 900 |
| gaggtggaca cacgaccagc ctccttctgg gagacatca | 939 |

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

Asp Asn Trp Phe Ala Tyr Trp Gly Gln Gly Thr Leu Val

```
                           1               5                  10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95
```

```
Ser Tyr Ser Ala Pro Leu Thr Phe Gly Ala Gly Thr Lys Leu Glu Leu
                100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
```

```
                65                  70                  75                  80
Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                    85                  90                  95

Tyr Cys Ala Arg Asp Asn Trp Phe Ala Tyr Trp Gly Gln Gly Thr Leu
                100                 105                 110

Val Thr Val Ser Ser
        115
```

```
<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
```

```
                1               5                   10                  15
        Asp Arg Val Thr Met Thr Cys Lys Ser Ser Gln Ser Leu Leu Ala Ser
                            20                  25                  30

Gly Asn Gln Asn Asn Tyr Leu Ala Trp His Gln Gln Lys Pro Gly Lys
                        35                  40                  45

Ala Pro Lys Met Leu Ile Ile Trp Ala Ser Thr Arg Val Ser Gly Val
                    50                  55                  60

Pro Asp Arg Phe Ile Gly Ser Gly Ser Gly Thr Asp Phe Thr Leu Thr
        65                  70                  75                  80

Ile Ser Ser Leu Gln Ala Glu Asp Val Ala Val Tyr Tyr Cys Gln Gln
                            85                  90                  95

Ser Tyr Ser Ala Pro Leu Thr Phe Gly Gln Gly Thr Lys Leu Glu Ile
                        100                 105                 110

Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

```
        Asp Ile Leu Met Thr Gln Ser Pro Ser Ser Leu Ser Ala Ser Val Gly
        1               5                   10                  15

Asp Arg Val Thr Ile Thr Cys Lys Ser Ser Gln Ser Leu Leu Ala Ser
                            20                  25                  30

Gly Asn Gln Asn Asn Tyr Leu Ala Trp His Gln Gln Lys Pro Gly Lys
                        35                  40                  45

Ala Pro Lys Met Leu Ile Ile Trp Ala Ser Thr Arg Val Ser Gly Val
                    50                  55                  60

Pro Asp Arg Phe Ile Gly Ser Gly Ser Gly Thr Asp Phe Thr Leu Thr
        65                  70                  75                  80

Ile Ser Ser Leu Gln Ala Glu Asp Val Ala Val Tyr Tyr Cys Gln Gln
                            85                  90                  95

Ser Tyr Ser Ala Pro Leu Thr Phe Gly Gln Gly Thr Lys Leu Glu Ile
                        100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

```
        Asp Ile Gln Met Thr Gln Ser Pro Ser Ser Leu Ser Ala Ser Val Gly
        1               5                   10                  15

Asp Arg Val Thr Ile Thr Cys Lys Ser Ser Gln Ser Leu Leu Ala Ser
                            20                  25                  30

Gly Asn Gln Asn Asn Tyr Leu Ala Trp His Gln Gln Lys Pro Gly Lys
                        35                  40                  45

Ala Pro Lys Met Leu Ile Ile Trp Ala Ser Thr Arg Val Ser Gly Val
                    50                  55                  60

Pro Asp Arg Phe Ile Gly Ser Gly Ser Gly Thr Asp Phe Thr Leu Thr
        65                  70                  75                  80
```

```
Ile Ser Ser Leu Gln Ala Glu Asp Val Ala Val Tyr Tyr Cys Gln Gln
            85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
```

```
<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60
```

```
Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Trp
                 20                  25                  30

Gly Asn Gln Asn Asn Tyr Leu Ala Trp Tyr Gln Gln Lys Pro Gly Lys
             35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 3677
<212> TYPE: DNA
<213> ORGANISM: Artificial Sequence
<220> FEATURE:
<223> OTHER INFORMATION: Synthetic VEGF (NM_001025366.2)
<220> FEATURE:
<221> NAME/KEY: misc_feature
<222> LOCATION: (499)..(1737)
<223> OTHER INFORMATION: CDS

<400> SEQUENCE: 109
tcgcggaggc ttggggcagc cgggtagctc ggaggtcgtg cgctgggggg ctagcaccag      60
```

```
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180 cattttttt taaaactgta ttgtttctcg ttttaattta ttttgcttg ccattcccca      240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag ggcaaagtg     420 agtgacctgc tttggggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggggctc gcggcgtcgc actgaaactt    660
ttcgtccaac ttctgggctg ttctcgcttc ggaggagccg tggtccgcgc gggggaagcc    720
gagccgagcg gagccgcgag aagtgctagc tcgggccggg aggagccgca gccggaggag    780
ggggaggagg aagaagagaa ggaagaggag aggggccgc agtggcgact cggcgctcgg     840
aagccgggct catggacggg tgaggcgcg gtgtgcgcag acagtgctcc agccgcgcgc     900
gctccccagg ccctggcccg ggcctcgggc cggggaggaa gagtagctcg ccgaggcgcc    960
gaggagagcg ggccgccccca gcccgagcc ggagagggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa aaaatcagtt cgaggaaagg gaaaggggca aaaacgaaag   1500
cgcaagaaat cccggtataa gtcctggagc gtgtacgttg gtgcccgctg ctgtctaatg   1560
ccctggagcc tccctggccc ccatccctgt gggccttgct cagagcgag aaagcatttg    1620 tttgtacaag atccgcagac gtgtaaatgt tcctgcaaaa acacagactc gcgttgcaag   1680
gcgaggcagc ttgagttaaa cgaacgtact tgcagatgtg acaagccgag gcggtgagcc   1740
gggcaggagg aaggagcctc cctcagggtt tcgggaacca gatctctcac caggaaagac   1800
tgatacagaa cgatcgatac agaaaccacg ctgccgccac cacaccatca ccatcgacag   1860
aacagtcctt aatccagaaa cctgaaatga aggaagagga gactctgcgc agagcacttt   1920
gggtccggag ggcgagactc cggcggaagc attcccgggc gggtgaccca gcacggtccc   1980
tcttggaatt ggattcgcca tttattttt cttgctgcta aatcaccgag cccggaagat    2040
tagagagttt tatttctggg attcctgtag acacacccac ccacatacat acatttatat   2100
atatatatat tatatatata taaaaataaa tatctctatt ttatatatat aaaatatata   2160
tattcttttt ttaaattaac agtgctaatg ttattggtgt cttcactgga tgtatttgac   2220
tgctgtggac ttgagttggg aggggaatgt tcccactcag atcctgacag ggaagaggag   2280
gagatgagag actctggcat gatctttttt ttgtcccact tggtggggcc agggtcctct   2340
cccctgccca ggaatgtgca aggccagggc atggggcaa atatgaccca gttttgggaa    2400
```

| | |
|---|---|
| caccgacaaa cccagccctg gcgctgagcc tctctacccc aggtcagacg gacagaaaga | 2460 |
| cagatcacag gtacagggat gaggacaccg gctctgacca ggagtttggg gagcttcagg | 2520 |
| acattgctgt gctttgggga ttccctccac atgctgcacg cgcatctcgc ccccagggc | 2580 |
| actgcctgga agattcagga gcctgggcgg ccttcgctta ctctcacctg cttctgagtt | 2640 |
| gcccaggaga ccactggcag atgtcccggc gaagagaaga gacacattgt tggaagaagc | 2700 |
| agcccatgac agctcccctt cctgggactc gccctcatcc tcttcctgct cccttcctg | 2760 |
| gggtgcagcc taaaaggacc tatgtcctca caccattgaa accactagtt ctgtccccc | 2820 |
| aggagacctg gttgtgtgtg tgtgagtggt tgaccttcct ccatccctg gtccttccct | 2880 |
| tcccttcccg aggcacagag agacagggca ggatccacgt gcccattgtg gaggcagaga | 2940 |
| aaagagaaag tgttttatat acggtactta tttaatatcc ctttttaatt agaaattaaa | 3000 |
| acagttaatt taattaaaga gtagggtttt ttttcagtat tcttggttaa tatttaattt | 3060 |
| caactattta tgagatgtat cttttgctct ctcttgctct cttatttgta ccggtttttg | 3120 |
| tatataaaat tcatgtttcc aatctctctc tccctgatcg gtgacagtca ctagcttatc | 3180 |
| ttgaacagat atttaatttt gctaacactc agctctgccc tccccgatcc cctggctccc | 3240 |
| cagcacacat tcctttgaaa taaggtttca atatacatct acatactata tatatatttg | 3300 |
| gcaacttgta tttgtgtgta tatatatata tatgtttta tgtatatatg tgattctgat | 3360 |
| aaaatagaca ttgctattct gttttttata tgtaaaaaca aaacaagaaa aatagagaa | 3420 |
| ttctacatac taaatctctc tccttttta atttaatat ttgttatcat ttatttattg | 3480 |
| gtgctactgt ttatccgtaa taattgtggg gaaaagatat taacatcacg tctttgtctc | 3540 |
| tagtgcagtt tttcgagata ttccgtagta catatttatt tttaaacaac gacaaagaaa | 3600 |
| tacagatata tcttaaaaaa aaaaaagcat tttgtattaa agaatttaat tctgatctca | 3660 |
| aaaaaaaaaa aaaaaaa | 3677 |

<210> SEQ ID NO 110
<211> LENGTH: 3608
<212> TYPE: DNA
<213> ORGANISM: Artificial Sequence
<220> FEATURE:
<223> OTHER INFORMATION: Synthetic VEGF (NM_001025367.2)
<220> FEATURE:
<221> NAME/KEY: misc_feature
<222> LOCATION: (499)..(1668)
<223> OTHER INFORMATION: CDS

<400> SEQUENCE: 110

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg tttaattta ttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacgggt cagagagagc gcgcgggcgt gcgagcagcg aaagcgacag gggcaaagtg | 420 |
| agtgacctgc tttggggt gaccgccgga gcgcggcgtg agccctcccc cttgggatcc | 480 |
| cgcagctgac cagtcgcgct gacggacaga cagacagaca ccgccccag ccccagctac | 540 |
| cacctcctcc ccggcggcg gcggacagtg gacgcggcgg cgagccgcgg gcaggggccg | 600 |
| gagcccgcgc ccggaggcgg ggtggagggg gtcggggctc gcggcgtcgc actgaaactt | 660 |

```
ttcgtccaac ttctgggctg ttctcgcttc ggaggagccg tggtccgcgc gggggaagcc    720
gagccgagcg gagccgcgag aagtgctagc tcgggccggg aggagccgca gccggaggag    780
ggggaggagg aagaagagaa ggaagaggag aggggccgc agtggcgact cggcgctcgg     840
aagccgggct catggacggg tgaggcggcg tgtgcgcag acagtgctcc agccgcgcgc     900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccgtccctg tgggccttgc tcagagcgga gaaagcattt gtttgtacaa    1560
gatccgcaga cgtgtaaatg ttcctgcaaa aacacagact cgcgttgcaa ggcgaggcag    1620
cttgagttaa acgaacgtac ttgcagatgt gacaagccga ggcggtgagc cgggcaggag    1680
gaaggagcct ccctcagggt ttcgggaacc agatctctca ccaggaaaga ctgatacaga    1740
acgatcgata cagaaaccac gctgccgcca ccacaccatc accatcgaca gaacagtcct    1800
taatccagaa acctgaaatg aaggaagagg agactctgcg cagagcactt tgggtccgga    1860
gggcgagact ccggcggaag cattcccggg cgggtgaccc agcacggtcc ctcttggaat    1920
tggattcgcc attttatttt tcttgctgct aaatcaccga gcccggaaga ttagagagtt    1980
ttatttctgg gattcctgta gacacaccca cccacataca tacatttata tatatatata    2040
ttatatatat ataaaaataa atatctctat tttatatata taaaatatat atattctttt    2100
tttaaattaa cagtgctaat gttattggtg tcttcactgg atgtatttga ctgctgtgga    2160
cttgagttgg gaggggaatg ttcccactca gatcctgaca gggaagagga ggagatgaga    2220
gactctggca tgatcttttt tttgtccac ttggtgggc agggtcctc tcccctgccc       2280 aggaatgtgc aaggccaggg catggggca aatatgaccc agttttggga acaccgacaa     2340
acccagcccc ggcgctgagc ctctctaccc caggtcagac ggacagaaag acagatcaca    2400
ggtacaggga tgaggacacc ggctctgacc aggagtttgg ggagcttcag gacattgctg    2460
tgctttgggg attccctcca catgctgcac gcgcatctcg cccccagggg cactgcctgg    2520
aagattcagg agcctgggcg gccttcgctt actctcacct gcttctgagt tgcccaggag    2580
accactggca gatgtcccgg cgaagagaag agacacattg ttggaagaag cagcccatga    2640
cagctcccct tcctgggact cgccctcatc ctcttcctgc tccccttcct ggggtgcagc    2700
ctaaaaggac ctatgtcctc acaccattga aaccactagt tctgtccccc caggagacct    2760
ggttgtgtgt gtgtgagtgg ttgaccttcc tccatcccct ggtccttccc ttcccttccc    2820
gaggcacaga gagacagggc aggatccacg tgcccattgt ggaggcagag aaaagagaaa    2880 gtgtttata tacggtactt atttaatatc ccttttaat tagaaattaa aacagttaat      2940
ttaattaaag agtagggttt tttttcagta ttccttggtta atatttaatt tcaactatt    3000
```

-continued

| | |
|---|---|
| atgagatgta tcttttgctc tctcttgctc tcttatttgt accggttttt gtatataaaa | 3060 |
| ttcatgtttc caatctctct ctccctgatc ggtgacagtc actagcttat cttgaacaga | 3120 |
| tatttaattt tgctaacact cagctctgcc ctccccgatc ccctggctcc ccagcacaca | 3180 |
| ttcctttgaa ataaggtttc aatatacatc tacatactat atatatattt ggcaacttgt | 3240 |
| atttgtgtgt atatatatat atatatgttt atgtatatat gtgattctga taaaatagac | 3300 |
| attgctattc tgtttttat atgtaaaaac aaaacaagaa aaaatagaga attctacata | 3360 |
| ctaaatctct ctccttttt aattttaata tttgttatca tttatttatt ggtgctactg | 3420 |
| tttatccgta ataattgtgg ggaaaagata ttaacatcac gtctttgtct ctagtgcagt | 3480 |
| ttttcgagat attccgtagt acatatttat ttttaaacaa cgacaaagaa atacagatat | 3540 |
| atcttaaaaa aaaaaagca ttttgtatta aagaatttaa ttctgatctc aaaaaaaaa | 3600 |
| aaaaaaaa | 3608 |

<210> SEQ ID NO 111
<211> LENGTH: 3554
<212> TYPE: DNA
<213> ORGANISM: Artificial Sequence
<220> FEATURE:
<223> OTHER INFORMATION: Synthetic VEGF (NM_001025368.2)
<220> FEATURE:
<221> NAME/KEY: misc_feature
<222> LOCATION: (499)..(1614)
<223> OTHER INFORMATION: CDS

<400> SEQUENCE: 111

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag ggcaaagtg | 420 |
| agtgacctgc ttttggggt gaccgccgga gcgcggcgtg agccctcccc cttgggatcc | 480 |
| cgcagctgac cagtcgcgct gacggacaga cagacagaca ccgcccccag cccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc gggggaagcc | 720 |
| gagccgagcg gagccgcgag aagtgctagc tcgggccggg aggagccgca gccgaggag | 780 |
| ggggaggagg aagaagagaa ggaagaggag agggggccgc agtggcgact cggcgctcgg | 840 |
| aagccgggct catggacggg tgaggcgcg gtgtgcgcag acagtgctcc agccgcgcgc | 900 |
| gctcccagg ccctggcccg ggcctcgggc cggggaggaa gagtagctcg ccgaggcgcc | 960 |
| gaggagagcg ggccgcccca cagcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag tacccctgatg agatcgagta catcttcaag | 1260 |
| ccatcctgtg tgcccctgat gcgatgcggg ggctgctgca atgacgaggg cctggagtgt | 1320 |

```
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa tccctgtggg ccttgctcag agcggagaaa gcatttgttt    1500
gtacaagatc cgcagacgtg taaatgttcc tgcaaaaaca cagactcgcg ttgcaaggcg    1560
aggcagcttg agttaaacga acgtacttgc agatgtgaca agccgaggcg gtgagccggg    1620
caggaggaag gagcctccct cagggtttcg ggaaccagat ctctcaccag gaaagactga    1680
tacagaacga tcgatacaga aaccacgctg ccgccaccac accatcacca tcgacagaac    1740
agtccttaat ccagaaacct gaaatgaagg aagaggagac tctgcgcaga gcactttggg    1800
tccggagggc gagactccgg cggaagcatt cccgggcggg tgacccagca cggtccctct    1860
tggaattgga ttcgccattt tattttctt gctgctaaat caccgagccc ggaagattag    1920
agagttttat ttctgggatt cctgtagaca cacccaccca catacataca tttatatata    1980
tatatattat atatatataa aaataaatat ctctatttta tatataaaa atatatatat    2040 tcttttttta aattaacagt gctaatgtta ttggtgtctt cactggatgt atttgactgc    2100
tgtggacttg agttgggagg ggaatgttcc cactcagatc ctgacaggga agaggaggag    2160
atgagagact ctggcatgat cttttttttg tcccacttgg tggggccagg gtcctctccc    2220
ctgcccagga atgtgcaagg ccagggcatg ggggcaaata tgacccagtt ttgggaacac    2280
cgacaaaccc agccctggcg ctgagcctct ctaccccagg tcagacggac agaaagacag    2340
atcacaggta cagggatgag gacaccggct ctgaccagga gtttgggag cttcaggaca    2400 ttgctgtgct ttggggattc cctccacatg ctgcacgcgc atctcgcccc cagggcact    2460 gcctggaaga ttcaggagcc tgggcggcct tcgcttactc tcacctgctt ctgagttgcc    2520
caggagacca ctggcagatg tcccggcgaa gagaagagac acattgttgg aagaagcagc    2580
ccatgacagc tcccttcct gggactcgcc ctcatcctct tcctgctccc cttcctgggg    2640
tgcagcctaa aaggacctat gtcctcacac cattgaaacc actagttctg tcccccagg    2700 agacctggtt gtgtgtgtgt gagtggttga ccttcctcca tccccctggtc cttcccttcc    2760 cttcccgagg cacagagaga cagggcagga tccacgtgcc cattgtggag gcagagaaaa    2820
gagaaagtgt tttatatacg gtacttattt aatatccctt tttaattaga aattaaaaca    2880
gttaatttaa ttaaagagta gggttttttt tcagtattct tggttaatat ttaatttcaa    2940
ctatttatga gatgtatctt ttgctctctc ttgctctctt atttgtaccg gttttgtat    3000 ataaaattca tgtttccaat ctctctctcc ctgatcggtg acagtcacta gcttatcttg    3060
aacagatatt taattttgct aacactcagc tctgccctcc ccgatcccct ggctccccag    3120
cacacattcc tttgaaataa ggtttcaata tacatctaca tactatatat atatttggca    3180 acttgtatt gtgtgtatat atatatatat atgtttatgt atatatgtga ttctgataaa    3240
atagacattg ctattctgtt ttttatatgt aaaaacaaaa caagaaaaaa tagagaattc    3300
tacatactaa atctctctcc ttttttaatt ttaatatttg ttatcattta tttattggtg    3360
ctactgttta tccgtaataa ttgtgggaa aagatattaa catcacgtct ttgtctctag    3420
tgcagttttt cgagatattc cgtagtacat atttatttt aaacaacgac aaagaaatac    3480
agatatatct taaaaaaaa aaagcatttt gtattaaaga atttaattct gatctcaaaa    3540
aaaaaaaaaa aaaa                                                     3554

<210> SEQ ID NO 112
```

```
<211> LENGTH: 3519
<212> TYPE: DNA
<213> ORGANISM: Artificial Sequence
<220> FEATURE:
<223> OTHER INFORMATION: Synthetic VEGF (NM_001025369.2)
<220> FEATURE:
<221> NAME/KEY: misc_feature
<222> LOCATION: (499)..(1563)
<223> OTHER INFORMATION: CDS

<400> SEQUENCE: 112
```

| | | | | | |
|---|---|---|---|---|---|
| tcgcggaggc | ttggggcagc | cgggtagctc | ggaggtcgtg | gcgctggggg | ctagcaccag | 60 |
| cgctctgtcg | ggaggcgcag | cggttaggtg | gaccggtcag | cggactcacc | ggccagggcg | 120 |
| ctcggtgctg | gaatttgata | ttcattgatc | cgggttttat | ccctcttctt | ttttcttaaa | 180 |
| cattttttt | taaaactgta | ttgtttctcg | ttttaattta | tttttgcttg | ccattcccca | 240 |
| cttgaatcgg | gccgacggct | ggggagatt | gctctacttc | cccaaatcac | tgtggatttt | 300 |
| ggaaaccagc | agaaagagga | aagaggtagc | aagagctcca | gagagaagtc | gaggaagaga | 360 |
| gagacggggt | cagagagagc | gcgcgggcgt | gcgagcagcg | aaagcgacag | ggcaaagtg | 420 |
| agtgacctgc | ttttgggggt | gaccgccgga | gcgcggcgtg | agccctcccc | cttgggatcc | 480 |
| cgcagctgac | cagtcgcgct | gacggacaga | cagacagaca | ccgccccag | ccccagctac | 540 |
| cacctcctcc | ccggccggcg | gcggacagtg | gacgcggcgg | cgagccgcgg | gcaggggccg | 600 |
| gagcccgcgc | ccggaggcgg | ggtggagggg | gtcgggctc | gcggcgtcgc | actgaaactt | 660 |
| ttcgtccaac | ttctgggctg | ttctcgcttc | ggaggagccg | tggtccgcgc | ggggaagcc | 720 |
| gagccgagcg | gagccgcgag | aagtgctagc | tcgggccggg | aggagccgca | gccgaggag | 780 |
| ggggaggagg | aagaagagaa | ggaagaggag | aggggccgc | agtggcgact | cggcgctcgg | 840 |
| aagccgggct | catggacggg | tgaggcgcg | gtgtgcgcag | acagtgctcc | agccgcgcgc | 900 |
| gctcccagg | ccctggcccg | ggcctcgggc | cggggaggaa | gagtagctcg | ccgaggcgcc | 960 |
| gaggagagcg | ggccgcccca | cagcccgagc | cggagaggga | gcgcgagccg | cgccggcccc | 1020 |
| ggtcgggcct | ccgaaaccat | gaactttctg | ctgtcttggg | tgcattggag | ccttgccttg | 1080 |
| ctgctctacc | tccaccatgc | caagtggtcc | caggctgcac | ccatggcaga | aggaggaggg | 1140 |
| cagaatcatc | acgaagtggt | gaagttcatg | gatgtctatc | agcgcagcta | ctgccatcca | 1200 |
| atcgagaccc | tggtggacat | cttccaggag | taccctgatg | agatcgagta | catcttcaag | 1260 |
| ccatcctgtg | tgcccctgat | gcgatgcggg | ggctgctgca | atgacgaggg | cctggagtgt | 1320 |
| gtgcccactg | aggagtccaa | catcaccatg | cagattatgc | ggatcaaacc | tcaccaaggc | 1380 |
| cagcacatag | gagagatgag | cttcctacag | cacaacaaat | gtgaatgcag | accaaagaaa | 1440 |
| gatagagcaa | gacaagaaaa | tccctgtggg | ccttgctcag | agcggagaaa | gcatttgttt | 1500 |
| gtacaagatc | cgcagacgtg | taaatgttcc | tgcaaaaaca | cagactcgcg | ttgcaagatg | 1560 |
| tgacaagccg | aggcggtgag | ccgggcagga | ggaaggagcc | tccctcaggg | tttcgggaac | 1620 |
| cagatctctc | accaggaaag | actgatacag | aacgatcgat | acagaaacca | cgctgccgcc | 1680 |
| accacaccat | caccatcgac | agaacagtcc | ttaatccaga | aacctgaaat | gaaggaagag | 1740 |
| gagactctgc | gcagagcact | ttgggtccgg | agggcgagac | tccggcggaa | gcattcccgg | 1800 |
| gcgggtgacc | cagcacggtc | cctcttggaa | ttggattcgc | cattttattt | ttcttgctgc | 1860 |
| taaatcaccg | agcccggaag | attagagagt | tttatttctg | ggattcctgt | agacacaccc | 1920 |
| acccacatac | atacatttat | atatatatat | attatatata | tataaaaata | aatatctcta | 1980 |
| ttttatatat | ataaaatata | tatattcttt | ttttaaatta | acagtgctaa | tgttattggt | 2040 |

```
gtcttcactg gatgtatttg actgctgtgg acttgagttg ggaggggaat gttcccactc    2100
agatcctgac agggaagagg aggagatgag agactctggc atgatctttt ttttgtccca    2160
cttggtgggg ccagggtcct ctcccctgcc caggaatgtg caaggccagg catgggggc    2220 aaatatgacc cagttttggg aacaccgaca aacccagccc tggcgctgag cctctctacc    2280
ccaggtcaga cggacagaaa gacagatcac aggtacaggg atgaggacac cggctctgac    2340
caggagtttg gggagcttca ggacattgct gtgctttggg gattccctcc acatgctgca    2400
cgcgcatctc gccccagg gcactgcctg aagattcag agcctgggc ggccttcgct    2460 tactctcacc tgcttctgag ttgcccagga ccactggc agatgtcccg gcgaagagaa    2520
gagacacatt gttggaagaa gcagcccatg acagctcccc ttcctgggac tcgccctcat    2580
cctcttcctg ctcccttcc tggggtgcag cctaaaagga cctatgtcct cacaccattg    2640
aaaccactag ttctgtcccc ccaggagacc tggttgtgtg tgtgtgagtg gttgaccttc    2700
ctccatcccc tggtccttcc cttcccttcc cgaggcacag agagacaggg caggatccac    2760
gtgcccattg tggaggcaga gaaaagagaa agtgttttat atacggtact tatttaatat    2820
ccctttttaa ttagaaatta aaacagttaa tttaattaaa gagtagggtt ttttttcagt    2880
attcttggtt aatatttaat ttcaactatt tatgagatgt atcttttgct ctctcttgct    2940
ctcttatttg taccggtttt tgtatataaa attcatgttt ccaatctctc tctccctgat    3000
cggtgacagt cactagctta tcttgaacag atatttaatt ttgctaacac tcagctctgc    3060
cctccccgat cccctggctc cccagcacac attcctttga aataaggttt caatatacat    3120
ctacatacta tatatatatt tggcaacttg tatttgtgtg tatatatata tatatatgtt    3180
tatgtatata tgtgattctg ataaaataga cattgctatt ctgttttta tatgtaaaaa    3240 caaaacaaga aaaaatagag aattctacat actaaatctc tctccttttt taattttaat    3300
atttgttatc atttatttat tggtgctact gtttatccgt aataattgtg gggaaaagat    3360
attaacatca cgtctttgtc tctagtgcag ttttttcgaga tattccgtag tacatatttta    3420 tttttaaaca acgacaaaga aatacagata tatcttaaaa aaaaaaaagc attttgtatt    3480
aaagaattta attctgatct caaaaaaaaa aaaaaaaa                             3519
```

<210> SEQ ID NO 113
<211> LENGTH: 3422
<212> TYPE: DNA
<213> ORGANISM: Artificial Sequence
<220> FEATURE:
<223> OTHER INFORMATION: Synthetic VEGF (NM_001025370.2)
<220> FEATURE:
<221> NAME/KEY: misc_feature
<222> LOCATION: (499)..(1482)
<223> OTHER INFORMATION: CDS

<400> SEQUENCE: 113

```
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
```

```
agtgacctgc tttrggggt gaccgccgga gcgcgcgtg agccctcccc cttgggatcc        480
cgcagctgac cagtcgcgct gacggacaga cagacagaca ccgcccccag ccccagctac       540
cacctcctcc ccggccggcg gcggacagtg gacgcggcgg cgagccgcgg gcaggggccg       600
gagcccgcgc ccggaggcgg ggtggagggg gtcggggctc gcggcgtcgc actgaaactt       660
ttcgtccaac ttctgggctg ttctcgcttc ggaggagccg tggtccgcgc ggggggaagcc      720
gagccgagcg gagccgcgag aagtgctagc tcgggccggg aggagccgca gccgaggag        780
ggggaggagg aagaagagaa ggaagaggag aggggccgc agtggcgact cggcgctcgg        840
aagccgggct catggacggg tgaggcgcg gtgtgcgcag acagtgctcc agccgcgcgc        900
gctccccagg ccctggcccg ggcctcgggc cggggaggaa gagtagctcg ccgaggcgcc       960
gaggagagcg ggccgcccca cagcccgagc cggagaggga gcgcgagccg cgccggcccc      1020
ggtcgggcct ccgaaaccat gaactttctg ctgtcttggg tgcattggag ccttgccttg      1080
ctgctctacc tccaccatgc caagtggtcc caggctgcac ccatggcaga aggaggaggg      1140
cagaatcatc acgaagtggt gaagttcatg gatgtctatc agcgcagcta ctgccatcca      1200
atcgagaccc tggtggacat cttccaggag taccctgatg agatcgagta catcttcaag      1260
ccatcctgtg tgcccctgat gcgatgcggg ggctgctgca atgacgaggg cctggagtgt      1320
gtgcccactg aggagtccaa catcaccatg cagattatgc ggatcaaacc tcaccaaggc      1380
cagcacatag gagagatgag cttcctacag cacaacaaat gtgaatgcag accaaagaaa      1440
gatagagcaa gacaagaaaa atgtgacaag ccgaggcggt gagccgggca ggaggaagga      1500
gcctccctca gggtttcggg aaccagatct ctcaccagga aagactgata cagaacgatc      1560
gatacagaaa ccacgctgcc gccaccacac catcaccatc gacagaacag tccttaatcc      1620
agaaacctga aatgaaggaa gaggagactc tgcgcagagc actttgggtc cggagggcga      1680
gactccggcg gaagcattcc cggcggggtg acccagcacg gtccctcttg gaattggatt      1740
cgccatttta tttttcttgc tgctaaatca ccgagcccgg aagattagag agttttattt      1800
ctgggattcc tgtagacaca cccacccaca tacatacatt tatatatata tatattatat      1860
atatataaaa ataaatatct ctattttata tatataaaat atatatattc ttttttttaaa     1920
ttaacagtgc taatgttatt ggtgtcttca ctggatgtat ttgactgctg tggacttgag      1980
ttgggagggg aatgttccca ctcagatcct gacaggaag aggaggagat gagagactct       2040
ggcatgatct ttttttttgtc ccacttggtg gggccagggt cctctcccct gcccaggaat     2100
gtgcaaggcc agggcatggg ggcaaatatg acccagtttt gggaacaccg acaaacccag      2160
ccctggcgct gagcctctct accccaggtc agacggacag aaagacagat cacaggtaca      2220
gggatgagga caccggctct gaccaggagt ttggggagct tcaggacatt gctgtgcttt      2280
ggggattccc tccacatgct gcacgcgcat ctcgcccca ggggcactgc ctggaagatt       2340
caggagcctg ggcggccttc gcttactctc acctgcttct gagttgccca ggagaccact      2400
ggcagatgtc ccgcgaaga gaagagacac attgttggaa gaagcagccc atgacagctc      2460
cccttcctgg gactcgccct catcctcttc ctgctcccct tcctggggtg cagcctaaaa      2520
ggacctatgt cctcacacca ttgaaaccac tagttctgtc cccccaggag acctggttgt      2580
gtgtgtgtga gtggttgacc ttcctccatc ccctggtcct tcccttccct tcccgaggca     2640
cagagagaca gggcaggatc cacgtgccca ttgtggaggc agagaaaaga gaaagtgttt      2700
tatatacggt acttatttaa tatcccttt taattagaaa ttaaacagt taatttaatt        2760
aaagagtagg gttttttttc agtattcttg gttaatattt aatttcaact atttatgaga      2820
```

```
tgtatctttt gctctctctt gtctctttat ttgtaccggt ttttgtatat aaaattcatg    2880
tttccaatct ctctctccct gatcggtgac agtcactagc ttatcttgaa cagatattta    2940
attttgctaa cactcagctc tgccctcccc gatcccctgg ctccccagca cacattcctt    3000
tgaaataagg tttcaatata catctacata ctatatatat atttggcaac ttgtatttgt    3060
gtgtatatat atatatatat gtttatgtat atatgtgatt ctgataaaat agacattgct    3120
attctgtttt ttatatgtaa aaacaaaaca agaaaaaata gagaattcta catactaaat    3180
ctctctcctt ttttaatttt aatatttgtt atcatttatt tattggtgct actgtttatc    3240
cgtaataatt gtggggaaaa gatattaaca tcacgtcttt gtctctagtg cagttttcg     3300 agatattccg tagtacatat ttatttttaa acaacgacaa agaaatacag atatatctta    3360
aaaaaaaaaa agcattttgt attaaagaat ttaattctga tctcaaaaaa aaaaaaaaaa    3420
aa                                                                   3422
```

<210> SEQ ID NO 114
<211> LENGTH: 3488
<212> TYPE: DNA
<213> ORGANISM: Artificial Sequence
<220> FEATURE:
<223> OTHER INFORMATION: Synthetic VEGF(NM_001033756.2)
<220> FEATURE:
<221> NAME/KEY: misc_feature
<222> LOCATION: (499)..(1614)
<223> OTHER INFORMATION: CDS

<400> SEQUENCE: 114

```
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
catttttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagca aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggggctc gcggcgtcgc actgaaactt    660
ttcgtccaac ttctgggctg ttctcgcttc ggaggagccg tggtccgcgc ggggaagcc     720 gagccgagcg gagccgcgag aagtgctagc tcggccggg aggagccgca gccggaggag     780
ggggaggagg aagaagagaa ggaagaggag aggggccgc agtggcgact cggcgctcgg     840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
```

```
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa tccctgtggg ccttgctcag agcggagaaa gcatttgttt    1500
gtacaagatc cgcagacgtg taaatgttcc tgcaaaaaca cagactcgcg ttgcaaggcg    1560
aggcagcttg agttaaacga acgtacttgc agatctctca ccaggaaaga ctgatacaga    1620
acgatcgata cagaaaccac gctgccgcca ccacaccatc accatcgaca gaacagtcct    1680
taatccagaa acctgaaatg aaggaagagg agactctgcg cagagcactt tgggtccgga    1740
gggcgagact ccggcggaag cattcccggg cgggtgaccc agcacggtcc ctcttggaat    1800
tggattcgcc atttatttt tcttgctgct aaatcaccga gcccggaaga ttagagagtt    1860
ttatttctgg gattcctgta gacacaccca cccacataca tacatttata tatatatata    1920
ttatatatat ataaaaataa atatctctat tttatatata taaaatatat atattctttt    1980
tttaaattaa cagtgctaat gttattggtg tcttcactgg atgtatttga ctgctgtgga    2040
cttgagttgg gaggggaatg ttcccactca gatcctgaca gggaagagga ggagatgaga    2100
gactctggca tgatcttttt tttgtcccac ttggtgggc cagggtcctc tccctgccc    2160 aggaatgtgc aaggccaggg catggggca aatatgaccc agttttggga acaccgacaa    2220
acccagccct ggcgctgagc ctctctaccc caggtcagac ggacagaaag acagatcaca    2280
ggtacaggga tgaggacacc ggctctgacc aggagtttgg ggagcttcag gacattgctg    2340
tgctttgggg attccctcca catgctgcac gcgcatctcg ccccaggggg cactgcctgg    2400
aagattcagg agcctgggcg gccttcgctt actctcacct gcttctgagt tgcccaggag    2460
accactggca gatgtcccgg cgaagagaag agacacattg ttggaagaag cagcccatga    2520
cagctcccct tcctgggact cgccctcatc ctcttcctgc tcccttcct ggggtgcagc    2580 ctaaaaggac ctatgtcctc acaccattga aaccactagt tctgtccccc caggagacct    2640
ggttgtgtgt gtgtgagtgg ttgaccttcc tccatcccct ggtccttccc ttcccttccc    2700
gaggcacaga gagacagggc aggatccacg tgcccattgt ggaggcagag aaaagagaaa    2760
gtgttttata tacggtactt atttaatatc ccttttttaat tagaaattaa aacagttaat    2820
ttaattaaag agtagggttt tttttcagta ttccttggtta atatttaatt tcaactattt    2880
atgagatgta tcttttgctc tctcttgctc tcttatttgt accggttttt gtatataaaa    2940
ttcatgtttc caatctctct ctccctgatc ggtgacagtc actagcttat cttgaacaga    3000
tatttaattt tgctaacact cagctctgcc ctccccgatc ccctggctcc ccagcacaca    3060
ttcctttgaa ataaggtttc aatatacatc tacatactat atatatattt ggcaacttgt    3120
atttgtgtgt atatatatat atatatgttt atgtatatat gtgattctga taaaatagac    3180
attgctattc tgttttttat atgtaaaaac aaacaagaa aaatagaga attctacata    3240 ctaaatctct ctccttttt aattttaata tttgttatca tttatttatt ggtgctactg    3300
tttatccgta ataattgtgg ggaaaagata ttaacatcac gtctttgtct ctagtgcagt    3360
ttttcgagat attccgtagt acatatttat ttttaaacaa cgacaaagaa atacagatat    3420
atcttaaaaa aaaaaagca ttttgtatta aagaatttaa ttctgatctc aaaaaaaaa    3480 aaaaaaaa                                                            3488
```

<210> SEQ ID NO 115
<211> LENGTH: 3392

```
<212> TYPE: DNA
<213> ORGANISM: Artificial Sequence
<220> FEATURE:
<223> OTHER INFORMATION: Synthetic VEGF(NM_001171622.1)
<220> FEATURE:
<221> NAME/KEY: misc_feature
<222> LOCATION: (499)..(1452)
<223> OTHER INFORMATION: CDS

<400> SEQUENCE: 115
```

| | | | | | |
|---|---|---|---|---|---|
| tcgcggaggc | ttggggcagc | cgggtagctc | ggaggtcgtg | gcgctggggg | ctagcaccag | 60 |
| cgctctgtcg | ggaggcgcag | cggttaggtg | gaccggtcag | cggactcacc | ggccagggcg | 120 |
| ctcggtgctg | gaatttgata | ttcattgatc | cgggttttat | ccctcttctt | ttttcttaaa | 180 |
| cattttttt | taaaactgta | ttgtttctcg | ttttaattta | ttttgcttg | ccattcccca | 240 |
| cttgaatcgg | gccgacggct | tggggagatt | gctctacttc | cccaaatcac | tgtggatttt | 300 |
| ggaaaccagc | agaaagagga | aagaggtagc | aagagctcca | gagagaagtc | gaggaagaga | 360 |
| gagacgggt | cagagagagc | gcgcgggcgt | gcgagcagcg | aaagcgacag | ggcaaagtg | 420 |
| agtgacctgc | ttttgggggt | gaccgccgga | gcgcggcgtg | agccctcccc | cttgggatcc | 480 |
| cgcagctgac | cagtcgcgct | gacggacaga | cagacagaca | ccgcccccag | ccccagctac | 540 |
| cacctcctcc | ccggccggcg | gcggacagtg | gacgcggcgg | cgagccgcgg | gcaggggccg | 600 |
| gagcccgcgc | ccggaggcgg | ggtggagggg | gtcgggctc | gcggcgtcgc | actgaaactt | 660 |
| ttcgtccaac | ttctgggctg | ttctcgcttc | ggaggagccg | tggtccgcgc | ggggaagcc | 720 |
| gagccgagcg | gagccgcgag | aagtgctagc | tcgggccggg | aggagccgca | gccgaggag | 780 |
| ggggaggagg | aagaagagaa | ggaagaggag | aggggccgc | agtggcgact | cggcgctcgg | 840 |
| aagccgggct | catggacggg | tgaggcggcg | gtgtgcgcag | acagtgctcc | agccgcgcgc | 900 |
| gctcccagg | ccctggcccg | ggcctcgggc | cggggaggaa | gagtagctcg | ccgaggcgcc | 960 |
| gaggagagcg | ggccgccccc | cagcccgagc | cggagaggga | gcgcgagccg | cgccggcccc | 1020 |
| ggtcgggcct | ccgaaaccat | gaactttctg | ctgtcttggg | tgcattggag | ccttgccttg | 1080 |
| ctgctctacc | tccaccatgc | caagtggtcc | caggctgcac | ccatggcaga | aggaggaggg | 1140 |
| cagaatcatc | acgaagtggt | gaagttcatg | gatgtctatc | agcgcagcta | ctgccatcca | 1200 |
| atcgagaccc | tggtggacat | cttccaggag | taccctgatg | agatcgagta | catcttcaag | 1260 |
| ccatcctgtg | tgcccctgat | gcgatgcggg | ggctgctgca | atgacgaggg | cctggagtgt | 1320 |
| gtgcccactg | aggagtccaa | catcaccatg | cagattatgc | ggatcaaacc | tcaccaaggc | 1380 |
| cagcacatag | gagagatgag | cttcctacag | cacaacaaat | gtgaatgcag | atgtgacaag | 1440 |
| ccgaggcggt | gagccgggca | ggaggaagga | gcctccctca | gggtttcggg | aaccagatct | 1500 |
| ctcaccagga | aagactgata | cagaacgatc | gatacagaaa | ccacgctgcc | gccaccacac | 1560 |
| catcaccatc | gacagaacag | tccttaatcc | agaaacctga | aatgaaggaa | gaggagactc | 1620 |
| tgcgcagagc | actttgggtc | cggagggcga | gactccggcg | gaagcattcc | cgggcgggtg | 1680 |
| acccagcacg | gtccctcttg | gaattggatt | cgccatttta | tttttcttgc | tgctaaatca | 1740 |
| ccgagcccgg | aagattagag | agttttattt | ctgggattcc | tgtagacaca | cccacccaca | 1800 |
| tacatacatt | tatatatata | tatattatat | atatataaaa | ataaatatct | ctattttata | 1860 |
| tataaaaat | atatatattc | tttttttaaa | ttaacagtgc | taatgttatt | ggtgtcttca | 1920 |
| ctggatgtat | ttgactgctg | tggacttgag | ttggagggg | aatgttccca | ctcagatcct | 1980 |
| gacagggaag | aggaggagat | gagagactct | ggcatgatct | ttttttgtc | ccacttggtg | 2040 |

| | |
|---|---|
| gggccagggt cctctcccct gcccaggaat gtgcaaggcc agggcatggg ggcaaatatg | 2100 |
| acccagtttt gggaacaccg acaaacccag ccctggcgct gagcctctct acccccaggtc | 2160 |
| agacggacag aaagacagat cacaggtaca gggatgagga caccggctct gaccaggagt | 2220 |
| ttggggagct tcaggacatt gctgtgcttt ggggattccc tccacatgct gcacgcgcat | 2280 |
| ctcgccccca ggggcactgc ctggaagatt caggagcctg ggcggccttc gcttactctc | 2340 |
| acctgcttct gagttgccca ggagaccact ggcagatgtc ccggcgaaga aagagacac | 2400 |
| attgttggaa gaagcagccc atgacagctc cccttcctgg gactcgccct catcctcttc | 2460 |
| ctgctcccct cctggggtg cagcctaaaa ggacctatgt cctcacacca ttgaaaccac | 2520 |
| tagttctgtc cccccaggag acctggttgt gtgtgtgtga gtggttgacc ttcctccatc | 2580 |
| ccctggtcct tcccttccct tcccgaggca cagagagaca gggcaggatc cacgtgccca | 2640 |
| tgtggaggc agagaaaaga gaaagtgttt tatatacggt acttatttaa tatcccttt | 2700 |
| taattagaaa ttaaaacagt taatttaatt aaagagtagg gttttttttc agtattcttg | 2760 |
| gttaatattt aatttcaact atttatgaga tgtatctttt gctctctctt gctctcttat | 2820 |
| ttgtaccggt ttttgtatat aaaattcatg tttccaatct ctctctccct gatcggtgac | 2880 |
| agtcactagc ttatcttgaa cagatattta atttgctaa cactcagctc tgccctcccc | 2940 |
| gatcccctgg ctccccagca cacattcctt tgaaataagg tttcaatata catctacata | 3000 |
| ctatatatat atttggcaac ttgtatttgt gtgtatatat atatatatat gtttatgtat | 3060 |
| atatgtgatt ctgataaaat agacattgct attctgtttt ttatatgtaa aaacaaaaca | 3120 |
| agaaaaaata gagaattcta catactaaat ctctctcctt ttttaatttt aatatttgtt | 3180 |
| atcatttatt tattggtgct actgtttatc cgtaataatt gtggggaaaa gatattaaca | 3240 |
| tcacgtcttt gtctctagtg cagttttcg agatattccg tagtacatat ttattttaa | 3300 |
| acaacgacaa agaaatacag atatatctta aaaaaaaaaa agcatttgt attaaagaat | 3360 |
| ttaattctga tctcaaaaaa aaaaaaaaaa aa | 3392 |

<210> SEQ ID NO 116
<211> LENGTH: 3677
<212> TYPE: DNA
<213> ORGANISM: Artificial Sequence
<220> FEATURE:
<223> OTHER INFORMATION: Synthetic VEGF (NM_001171623.1)
<220> FEATURE:
<221> NAME/KEY: misc_feature
<222> LOCATION: (1039)..(1737)
<223> OTHER INFORMATION: CDS

<400> SEQUENCE: 116

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta tttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |

```
gagcccgcgc ccggaggcgg ggtggagggg gtcggggctc gcggcgtcgc actgaaactt      660
ttcgtccaac ttctgggctg ttctcgcttc ggaggagccg tggtccgcgc ggggggaagcc     720 gagccgagcg gagccgcgag aagtgctagc tcgggccggg aggagccgca gccggaggag     780
ggggaggagg aagaagagaa ggaagaggag aggggggccgc agtggcgact cggcgctcgg    840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
gaggagagcg ggccgcccca gcccgagc cggagaggga gcgcgagccg cgccggcccc      1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca   1200
atcgagaccc tggtggacat cttccaggag taccctgatg agatcgagta catcttcaag    1260
ccatcctgtg tgccctgat gcgatgcggg ggctgctgca atgacgaggg cctggagtgt     1320
gtgcccactg aggagtccaa catcaccatg cagattatgc ggatcaaacc tcaccaaggc   1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg gtgcccgctg ctgtctaatg    1560
ccctggagcc tccctggccc ccatccctgt gggccttgct cagagcggag aaagcatttg   1620
tttgtacaag atccgcagac gtgtaaatgt tcctgcaaaa acacagactc gcgttgcaag   1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc   1980
tcttggaatt ggattcgcca ttttatttt cttgctgcta aatcaccgag cccggaagat    2040
tagagagttt tatttctggg attcctgtag acacacccac ccacatacat acatttatat   2100
atatatatat tatatatata taaaaataaa tatctctatt ttatatatat aaaatatata    2160 tattctttt ttaaattaac agtgctaatg ttattggtgt cttcactgga tgtatttgac    2220
tgctgtggac ttgagttggg aggggaatgt tcccactcag atcctgacag ggaagaggag    2280
gagatgagag actctggcat gatctttttt ttgtcccact tggtggggcc agggtcctct    2340
cccctgccca ggaatgtgca aggccagggc atggggcaa atatgaccca gttttgggaa    2400
caccgacaaa cccagccctg gcgctgagcc tctctacccc aggtcagacg gacagaaaga   2460
cagatcacag gtacagggat gaggacaccg gctctgacca ggagtttggg gagcttcagg    2520
acattgctgt gctttgggga ttccctccac atgctgcacg cgcatctcgc ccccagggggc   2580 actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctcccctt cctgggactc gccctcatcc tcttcctgct cccccttcctg    2760 gggtgcagcc taaaaggacc tatgtcctca caccattgaa accactagtt ctgtcccccc    2820
aggagacctg gttgtgtgtg tgtgagtggt tgaccttcct ccatccctg gtccttccct     2880 tcccttcccg aggcacagag agacagggca ggatccacgt gcccattgtg gaggcagaga    2940
```

| | |
|---|---|
| aaagagaaag tgttttatat acggtactta tttaatatcc cttttttaatt agaaattaaa | 3000 |
| acagttaatt taattaaaga gtagggtttt ttttcagtat tcttggttaa tatttaattt | 3060 |
| caactatttta tgagatgtat cttttgctct ctcttgctct cttatttgta ccggttttttg | 3120 |
| tatataaaat tcatgtttcc aatctctctc tccctgatcg gtgacagtca ctagcttatc | 3180 |
| ttgaacagat atttaatttt gctaacactc agctctgccc tccccgatcc cctggctccc | 3240 |
| cagcacacat tcctttgaaa taaggtttca atatacatct acatactata tatatatttg | 3300 |
| gcaacttgta tttgtgtgta tatatatata tatatgttta tgtatatatg tgattctgat | 3360 |
| aaaatagaca ttgctattct gttttttata tgtaaaaaca aaacaagaaa aaatagagaa | 3420 |
| ttctacatac taaatctctc tcctttttta attttaatat ttgttatcat ttatttattg | 3480 |
| gtgctactgt ttatccgtaa taattgtggg gaaaagatat taacatcacg tctttgtctc | 3540 |
| tagtgcagtt tttcgagata ttccgtagta catatttatt tttaaacaac gacaaagaaa | 3600 |
| tacagatata tcttaaaaaa aaaaagcat tttgtattaa agaatttaat tctgatctca | 3660 |
| aaaaaaaaaa aaaaaa | 3677 |

<210> SEQ ID NO 117
<211> LENGTH: 3626
<212> TYPE: DNA
<213> ORGANISM: Artificial Sequence
<220> FEATURE:
<223> OTHER INFORMATION: Synthetic VEGF (NM_001171624.1)
<220> FEATURE:
<221> NAME/KEY: misc_feature
<222> LOCATION: (1039)..(1686)
<223> OTHER INFORMATION: CDS

<400> SEQUENCE: 117

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta ttttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc ggggaagcc | 720 |
| gagccgagcg gagccgcgag aagtgctagc tcgggccggg aggagccgca gccggaggag | 780 |
| ggggaggagg aagaagagaa ggaagaggag agggggccgc agtggcgact cggcgctcgg | 840 |
| aagccgggct catggacggg tgaggcggcg gtgtgcgcag acagtgctcc agccgcgcgc | 900 |
| gctcccagg ccctggcccg ggcctcgggc cgggaggaa gagtagctcg ccgaggcgcc | 960 |
| gaggagagcg ggccgcccca gcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |

```
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa    1440
gatagagcaa gacaagaaaa aaaatcagtt cgaggaaagg gaagggggca aaaacgaaag    1500
cgcaagaaat cccggtataa gtcctggagc gttccctgtg ggccttgctc agagcggaga    1560
aagcatttgt ttgtacaaga tccgcagacg tgtaaatgtt cctgcaaaaa cacagactcg    1620
cgttgcaagg cgaggcagct tgagttaaac gaacgtactt gcagatgtga caagccgagg    1680
cggtgagccg ggcaggagga aggagcctcc ctcagggttt cgggaaccag atctctcacc    1740
aggaaagact gatacagaac gatcgataca gaaaccacgc tgccgccacc acaccatcac    1800
catcgacaga acagtcctta atccagaaac ctgaaatgaa ggaagaggag actctgcgca    1860
gagcactttg ggtccggagg gcgagactcc ggcggaagca ttcccgggcg ggtgacccag    1920
cacggtccct cttggaattg gattcgccat ttttattttc ttgctgctaa atcaccgagc    1980
ccggaagatt agagagtttt atttctggga ttcctgtaga cacacccacc cacatacata    2040
catttatata tatatatatt atatatatat aaaaataaat atctctattt tatatatata    2100
aaatatatat attcttttttt taaattaaca gtgctaatgt tattggtgtc ttcactggat    2160
gtatttgact gctgtggact tgagttggga ggggaatgtt cccactcaga tcctgacagg    2220
gaagaggagg agatgagaga ctctggcatg atcttttttt tgtcccactt ggtggggcca    2280
gggtcctctc ccctgcccag gaatgtgcaa ggccagggca tgggggcaaa tatgacccag    2340
ttttgggaac accgacaaac ccagccctgg cgctgagcct ctctacccca ggtcagacgg    2400
acagaaagac agatcacagg tacagggatg aggacaccgg ctctgaccag gagtttgggg    2460
agcttcagga cattgctgtg cttttgggat tccctccaca tgctgcacgc gcatctcgcc    2520
cccaggggca ctgcctggaa gattcaggag cctgggcggc cttcgcttac tctcacctgc    2580
ttctgagttg cccaggagac cactggcaga tgtcccggcg aagagaagag acacattgtt    2640
ggaagaagca gcccatgaca gctcccctttc ctgggactcg ccctcatcct cttcctgctc    2700
cccttcctgg ggtgcagcct aaaaggacct atgtcctcac accattgaaa ccactagttc    2760
tgtcccccca ggagacctgg ttgtgtgtgt gtgagtggtt gaccttcctc catcccctgg    2820
tccttccctt cccttcccga ggcacagaga gacagggcag gatccacgtg cccattgtgg    2880
aggcagagaa aagagaaagt gttttatata cggtacttat ttaatatccc tttttaatta    2940
gaaattaaaa cagttaattt aattaaagag tagggttttt tttcagtatt cttggttaat    3000
atttaatttc aactatttat gagatgtatc ttttgctctc tcttgctctc ttatttgtac    3060
cggttttgt atataaaatt catgtttcca atctctctct ccctgatcgg tgacagtcac    3120
tagcttatct tgaacagata tttaattttg ctaacactca gctctgccct ccccgatccc    3180
ctggctcccc agcacacatt cctttgaaat aaggtttcaa tatacatcta catactatat    3240
atatatttgg caacttgtat ttgtgtgtat atatatatat atatgtttat gtatatatgt    3300
gattctgata aaatagacat tgctattctg ttttttatat gtaaaacaa aacaagaaaa    3360
aatagagaat tctacatact aaatctctct ccttttttaa ttttaatatt tgttatcatt    3420
tatttattgg tgctactgtt tatccgtaat aattgtgggg aaaagatatt aacatcacgt    3480
ctttgtctct agtgcagttt ttcgagatat tccgtagtac atatttattt ttaaacaacg    3540
```

```
acaaagaaat acagatatat cttaaaaaaa aaaaagcatt ttgtattaaa gaatttaatt    3600
ctgatctcaa aaaaaaaaaa aaaaaa                                        3626

<210> SEQ ID NO 118
<211> LENGTH: 3608
<212> TYPE: DNA
<213> ORGANISM: Artificial Sequence
<220> FEATURE:
<223> OTHER INFORMATION: Synthetic VEGF(NM_001171625.1)
<220> FEATURE:
<221> NAME/KEY: misc_feature
<222> LOCATION: (1039)..(1668)
<223> OTHER INFORMATION: CDS

<400> SEQUENCE: 118
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta tttttgcttg ccattcccca     240
cttgaatcgg gccgacggct tgggagatt gctctacttc cccaaatcac tgtggatttt     300
ggaaaccagc agaaagagga aagagtagc aagagctcca gagagaagtc gaggaagaga     360
gagacggggt cagagagagc gcgcgggcgt gcgagcagcg aaagcgacag gggcaaagtg     420
agtgacctgc ttttggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcgggctc gcggcgtcgc actgaaactt     660
ttcgtccaac ttctgggctg ttctcgcttc ggaggagccg tggtccgcgc ggggaagcc     720 gagccgagcg gagccgcgag aagtgctagc tcgggccggg aggagccgca gccggaggag     780
ggggaggagg aagaagagaa ggaagaggag aggggccgc agtggcgact cggcgctcgg     840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
gaggagagcg ggccgcccca gcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccgtccctg tgggccttgc tcagagcgga gaaagcattt gtttgtacaa    1560
gatccgcaga cgtgtaaatg ttcctgcaaa aacacagact cgcgttgcaa ggcgaggcag    1620
cttgagttaa acgaacgtac ttgcagatgt gacaagccga ggcggtgagc cgggcaggag    1680
gaaggagcct ccctcagggt ttcgggaacc agatctctca ccaggaaaga ctgatacaga    1740
acgatcgata cagaaaccac gctgccgcca ccacaccatc accatcgaca gaacagtcct    1800
taatccagaa acctgaaatg aaggaagagg agactctgcg cagagcactt tgggtccgga    1860
```

```
gggcgagact ccggcggaag cattcccggg cgggtgaccc agcacggtcc ctcttggaat    1920
tggattcgcc attttatttt tcttgctgct aaatcaccga gcccggaaga ttagagagtt    1980
ttatttctgg gattcctgta gacacaccca cccacataca tacatttata tatatatata    2040
ttatatatat ataaaaataa atatctctat tttatatata taaatatat atattctttt    2100 tttaaattaa cagtgctaat gttattggtg tcttcactgg atgtatttga ctgctgtgga    2160
cttgagttgg gagggaatg ttcccactca gatcctgaca gggaagagga ggagatgaga    2220
gactctggca tgatctttt tttgtcccac ttggtgggc cagggtcctc tcccctgccc    2280
aggaatgtgc aaggccaggg catgggggca aatatgaccc agttttggga acaccgacaa    2340
acccagccct ggcgctgagc ctctctaccc caggtcagac ggacagaaag acagatcaca    2400
ggtacaggga tgaggacacc ggctctgacc aggagtttgg ggagcttcag gacattgctg    2460
tgctttgggg attccctcca catgctgcac gcgcatctcg cccccagggg cactgcctgg    2520
aagattcagg agcctgggcg gccttcgctt actctcacct gcttctgagt tgcccaggag    2580
accactggca gatgtcccgg cgaagagaag agacacattg ttggaagaag cagcccatga    2640
cagctcccct tcctgggact cgccctcatc ctcttcctgc tccccttcct ggggtgcagc    2700
ctaaaaggac ctatgtcctc acaccattga aaccactagt tctgtccccc caggagacct    2760
ggttgtgtgt gtgtgagtgg ttgaccttcc tccatcccct ggtccttccc ttcccttccc    2820
gaggcacaga gagacagggc aggatccacg tgcccattgt ggaggcagag aaaagagaaa    2880
gtgttttata tacggtactt atttaatatc ccttttaat tagaaattaa acagttaat     2940 ttaattaaag gtagggttt tttttcagta ttcttggtta atatttaatt tcaactattt    3000
atgagatgta tcttttgctc tctcttgctc tcttatttgt accggttttt gtatataaaa    3060
ttcatgtttc caatctctct ctccctgatc ggtgacagtc actagcttat cttgaacaga    3120
tatttaattt tgctaacact cagctctgcc ctccccgatc ccctggctcc ccagcacaca    3180 ttccttgaa ataaggtttc aatatacatc tacatactat atatatattt ggcaacttgt     3240
atttgtgtgt atatatatat atatatgttt atgtatatat gtgattctga taaaatagac    3300
attgctattc tgttttttat atgtaaaaac aaaacaagaa aaaatagaga attctacata    3360
ctaaatctct ctccttttt aattttaata tttgttatca tttatttatt ggtgctactg     3420
tttatccgta ataattgtgg ggaaaagata ttaacatcac gtctttgtct ctagtgcagt    3480
ttttcgagat attccgtagt acatatttat ttttaaacaa cgacaaagaa atacagatat    3540
atcttaaaaa aaaaaaagca ttttgtatta aagaatttaa ttctgatctc aaaaaaaaaa    3600
aaaaaaaa                                                            3608
```

<210> SEQ ID NO 119  
<211> LENGTH: 3554  
<212> TYPE: DNA  
<213> ORGANISM: Artificial Sequence  
<220> FEATURE:  
<223> OTHER INFORMATION: Synthetic VEGF (NM_001171626.1)  
<220> FEATURE:  
<221> NAME/KEY: misc_feature  
<222> LOCATION: (1039)..(1614)  
<223> OTHER INFORMATION: CDS

<400> SEQUENCE: 119

```
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
```

```
ctcggtgctg aatttgata ttcattgatc cgggttttat ccctcttctt ttttcttaaa    180
catttttttt taaaactgta ttgtttctcg ttttaattta ttttttgcttg ccattcccca   240
cttgaatcgg gccgacggct tggggagatt gctctacttc cccaaatcac tgtggatttt   300
ggaaaccagc agaaagagga aagaggtagc aagagctcca gagagaagtc gaggaagaga   360
gagacgggt cagagagagc gcgcgggcgt gcgagcagcg aaagcgacag gggcaaagtg    420
agtgacctgc ttttggggt gaccgccgga gcgcggcgtg agccctcccc cttgggatcc    480
cgcagctgac cagtcgcgct gacggacaga cagacagaca ccgcccccag ccccagctac   540
cacctcctcc ccggccggcg gcggacagtg gacgcggcgg cgagccgcgg gcaggggccg   600
gagcccgcgc ccggaggcgg ggtggagggg gtcggggctc gcggcgtcgc actgaaactt   660
ttcgtccaac ttctgggctg ttctcgcttc ggaggagccg tggtccgcgc ggggaagcc    720
gagccgagcg gagccgcgag aagtgctagc tcggccggg aggagccgca gccggaggag    780
ggggaggagg aagaagagaa ggaagaggag aggggccgc agtggcgact cggcgctcgg    840
aagccgggct catggacggg tgaggcggcg gtgtgcgcag acagtgctcc agccgcgcgc   900
gctccccagg ccctggcccg ggcctcgggc cggggaggaa gagtagctcg ccgaggcgcc   960
gaggagagcg ggccgcccca cagcccgagc cggagaggga gcgcgagccg cgccggcccc  1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag agagatgag cttcctacag cacaacaaat gtgaatgcag accaaagaaa   1440
gatagagcaa gacaagaaaa tcccgtgtggg ccttgctcag agcggagaaa gcatttgttt  1500
gtacaagatc cgcagacgtg taaatgttcc tgcaaaaaca cagactcgcg ttgcaaggcg   1560
aggcagcttg agttaaacga acgtacttgc agatgtgaca agccgaggcg gtgagccggg   1620
caggaggaag gagcctccct cagggtttcg ggaaccagat ctctcaccag gaaagactga   1680
tacagaacga tcgatacaga aaccacgctg ccgccaccac accatcacca tcgacagaac   1740
agtccttaat ccagaaacct gaaatgaagg aagaggagac tctgcgcaga gcactttggg   1800
tccggagggc gagactccgg cggaagcatt cccgggcggg tgacccagca cggtcccctct  1860
tggaattgga ttcgccattt tattttctt gctgctaaat caccgagccc ggaagattag    1920
agagttttat ttctgggatt cctgtagaca cacccaccca catacataca tttatatata   1980
tatatattat atatataaa aaataaatat ctctatttta tatataaaa atatatatat     2040
tcttttttta aattaacagt gctaatgtta ttggtgtctt cactgatgt atttgactgc    2100
tgtggacttg agttgggagg ggaatgttcc cactcagatc ctgacaggga agaggaggag   2160
atgagagact ctggcatgat ctttttttg tcccacttgg tggggccagg gtcctctccc    2220
ctgcccagga atgtgcaagg ccagggcatg ggggcaaata tgacccagtt ttgggaacac   2280
cgacaaaccc agccctggcg ctgagcctct ctaccccagg tcagacggac agaaagacag   2340
atcacaggta cagggatgag gacaccggct ctgaccagga gtttggggag cttcaggaca   2400
ttgctgtgct ttggggattc cctccacatg ctgcacgcg atctcgcccc caggggcact   2460
gcctggaaga ttcaggagcc tgggcggcct tcgcttactc tcacctgctt ctgagttgcc   2520
```

```
caggagacca ctggcagatg tcccggcgaa gagaagagac acattgttgg aagaagcagc    2580
ccatgacagc tccccttcct gggactcgcc ctcatcctct tcctgctccc cttcctgggg    2640
tgcagcctaa aaggacctat gtcctcacac cattgaaacc actagttctg tcccccagg     2700 agacctggtt gtgtgtgtgt gagtggttga ccttcctcca tccctggtc  cttcccttcc    2760 cttcccgagg cacagagaga cagggcagga tccacgtgcc cattgtggag gcagagaaaa    2820
gagaaagtgt tttatatacg gtacttattt aatatccctt tttaattaga aattaaaaca    2880
gttaatttaa ttaaagagta gggtttttt  tcagtattct tggttaatat ttaatttcaa    2940
ctatttatga gatgtatctt ttgctctctc ttgctctctt atttgtaccg gttttttgtat    3000 ataaaattca tgtttccaat ctctctctcc ctgatcggtg acagtcacta gcttatcttg    3060
aacagatatt taattttgct aacactcagc tctgccctcc ccgatcccct ggctccccag    3120
cacacattcc tttgaaataa ggtttcaata tacatctaca tactatatat atatttggca    3180
acttgtattt gtgtgtatat atatatatat atgtttatgt atatatgtga ttctgataaa    3240
atagacattg ctattctgtt ttttatatgt aaaaacaaaa caagaaaaaa tagagaattc    3300
tacatactaa atctctctcc ttttttaatt taaatatttg ttatcattta tttattggtg    3360
ctactgttta tccgtaataa ttgtggggaa aagatattaa catcacgtct ttgtctctag    3420
tgcagttttt cgagatattc cgtagtacat atttatttt  aaacaacgac aaagaaatac    3480
agatatatct taaaaaaaaa aaagcatttt gtattaaaga atttaattct gatctcaaaa    3540
aaaaaaaaaa aaaa                                                     3554
```

<210> SEQ ID NO 120
<211> LENGTH: 3519
<212> TYPE: DNA
<213> ORGANISM: Artificial Sequence
<220> FEATURE:
<223> OTHER INFORMATION: Synthetic VEGF(NM_001171627.1)
<220> FEATURE:
<221> NAME/KEY: misc_feature
<222> LOCATION: (1039)..(1563)
<223> OTHER INFORMATION: CDS

<400> SEQUENCE: 120

```
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
catttttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag ggcaaagtg     420 agtgacctgc ttttggggt gaccgccgga gcgcggcgtg agccctcccc cttgggatcc    480
cgcagctgac cagtcgcgct gacggacaga cagacagaca ccgcccccag cccagctac    540 cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt    660
ttcgtccaac ttctgggctg ttctcgcttc ggaggagccg tggtccgcgc ggggaagcc    720 gagccgagcg gagccgcgag aagtgctagc tcgggccggg aggagccgca gccgaggag    780 ggggaggagg aagaagagaa ggaagaggag aggggggccgc agtggcgact cggcgctcgg    840
```

```
aagccgggct catggacggg tgaggcggcg gtgtgcgcag acagtgctcc agccgcgcgc    900 gctcccagg  ccctggccg  ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa tccctgtggg ccttgctcag agcggagaaa gcatttgttt   1500
gtacaagatc cgcagacgtg taaatgttcc tgcaaaaaca cagactcgcg ttgcaagatg   1560
tgacaagccg aggcggtgag ccgggcagga ggaaggagcc tccctcaggg tttcgggaac   1620
cagatctctc accaggaaag actgatacag aacgatcgat acagaaacca cgctgccgcc   1680
accacaccat caccatcgac agaacagtcc ttaatccaga aacctgaaat gaaggaagag   1740
gagactctgc gcagagcact ttgggtccgg agggcgagac tccggcggaa gcattcccgg   1800
gcgggtgacc cagcacggtc cctcttggaa ttggattcgc cattttattt ttcttgctgc   1860
taaatcaccg agcccggaag attagagagt tttatttctg ggattcctgt agacacaccc   1920
acccacatac atacatttat atatatatat attatatata tataaaaata aatatctcta   1980
ttttatatat ataaaatata tatattcttt ttttaaatta acagtgctaa tgttattggt   2040
gtcttcactg gatgtatttg actgctgtgg acttgagttg ggaggggaat gttcccactc   2100
agatcctgac agggaagagg aggagatgag agactctggc atgatctttt ttttgtccca   2160
cttggtgggg ccaggtcct  ctcccctgcc caggaatgtg caaggccagg gcatgggggc   2220
aaatatgacc cagttttggg aacaccgaca aacccagccc tggcgctgag cctctctacc   2280
ccaggtcaga cggacagaaa gacagatcac aggtacaggg atgaggacac cggctctgac   2340
caggagtttg gggagcttca ggacattgct gtgctttggg gattccctcc acatgctgca   2400
cgcgcatctc gcccccaggg gcactgcctg gaagattcag gagcctgggc ggccttcgct   2460
tactctcacc tgcttctgag ttgcccagga gaccactggc agatgtcccg gcgaagagaa   2520
gagacacatt gttggaagaa gcagcccatg acagctcccc ttcctgggac tcgccctcat   2580
cctcttcctg ctccccttcc tggggtgcag cctaaaagga cctatgtcct cacaccattg   2640
aaaccactag ttctgtcccc ccaggagacc tggttgtgtg tgtgtgagtg gttgaccttc   2700
ctccatcccc tggtccttcc cttcccttcc cgaggcacag agagacaggg caggatccac   2760
gtgcccattg tggaggcaga gaaaagagaa agtgttttat atacggtact tatttaatat   2820 cccttttaa  ttagaaatta aaacagttaa tttaattaaa gagtagggtt ttttttcagt   2880
attcttggtt aatatttaat ttcaactatt tatgagatgt atcttttgct ctctcttgct   2940
ctcttatttg taccggtttt tgtatataaa attcatgttt ccaatctctc tctccctgat   3000
cggtgacagt cactagctta tcttgaacag atatttaatt ttgctaacac tcagctctgc   3060
cctccccgat cccctggctc cccagcacac attcctttga aataaggttt caatatacat   3120
ctacatacta tatatatatt tggcaacttg tatttgtgtg tatatatata tatatatgtt   3180
tatgtatata tgtgattctg ataaaataga cattgctatt ctgttttta  tatgtaaaaa   3240
```

```
caaaacaaga aaaaatagag aattctacat actaaatctc tctcctttt taatttaat      3300 atttgttatc atttatttat tggtgctact gtttatccgt aataattgtg gggaaaagat      3360
attaacatca cgtctttgtc tctagtgcag ttttcgaga tattccgtag tacatattta      3420
tttttaaaca acgacaaaga aatacagata tatcttaaaa aaaaaaagc attttgtatt      3480 aaagaattta attctgatct caaaaaaaaa aaaaaaaa                              3519
```

<210> SEQ ID NO 121
<211> LENGTH: 3422
<212> TYPE: DNA
<213> ORGANISM: Artificial Sequence
<220> FEATURE:
<223> OTHER INFORMATION: Synthetic VEGF(NM_001171628.1)
<220> FEATURE:
<221> NAME/KEY: misc_feature
<222> LOCATION: (1039)..(1482)
<223> OTHER INFORMATION: CDS

<400> SEQUENCE: 121

```
tcgcggaggc ttggggcagc cgggtagctc ggaggtcgtg gcgctggggg ctagcaccag       60
cgctctgtcg ggaggcgcag cggttaggtg gaccggtcag cggactcacc ggccagggcg      120
ctcggtgctg gaatttgata ttcattgatc cgggttttat ccctcttctt ttttcttaaa      180
catttttttt taaaactgta ttgtttctcg ttttaattta ttttgcttg ccattcccca       240 cttgaatcgg gccgacggct ggggagatt gctctacttc cccaaatcac tgtggatttt       300
ggaaaccagc agaaagagga aagaggtagc aagagctcca gagagaagtc gaggaagaga      360
gagacggggt cagagagagc gcgcgggcgt gcgagcagcg aaagcgacag ggcaaagtg       420 agtgacctgc ttttgggggt gaccgccgga gcgcggcgtg agccctcccc cttgggatcc      480
cgcagctgac cagtcgcgct gacggacaga cagacagaca ccgcccccag ccccagctac      540
cacctcctcc ccggccggcg gcggacagtg gacgcggcgg cgagccgcgg gcaggggccg      600
gagcccgcgc ccggaggcgg ggtggagggg gtcggggctc gcggcgtcgc actgaaactt      660
ttcgtccaac ttctgggctg ttctcgcttc ggaggagccg tggtccgcgc ggggaagcc       720 agccgagcg gagccgcgag aagtgctagc tcgggccggg aggagccgca gccggaggag       780
ggggaggagg aagaagagaa ggaagaggag aggggccgc agtggcgact cggcgctcgg       840
aagccgggct catggacggg tgaggcgcg gtgtgcgcag acagtgctcc agccgcgcgc      900 gctcccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgccctgat gcgatgcggg ggctgctgca atgacgaggg cctggagtgt     1320
gtgcccactg aggagtccaa catcaccatg cagattatgc ggatcaaacc tcaccaaggc     1380
cagcacatag agagatgag cttcctacag cacaacaaat gtgaatgcag accaaagaaa     1440
gatagagcaa gacaagaaaa atgtgacaag ccgaggcggt gagccgggca ggaggaagga     1500
gcctccctca gggtttcggg aaccagatct ctcaccagga aagactgata cagaacgatc     1560
gatacagaaa ccacgctgcc gccaccacac catcaccatc gacagaacag tccttaatcc     1620
```

| agaaacctga aatgaaggaa gaggagactc tgcgcagagc actttgggtc cggagggcga | 1680 |
| gactccggcg gaagcattcc cgggcgggtg acccagcacg gtccctcttg gaattggatt | 1740 |
| cgccatttta ttttcttgc tgctaaatca ccgagcccgg aagattagag agttttattt | 1800 |
| ctgggattcc tgtagacaca cccacccaca tacatacatt tatatatata tatattatat | 1860 |
| atatataaaa ataaatatct ctattttata tatataaaat atatatattc ttttttaaa | 1920 |
| ttaacagtgc taatgttatt ggtgtcttca ctggatgtat ttgactgctg tggacttgag | 1980 |
| ttgggagggg aatgttccca ctcagatcct gacagggaag aggaggagat gagagactct | 2040 |
| ggcatgatct tttttttgtc ccacttggtg gggccaggt cctctcccct gcccaggaat | 2100 |
| gtgcaaggcc agggcatggg ggcaaatatg acccagtttt gggaacaccg acaaacccag | 2160 |
| ccctggcgct gagcctctct accccaggtc agacggacag aaagacagat cacaggtaca | 2220 |
| gggatgagga caccggctct gaccaggagt ttggggagct tcaggacatt gctgtgcttt | 2280 |
| ggggattccc tccacatgct gcacgcgcat ctcgccccca ggggcactgc ctggaagatt | 2340 |
| caggagcctg ggcggccttc gcttactctc acctgcttct gagttgccca ggagaccact | 2400 |
| ggcagatgtc ccggcgaaga gaagagacac attgttggaa gaagcagccc atgacagctc | 2460 |
| cccttcctgg gactcgccct catcctcttc ctgctcccct tcctggggtg cagcctaaaa | 2520 |
| ggacctatgt cctcacacca ttgaaaccac tagttctgtc cccccaggag acctggttgt | 2580 |
| gtgtgtgtga gtggttgacc ttcctccatc ccctggtcct tcccttccct tcccgaggca | 2640 |
| cagagagaca gggcaggatc cacgtgccca ttgtggaggc agagaaaaga gaaagtgttt | 2700 |
| tatatacggt acttatttaa tatccctttt taattagaaa ttaaaacagt taatttaatt | 2760 |
| aaagagtagg gttttttttc agtattcttg gttaatattt aatttcaact atttatgaga | 2820 |
| tgtatctttt gctctctctt gctctcttat ttgtaccggt ttttgtatat aaaattcatg | 2880 |
| tttccaatct ctctctccct gatcggtgac agtcactagc ttatcttgaa cagatattta | 2940 |
| attttgctaa cactcagctc tgccctcccc gatcccctgg ctccccagca cacattcctt | 3000 |
| tgaaataagg tttcaatata catctacata ctatatatat atttggcaac ttgtatttgt | 3060 |
| gtgtatatat atatatatat gtttatgtat atatgtgatt ctgataaaat agacattgct | 3120 |
| attctgtttt ttatatgtaa aaacaaaaca agaaaaaata gagaattcta catactaaat | 3180 |
| ctctctcctt ttttaattttt aatatttgtt atcatttatt tattggtgct actgtttatc | 3240 |
| cgtaataatt gtggggaaaa gatattaaca tcacgtcttt gtctctagtg cagttttcg | 3300 |
| agatattccg tagtacatat ttattttaa acaacgacaa agaaatacag atatatctta | 3360 |
| aaaaaaaaaa agcatttgt attaaagaat ttaattctga tctcaaaaaa aaaaaaaaaa | 3420 |
| aa | 3422 |

<210> SEQ ID NO 122
<211> LENGTH: 3488
<212> TYPE: DNA
<213> ORGANISM: Artificial Sequence
<220> FEATURE:
<223> OTHER INFORMATION: Synthetic VEGF(NM_001171629.1)
<220> FEATURE:
<221> NAME/KEY: misc_feature
<222> LOCATION: (1039)..(1614)
<223> OTHER INFORMATION: CDS

<400> SEQUENCE: 122

| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |

```
ctcggtgctg gaatttgata ttcattgatc cgggttttat ccctcttctt ttttcttaaa    180
cattttttt  taaaactgta ttgtttctcg ttttaattta tttttgcttg ccattcccca    240
cttgaatcgg gccgacggct tggggagatt gctctacttc cccaaatcac tgtggatttt    300
ggaaaccagc agaagagga  aagaggtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg cagggggccg    600
gagcccgcgc ccggaggcgg ggtggagggg gtcgggcgtc gcggcgtcgc actgaaactt    660
ttcgtccaac ttctgggctg ttctcgcttc ggaggagccg tggtccgcgc gggggaagcc    720
gagccgagcg gagccgcgag aagtgctagc tcggccgggg aggagccgca gccggaggag    780
ggggaggagg aagaagagaa ggaagaggag aggggccgc  agtggcgact cggcgctcgg    840
aagccgggct catggacggg tgaggcggcg gtgtgcgcag acagtgctcc agccgcgcgc    900
gctcccagg  ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa tccctgtggg ccttgctcag agcggagaaa gcatttgttt   1500
gtacaagatc cgcagacgtg taaatgttcc tgcaaaaaca cagactcgcg ttgcaaggcg   1560
aggcagcttg agttaaacga acgtacttgc agatctctca ccaggaaaga ctgatacaga   1620
acgatcgata cagaaaccac gctgccgcca ccacaccatc accatcgaca gaacagtcct   1680
taatccagaa acctgaaatg aaggaagagg agactctgcg cagagcactt tgggtccgga   1740
gggcgagact ccggcggaag cattcccggg cgggtgaccc agcacggtcc ctcttggaat   1800
tggattcgcc attttatttt tcttgctgct aaatcaccga gcccggaaga ttagagagtt   1860
ttatttctgg gattcctgta gacacaccca cccacataca tacatttata tatatata    1920
ttatatatat ataaaaataa atatctctat tttatatata taaatatat  atattctttt   1980
tttaaattaa cagtgctaat gttattggtg tcttcactgg atgtatttga ctgctgtgga   2040
cttgagttgg gagggaatg  ttcccactca gatcctgaca gggaagagga ggagatgaga   2100
gactctggca tgatcttttt tttgtcccac ttggtggggc cagggtcctc tcccctgccc   2160
aggaatgtgc aaggccaggg catgggggca aatatgaccc agttttggga acaccgacaa   2220
acccagccct ggcgctgagc ctctctaccc caggtcagac ggacagaaag acagatcaca   2280
ggtacaggga tgaggacacc ggctctgacc aggagtttgg ggagcttcag gacattgctg   2340
tgctttgggg attccctcca catgctgcac gcgcatctcg cccccagggg cactgcctgg   2400
aagattcagg agcctgggcg gccttcgctt actctcacct gcttctgagt tgcccaggag   2460
```

```
accactggca gatgtcccgg cgaagagaag agacacattg ttggaagaag cagcccatga    2520
cagctcccct tcctgggact cgccctcatc ctcttcctgc tccccttcct ggggtgcagc    2580
ctaaaaggac ctatgtcctc acaccattga aaccactagt tctgtccccc caggagacct    2640
ggttgtgtgt gtgtgagtgg ttgaccttcc tccatcccct ggtccttccc ttcccttccc    2700
gaggcacaga gagacagggc aggatccacg tgcccattgt ggaggcagag aaaagagaaa    2760
gtgttttata tacggtactt atttaatatc ccttttaat tagaaattaa acagttaat    2820 ttaattaaag agtagggttt tttttcagta ttcttggtta atatttaatt tcaactattt    2880
atgagatgta tcttttgctc tctcttgctc tcttatttgt accggttttt gtatataaaa    2940
ttcatgtttc caatctctct ctccctgatc ggtgacagtc actagcttat cttgaacaga    3000
tatttaattt tgctaacact cagctctgcc ctcccccgatc ccctggctcc ccagcacaca    3060
ttcctttgaa ataaggtttc aatatacatc tacatactat atatatattt ggcaacttgt    3120
atttgtgtgt atatatatat atatgtttt atgtatatat gtgattctga taaaatagac    3180
attgctattc tgttttttat atgtaaaaac aaaacaagaa aaaatagaga attctacata    3240
ctaaatctct ctccttttt aattttaata tttgttatca tttatttatt ggtgctactg    3300
tttatccgta ataattgtgg ggaaaagata ttaacatcac gtctttgtct ctagtgcagt    3360
ttttcgagat attccgtagt acatatttat ttttaaacaa cgacaaagaa atacagatat    3420
atcttaaaaa aaaaaaagca ttttgtatta aagaatttaa ttctgatctc aaaaaaaaaa    3480
aaaaaaaa                                                              3488

<210> SEQ ID NO 123
<211> LENGTH: 3392
<212> TYPE: DNA
<213> ORGANISM: Artificial Sequence
<220> FEATURE:
<223> OTHER INFORMATION: Synthetic VEGF(NM_001171630.1)
<220> FEATURE:
<221> NAME/KEY: misc_feature
<222> LOCATION: (1039)..(1452)
<223> OTHER INFORMATION: CDS

<400> SEQUENCE: 123
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta tttttgcttg ccattcccca     240
cttgaatcgg gccgacggct tggggagatt gctctacttc cccaaatcac tgtggatttt     300
ggaaaccagc agaaagagga aagagtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcagggccg     600 gagcccgcgc ccggaggcgg ggtggagggg gtcgggctc gcggcgtcgc actgaaactt     660
ttcgtccaac ttctgggctg ttctcgcttc ggaggagccg tggtccgcgc gggggaagcc     720
gagccgagcg gagccgcgag aagtgctagc tcgggccggg aggagccgca gccggaggag     780
ggggaggagg aagaagagaa ggaagaggag agggggccgc agtggcgact cggcgctcgg     840
aagccgggct catggacggg tgaggcggcg gtgtgcgcag acagtgctcc agccgcgcgc     900
```

```
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag agagatgag cttcctacag cacaacaaat gtgaatgcag atgtgacaag   1440
ccgaggcggt gagccgggca ggaggaagga gcctccctca gggtttcggg aaccagatct   1500
ctcaccagga aagactgata cagaacgatc gatacagaaa ccacgctgcc gccaccacac   1560
catcaccatc gacagaacag tccttaatcc agaaacctga aatgaaggaa gaggagactc   1620
tgcgcagagc actttgggtc cggagggcga gactccggcg gaagcattcc cgggcgggtg   1680
acccagcacg gtccctcttg gaattggatt cgccatttta ttttttcttgc tgctaaatca   1740 ccgagcccgg aagattagag agtttatttt ctgggattcc tgtagacaca cccacccaca   1800
tacatacatt tatatatata tatattatat atatataaaa ataaatatct ctattttata   1860
tatataaaat atatatattc ttttttttaaa ttaacagtgc taatgttatt ggtgtcttca   1920
ctggatgtat ttgactgctg tggacttgag ttgggagggg aatgttccca ctcagatcct   1980
gacagggaag aggaggagat gagagactct ggcatgatct ttttttttgtc ccacttggtg   2040 gggccagggt cctctcccct gcccaggaat gtgcaaggcc agggcatggg ggcaaatatg   2100
acccagtttt gggaacaccg acaaacccag ccctggcgct gagcctctct accccaggtc   2160
agacggacag aaagacagat cacaggtaca gggatgagga caccggctct gaccaggagt   2220
ttggggagct tcaggacatt gctgtgcttt ggggattccc tccacatgct gcacgcgcat   2280
ctcgccccca ggggcactgc ctggaagatt caggagcctg gcggccttc gcttactctc   2340 acctgcttct gagttgccca ggagaccact ggcagatgtc ccggcgaaga gaagagacac   2400
attgttggaa gaagcagccc atgacagctc cccttcctgg gactcgccct catcctcttc   2460
ctgctcccct tcctggggtg cagcctaaaa ggacctatgt cctcacacca ttgaaaccac   2520
tagttctgtc cccccaggag acctggttgt gtgtgtgtga gtggttgacc ttcctccatc   2580
ccctggtcct tcccttccct tcccgaggca cagagagaca gggcaggatc cacgtgccca   2640
ttgtggaggc agagaaaaga gaaagtgttt tatatacggt acttatttaa tatccctttt   2700
taattagaaa ttaaaacagt taatttaatt aaagagtagg gttttttttc agtattcttg   2760
gttaatattt aatttcaact atttatgaga tgtatctttt gctctctctt gctctcttat   2820
ttgtaccggt ttttgtatat aaaattcatg tttccaatct ctctctccct gatcggtgac   2880
agtcactagc ttatcttgaa cagatattta attttgctaa cactcagctc tgccctcccc   2940
gatcccctgg ctccccagca cacattcctt tgaaataagg tttcaatata catctacata   3000
ctatatatat atttggcaac ttgtatttgt gtgtatatat atatatatat gtttatgtat   3060
atatgtgatt ctgataaaat agacattgct attctgtttt ttatatgtaa aaacaaaaca   3120
agaaaaaata gagaattcta catactaaat ctctctcctt ttttaatttt aatatttgtt   3180
atcatttatt tattggtgct actgtttatc cgtaataatt gtggggaaaa gatattaaca   3240
```

| | |
|---|---|
| tcacgtctttt gtctctagtg cagtttttcg agatattccg tagtacatat ttatttttaa | 3300 |
| acaacgacaa agaaatacag atatatctta aaaaaaaaaa agcattttgt attaaagaat | 3360 |
| ttaattctga tctcaaaaaa aaaaaaaaaa aa | 3392 |

<210> SEQ ID NO 124
<211> LENGTH: 3494
<212> TYPE: DNA
<213> ORGANISM: Artificial Sequence
<220> FEATURE:
<223> OTHER INFORMATION: Synthetic VEGF(NM_001204384.1)
<220> FEATURE:
<221> NAME/KEY: misc_feature
<222> LOCATION: (1039)..(1554)
<223> OTHER INFORMATION: CDS

<400> SEQUENCE: 124

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta ttttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag ggcaaagtg | 420 |
| agtgacctgc ttttggggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggcctc gcggcgtcgc actgaaactt | 660 |
| ttcgtccaac ttctgggctg ttctcgcttc ggaggagccg tggtccgcgc ggggaagcc | 720 |
| gagccgagcg gagccgcgag aagtgctagc tcgggccggg aggagccgca gccgaggag | 780 |
| ggggaggagg aagaagagaa ggaagaggag aggggggccgc agtggcgact cggcgctcgg | 840 |
| aagccgggct catggacggg tgaggcgcg gtgtgcgcag acagtgctcc agccgcgcgc | 900 |
| gctccccagg ccctggcccg ggcctcgggc cggggaggaa gagtagctcg ccgaggcgcc | 960 |
| gaggagagcg ggccgcccca cagcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag taccctgatg agatcgagta catcttcaag | 1260 |
| ccatcctgtg tgcccctgat gcgatgcggg ggctgctgca atgacgaggg cctggagtgt | 1320 |
| gtgcccactg aggagtccaa catcaccatg cagattatgc ggatcaaacc tcaccaaggc | 1380 |
| cagcacatag agagatgag cttcctacag cacaacaaat gtgaatgcag accaaagaaa | 1440 |
| gatagagcaa gacaagaaaa aaaatcagtt cgaggaaagg gaaagggca aaaacgaaag | 1500 |
| cgcaagaaat cccggtataa gtcctggagc gtatgtgaca gccgaggcg gtgagccggg | 1560 |
| caggaggaag gagcctccct cagggttccg ggaaccagat ctctcaccag gaaagactga | 1620 |
| tacagaacga tcgatacaga aaccacgctg ccgccaccac accatcacca tcgacagaac | 1680 |
| agtcctgaat ccagaaaacct gaaatgaagg aagaggagac tctgcgcaga gcactttggg | 1740 |
| tccggagggc gagactccgg cggaagcatt cccgggcggg tgacccagca cggtccctct | 1800 |

-continued

```
tggaattgga ttcgccattt tattttctt gctgctaaat caccgagccc ggaagattag    1860
agagttttat ttctgggatt cctgtagaca cacccaccca catacataca tttatatata    1920
tatatattat atatatataa aaataaatat ctctatttta tatatataaa atatatatat    1980 tctttttta aattaacagt gctaatgtta ttggtgtctt cactggatgt atttgactgc    2040
tgtggacttg agttgggagg ggaatgttcc cactcagatc ctgacaggga agaggaggag    2100
atgagagact ctggcatgat ctttttttg tcccacttgg tggggccagg gtcctctccc    2160
ctgcccagga atgtgcaagg ccagggcatg ggggcaaata tgacccagtt ttgggaacac    2220
cgacaaaccc agccctggcg ctgagcctct ctaccccagg tcagacggac agaaagacag    2280
atcacaggta cagggatgag gacaccggct ctgaccagga gtttggggag cttcaggaca    2340
ttgctgtgct ttggggattc cctccacatg ctgcacgcgc atctcgcccc caggggcact    2400
gcctggaaga ttcaggagcc tgggcggcct tcgcttactc tcacctgctt ctgagttgcc    2460
caggagacca ctggcagatg tcccggcgaa gagaagagac acattgttgg aagaagcagc    2520
ccatgacagc tccccttcct gggactcgcc ctcatcctct tcctgctccc cttcctgggg    2580
tgcagcctaa aaggacctat gtcctcacac cattgaaacc actagttctg tcccccagg    2640 agacctggtt gtgtgtgtgt gagtggttga ccttcctcca tccctggtc cttcccttcc    2700 cttcccgagg cacagagaga cagggcagga tccacgtgcc cattgtggag gcagagaaaa    2760
gagaaagtgt tttatatacg gtacttattt aatatccctt tttaattaga aattaaaaca    2820
gttaatttaa ttaaagagta gggttttttt tcagtattct tggttaatat ttaatttcaa    2880
ctatttatga gatgtatctt ttgctctctc ttgctctctt atttgtaccg gttttgtat    2940 ataaaattca tgtttccaat ctctctctcc ctgatcggtg acagtcacta gcttatcttg    3000
aacagatatt taattttgct aacactcagc tctgccctcc ccgatcccct ggctccccag    3060
cacacattcc tttgaaataa ggtttcaata tacatctaca tactatatat atatttggca    3120
acttgtattt gtgtgtatat atatatatat atgtttatgt atatatgtga ttctgataaa    3180
atagacattg ctattctgtt ttttatatgt aaaaacaaaa caagaaaaaa tagagaattc    3240
tacatactaa atctctctcc ttttttaatt ttaatatttg ttatcattta tttattggtg    3300
ctactgttta tccgtaataa ttgtgggaa aagatattaa catcacgtct ttgtctctag    3360
tgcagttttt cgagatattc cgtagtacat atttattttt aaacaacgac aaagaaatac    3420
agatatatct taaaaaaaa aaagcatttt gtattaaaga atttaattct gatctcaaaa    3480 aaaaaaaaa aaaa                                                     3494
```

<210> SEQ ID NO 125
<211> LENGTH: 3494
<212> TYPE: DNA
<213> ORGANISM: Artificial Sequence
<220> FEATURE:
<223> OTHER INFORMATION: Synthetic VEGF(NM_001204385.1)
<220> FEATURE:
<221> NAME/KEY: misc_feature
<222> LOCATION: (499)..(1554)
<223> OTHER INFORMATION: CDS

<400> SEQUENCE: 125

```
tcgcggaggc ttggggcagc cgggtagctc ggaggtcgtg cgctgggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
```

```
catttttttt taaaactgta ttgtttctcg ttttaattta ttttttgcttg ccattcccca    240 cttgaatcgg gccgacggct tggggagatt gctctacttc cccaaatcac tgtggatttt    300
ggaaaccagc agaaagagga aagaggtagc aagagctcca gagagaagtc gaggaagaga    360 gagacgggt cagagagagc gcgcgggcgt gcgagcagcg aaagcgacag ggcaaagtg      420 agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcggggctc gcggcgtcgc actgaaactt    660
ttcgtccaac ttctgggctg ttctcgcttc ggaggagccg tggtccgcgc ggggggaagcc    720 gagccgagcg gagccgcgag aagtgctagc tcgggccggg aggagccgca gccgaggag     780 ggggaggagg aagaagagaa ggaagaggag aggggccgc agtggcgact cggcgctcgg     840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtatgtgaca agccgaggcg gtgagccggg    1560
caggaggaag gagcctccct cagggtttcg ggaaccagat ctctcaccag gaaagactga    1620
tacagaacga tcgatacaga aaccacgctg ccgccaccac accatcacca tcgacagaac    1680
agtccttaat ccagaaacct gaaatgaagg aagaggagac tctgcgcaga gcactttggg    1740
tccggagggc gagactccgg cggaagcatt cccgggcggg tgacccagca cggtccctct    1800
tggaattgga ttcgccattt tatttttctt gctgctaaat caccgagccc ggaagattag    1860
agagttttat ttctgggatt cctgtagaca cacccaccca catacataca tttatatata    1920
tatatattat atatatataa aaataaatat ctctatttta tatatataaa atatatatat    1980
tcttttttta aattaacagt gctaatgtta ttggtgtctt cactggatgt atttgactgc    2040
tgtggacttg agttgggagg ggaatgttcc cactcagatc ctgacaggga agaggaggag    2100
atgagagact ctggcatgat ctttttttttg tcccacttgg tggggccagg gtcctctccc    2160
ctgcccagga atgtgcaagg ccagggcatg ggggcaaata tgacccagtt ttgggaacac    2220
cgacaaaccc agccctggcg ctgagcctct ctaccccagg tcagacggac agaaagacag    2280
atcacaggta cagggatgag gacaccggct ctgaccagga gtttgggagg cttcaggaca    2340
ttgctgtgct ttggggattc cctccacatg ctgcacgcgc atctcgcccc caggggcact    2400
gcctggaaga ttcaggagcc tgggcggcct tcgcttactc tcacctgctt ctgagttgcc    2460
caggagacca ctggcagatg tcccggcgaa gagaagagac acattgttgg aagaagcagc    2520
ccatgacagc tccccttcct gggactcgcc ctcatcctct tcctgctccc cttcctgggg    2580
```

| | |
|---|---|
| tgcagcctaa aaggacctat gtcctcacac cattgaaacc actagttctg tcccccagg | 2640 |
| agacctggtt gtgtgtgtgt gagtggttga ccttcctcca tccctggtc cttcccttcc | 2700 |
| cttcccgagg cacagagaga cagggcagga tccacgtgcc cattgtggag gcagagaaaa | 2760 |
| gagaaagtgt tttatatacg gtacttattt aatatcccctt tttaattaga aattaaaaca | 2820 |
| gttaatttaa ttaaagagta gggttttttt tcagtattct tggttaatat ttaatttcaa | 2880 |
| ctatttatga gatgtatctt ttgctctctc ttgctctctt atttgtaccg gttttgtat | 2940 |
| ataaaattca tgtttccaat ctctctctcc ctgatcggtg acagtcacta gcttatcttg | 3000 |
| aacagatatt taattttgct aacactcagc tctgccctcc ccgatcccct ggctcccag | 3060 |
| cacacattcc tttgaaataa ggtttcaata tacatctaca tactatatat atatttggca | 3120 |
| acttgtattt gtgtgtatat atatatatat atgtttatgt atatatgtga ttctgataaa | 3180 |
| atagacattg ctattctgtt tttatatgt aaaaacaaaa caagaaaaaa tagagaattc | 3240 |
| tacatactaa atctctctcc tttttaatt ttaatatttg ttatcattta tttattggtg | 3300 |
| ctactgttta tccgtaataa ttgtggggaa aagatattaa catcacgtct ttgtctctag | 3360 |
| tgcagtttt cgagatattc cgtagtacat atttattttt aaacaacgac aaagaaatac | 3420 |
| agatatatct taaaaaaaaa aaagcatttt gtattaaaga atttaattct gatctcaaaa | 3480 |
| aaaaaaaaaa aaaa | 3494 |

<210> SEQ ID NO 126
<211> LENGTH: 3626
<212> TYPE: DNA
<213> ORGANISM: Artificial Sequence
<220> FEATURE:
<223> OTHER INFORMATION: Synthetic VEGF(NM_003376.5)
<220> FEATURE:
<221> NAME/KEY: misc_feature
<222> LOCATION: (499)..(1686)
<223> OTHER INFORMATION: CDS

<400> SEQUENCE: 126

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| cattttttt taaaactgta ttgtttctcg ttttaattta tttttgcttg ccattcccca | 240 |
| cttgaatcgg gccgacggct tgggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag gggcaaagtg | 420 |
| agtgacctgc ttttggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc ggggaagcc | 720 |
| gagccgagcg gagccgcgag aagtgctagc tcgggccggg aggagccgca gccggaggag | 780 |
| ggggaggagg aagaagagaa ggaagaggag agggggccgc agtggcgact cggcgctcgg | 840 |
| aagccgggct catggacggg tgaggcggcg gtgtgcgcag acagtgctcc agccgcgcgc | 900 |
| gctccccagg ccctggcccg ggcctcgggc cggggaggaa gagtagctcg ccgaggcgcc | 960 |

```
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa    1440
gatagagcaa gacaagaaaa aaaatcagtt cgaggaaagg gaaagggca aaaacgaaag    1500 cgcaagaaat cccggtataa gtcctggagc gttccctgtg ggccttgctc agagcggaga    1560
aagcatttgt ttgtacaaga tccgcagacg tgtaaatgtt cctgcaaaaa cacagactcg    1620
cgttgcaagg cgaggcagct tgagttaaac aacgtactt gcagatgtga caagccgagg    1680
cggtgagccg ggcaggagga aggagcctcc ctcagggttt cgggaaccag atctctcacc    1740
aggaaagact gatacagaac gatcgataca gaaaccacgc tgccgccacc acaccatcac    1800
catcgacaga acagtcctta atccagaaac ctgaaatgaa ggaagaggag actctgcgca    1860
gagcactttg ggtccggagg gcgagactcc ggcggaagca ttcccgggcg ggtgacccag    1920
cacggtccct cttggaattg gattcgccat tttattttc ttgctgctaa atcaccgagc    1980
ccggaagatt agagagtttt atttctggga ttcctgtaga cacacccacc cacatacata    2040
catttatata tatatatatt atatatatat aaaaataaat atctctattt tatatatata    2100
aaatatatat attcttttt taaattaaca gtgctaatgt tattggtgtc ttcactggat    2160
gtatttgact gctgtggact tgagttggga ggggaatgtt cccactcaga tcctgacagg    2220
gaagaggagg agatgagaga ctctggcatg atctttttt tgtcccactt ggtggggcca    2280
gggtcctctc ccctgcccag gaatgtgcaa ggccagggca tggggcaaa tatgacccag    2340 ttttgggaac accgacaaac ccagccctgg cgctgagcct ctctacccca ggtcagacgg    2400
acagaaagac agatcacagg tacagggatg aggacaccgg ctctgaccag gagtttgggg    2460
agcttcagga cattgctgtg ctttggggat tccctccaca tgctgcacgc gcatctcgcc    2520
cccaggggca ctgcctggaa gattcaggag cctgggcggc cttcgcttac tctcacctgc    2580
ttctgagttg cccaggagac cactggcaga tgtcccggcg aagagaagag acacattgtt    2640
ggaagaagca gcccatgaca gctccccttc ctgggactcg ccctcatcct cttcctgctc    2700
cccttcctgg ggtgcagcct aaaaggacct atgtcctcac accattgaaa ccactagttc    2760
tgtcccccca ggagacctgg ttgtgtgtgt gtgagtggtt gaccttcctc catcccctgg    2820
tccttccctt cccttcccga ggcacagaga gacagggcag gatccacgtg cccattgtgg    2880
aggcagagaa aagagaaagt gtttttatata cggtacttat ttaatatccc tttttaatta    2940
gaaattaaaa cagttaattt aattaaagag tagggttttt tttcagtatt cttggttaat    3000
atttaatttc aactatttat gagatgtatc ttttgctctc tcttgctctc ttatttgtac    3060
cggtttttgt atataaaatt catgtttcca atctctctct ccctgatcgg tgacagtcac    3120
tagcttatct tgaacagata tttaattttg ctaacactca gctctgccct ccccgatccc    3180
ctggctcccc agcacacatt cctttgaaat aaggtttcaa tatacatcta catactatat    3240
atatatttgg caacttgtat ttgtgtgtat atatatatat atatgtttat gtatatatgt    3300
gattctgata aaatagacat tgctattctg ttttttatat gtaaaaacaa aacaagaaaa    3360
```

```
aatagagaat tctacatact aaatctctct ccttttttaa ttttaatatt tgttatcatt    3420
tatttattgg tgctactgtt tatccgtaat aattgtgggg aaaagatatt aacatcacgt    3480
ctttgtctct agtgcagttt ttcgagatat tccgtagtac atatttattt ttaaacaacg    3540
acaaagaaat acagatatat cttaaaaaaa aaaagcatt ttgtattaaa gaatttaatt    3600
ctgatctcaa aaaaaaaaaa aaaaaa                                        3626
```

<210> SEQ ID NO 127
<211> LENGTH: 1390
<212> TYPE: PRT
<213> ORGANISM: Artificial Sequence
<220> FEATURE:
<223> OTHER INFORMATION: Synthetic human c-Met (NP_000236)

<400> SEQUENCE: 127

```
Met Lys Ala Pro Ala Val Leu Ala Pro Gly Ile Leu Val Leu Leu Phe
  1               5                  10                  15

Thr Leu Val Gln Arg Ser Asn Gly Glu Cys Lys Glu Ala Leu Ala Lys
                 20                  25                  30

Ser Glu Met Asn Val Asn Met Lys Tyr Gln Leu Pro Asn Phe Thr Ala
             35                  40                  45

Glu Thr Pro Ile Gln Asn Val Ile Leu His Glu His His Ile Phe Leu
         50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
```

-continued

```
              305                 310                 315                 320
        Tyr Val Ser Lys Pro Gly Ala Gln Leu Ala Arg Gln Ile Gly Ala Ser
                        325                 330                 335

Leu Asn Asp Asp Ile Leu Phe Gly Val Phe Ala Gln Ser Lys Pro Asp
                        340                 345                 350

Ser Ala Glu Pro Met Asp Arg Ser Ala Met Cys Ala Phe Pro Ile Lys
                        355                 360                 365

Tyr Val Asn Asp Phe Phe Asn Lys Ile Val Asn Lys Asn Asn Val Arg
                        370                 375                 380

Cys Leu Gln His Phe Tyr Gly Pro Asn His Glu His Cys Phe Asn Arg
        385                 390                 395                 400

Thr Leu Leu Arg Asn Ser Ser Gly Cys Glu Ala Arg Arg Asp Glu Tyr
                        405                 410                 415

Arg Thr Glu Phe Thr Thr Ala Leu Gln Arg Val Asp Leu Phe Met Gly
                        420                 425                 430

Gln Phe Ser Glu Val Leu Leu Thr Ser Ile Ser Thr Phe Ile Lys Gly
                        435                 440                 445

Asp Leu Thr Ile Ala Asn Leu Gly Thr Ser Glu Gly Arg Phe Met Gln
                        450                 455                 460

Val Val Val Ser Arg Ser Gly Pro Ser Thr Pro His Val Asn Phe Leu
        465                 470                 475                 480

Leu Asp Ser His Pro Val Ser Pro Glu Val Ile Val Glu His Thr Leu
                        485                 490                 495

Asn Gln Asn Gly Tyr Thr Leu Val Ile Thr Gly Lys Lys Ile Thr Lys
                        500                 505                 510

Ile Pro Leu Asn Gly Leu Gly Cys Arg His Phe Gln Ser Cys Ser Gln
                        515                 520                 525

Cys Leu Ser Ala Pro Pro Phe Val Gln Cys Gly Trp Cys His Asp Lys
                        530                 535                 540

Cys Val Arg Ser Glu Glu Cys Leu Ser Gly Thr Trp Thr Gln Gln Ile
        545                 550                 555                 560

Cys Leu Pro Ala Ile Tyr Lys Val Phe Pro Asn Ser Ala Pro Leu Glu
                        565                 570                 575

Gly Gly Thr Arg Leu Thr Ile Cys Gly Trp Asp Phe Gly Phe Arg Arg
                        580                 585                 590

Asn Asn Lys Phe Asp Leu Lys Lys Thr Arg Val Leu Leu Gly Asn Glu
                        595                 600                 605

Ser Cys Thr Leu Thr Leu Ser Glu Ser Thr Met Asn Thr Leu Lys Cys
                        610                 615                 620

Thr Val Gly Pro Ala Met Asn Lys His Phe Asn Met Ser Ile Ile Ile
        625                 630                 635                 640

Ser Asn Gly His Gly Thr Thr Gln Tyr Ser Thr Phe Ser Tyr Val Asp
                        645                 650                 655

Pro Val Ile Thr Ser Ile Ser Pro Lys Tyr Gly Pro Met Ala Gly Gly
                        660                 665                 670

Thr Leu Leu Thr Leu Thr Gly Asn Tyr Leu Asn Ser Gly Asn Ser Arg
                        675                 680                 685

His Ile Ser Ile Gly Gly Lys Thr Cys Thr Leu Lys Ser Val Ser Asn
                        690                 695                 700

Ser Ile Leu Glu Cys Tyr Thr Pro Ala Gln Thr Ile Ser Thr Glu Phe
        705                 710                 715                 720

Ala Val Lys Leu Lys Ile Asp Leu Ala Asn Arg Glu Thr Ser Ile Phe
                        725                 730                 735
```

```
Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln Val
    1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
                1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
            1075                1080                1085

Phe Gly Cys Val Tyr His Gly Thr Leu Leu Asp Asn Asp Gly Lys Lys
    1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
                1125                1130                1135

Pro Asn Val Leu Ser Leu Leu Gly Ile Cys Leu Arg Ser Glu Gly Ser
            1140                1145                1150
```

```
Pro Leu Val Val Leu Pro Tyr Met Lys His Gly Asp Leu Arg Asn Phe
            1155                1160                1165

Ile Arg Asn Glu Thr His Asn Pro Thr Val Lys Asp Leu Ile Gly Phe
    1170                1175                1180

Gly Leu Gln Val Ala Lys Gly Met Lys Tyr Leu Ala Ser Lys Lys Phe
1185                1190                1195                1200

Val His Arg Asp Leu Ala Ala Arg Asn Cys Met Leu Asp Glu Lys Phe
                1205                1210                1215

Thr Val Lys Val Ala Asp Phe Gly Leu Ala Arg Asp Met Tyr Asp Lys
            1220                1225                1230

Glu Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys Ser
    1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
                1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
        1315                1320                1325

Ser Phe Ser Glu Leu Val Ser Arg Ile Ser Ala Ile Phe Ser Thr Phe
    1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
                1365                1370                1375

Asp Glu Val Asp Thr Arg Pro Ala Ser Phe Trp Glu Thr Ser
            1380                1385                1390

<210> SEQ ID NO 128
<211> LENGTH: 1381
<212> TYPE: PRT
<213> ORGANISM: Artificial Sequence
<220> FEATURE:
<223> OTHER INFORMATION: Synthetic monkey c-Met (NP_001162100)

<400> SEQUENCE: 128

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Ala Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125
```

```
Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255

Asn Phe Ile Tyr Phe Leu Thr Val Gln Arg Glu Thr Leu Asn Ala Gln
            260                 265                 270

Thr Phe His Thr Arg Ile Ile Arg Phe Cys Ser Leu Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Ala Glu Phe Thr Thr Ala Leu Gln Arg Val Asp Leu Phe Met Gly
            420                 425                 430

Gln Phe Ser Glu Val Leu Leu Thr Ser Ile Ser Thr Phe Val Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Pro Ser Gly Thr Trp Thr Gln Gln Ile
```

-continued

```
          545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu His
                755                 760                 765

Ser Val Ser Val Pro Arg Met Val Ile Asn Val His Glu Ala Gly Arg
                770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Ile Ala
                930                 935                 940

Leu Leu Leu Leu Leu Gly Leu Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975
```

```
Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln Val
        1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
            1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
            1075                1080                1085

Phe Gly Cys Val Tyr His Gly Thr Leu Leu Asp Asn Asp Gly Lys Lys
            1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
            1125                1130                1135

Pro Asn Val Leu Ser Leu Leu Gly Ile Cys Leu Arg Ser Glu Gly Ser
            1140                1145                1150

Pro Leu Val Val Leu Pro Tyr Met Lys His Gly Asp Leu Arg Asn Phe
            1155                1160                1165

Ile Arg Asn Glu Thr His Asn Pro Thr Val Lys Asp Leu Ile Gly Phe
            1170                1175                1180

Gly Leu Gln Val Ala Lys Gly Met Lys Tyr Leu Ala Ser Lys Lys Phe
1185                1190                1195                1200

Val His Arg Asp Leu Ala Ala Arg Asn Cys Met Leu Asp Glu Lys Phe
            1205                1210                1215

Thr Val Lys Val Ala Asp Phe Gly Leu Ala Arg Asp Met Tyr Asp Lys
            1220                1225                1230

Glu Tyr Tyr Ser Val His Asn Lys Thr Gly Ala Lys Leu Pro Val Lys
            1235                1240                1245

Trp Met Ala Leu Glu Ser Leu Gln Thr Gln Lys Phe Thr Thr Lys Ser
            1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
            1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
            1315                1320                1325

Ser Phe Ser Glu Leu Val Ser Arg Ile Ser Ala Ile Phe Ser Thr Phe
            1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
            1365                1370                1375

Asp Glu Val Asp Thr
            1380
```

-continued

```
<210> SEQ ID NO 129
<211> LENGTH: 1379
<212> TYPE: PRT
<213> ORGANISM: Artificial Sequence
<220> FEATURE:
<223> OTHER INFORMATION: Synthetic mouse c-Met (NP_032617.2)

<400> SEQUENCE: 129

Met Lys Ala Pro Thr Val Leu Ala Pro Gly Ile Leu Val Leu Leu Leu
  1               5                  10                  15

Ser Leu Val Gln Arg Ser His Gly Glu Cys Lys Glu Ala Leu Val Lys
             20                  25                  30

Ser Glu Met Asn Val Asn Met Lys Tyr Gln Leu Pro Asn Phe Thr Ala
         35                  40                  45

Glu Thr Pro Ile Gln Asn Val Val Leu His Gly His His Ile Tyr Leu
     50                  55                  60

Gly Ala Thr Asn Tyr Ile Tyr Val Leu Asn Asp Lys Asp Leu Gln Lys
 65                  70                  75                  80

Val Ser Glu Phe Lys Thr Gly Pro Val Leu Glu His Pro Asp Cys Leu
                 85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ser Ala Asp Ile Gln Ser Glu Val His Cys
145                 150                 155                 160

Met Phe Ser Pro Glu Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205

Ser Leu His Ser Ile Ser Val Arg Arg Leu Lys Glu Thr Gln Asp Gly
    210                 215                 220

Phe Lys Phe Leu Thr Asp Gln Ser Tyr Ile Asp Val Leu Pro Glu Phe
225                 230                 235                 240

Gln Asp Ser Tyr Pro Ile Lys Tyr Ile His Ala Phe Glu Ser Asn His
                245                 250                 255

Phe Ile Tyr Phe Leu Thr Val Gln Lys Glu Thr Leu Asp Ala Gln Thr
            260                 265                 270

Phe His Thr Arg Ile Ile Arg Phe Cys Ser Val Asp Ser Gly Leu His
        275                 280                 285

Ser Tyr Met Glu Met Pro Leu Glu Cys Ile Leu Thr Glu Lys Arg Arg
    290                 295                 300

Lys Arg Ser Thr Arg Glu Glu Val Phe Asn Ile Leu Gln Ala Ala Tyr
305                 310                 315                 320

Val Ser Lys Pro Gly Ala Asn Leu Ala Lys Gln Ile Gly Ala Ser Pro
                325                 330                 335

Ser Asp Asp Ile Leu Phe Gly Val Phe Ala Gln Ser Lys Pro Asp Ser
            340                 345                 350

Ala Glu Pro Val Asn Arg Ser Ala Val Cys Ala Phe Pro Ile Lys Tyr
        355                 360                 365
```

-continued

```
Val Asn Asp Phe Phe Asn Lys Ile Val Asn Lys Asn Asn Val Arg Cys
370                 375                 380

Leu Gln His Phe Tyr Gly Pro Asn His Glu His Cys Phe Asn Arg Thr
385                 390                 395                 400

Leu Leu Arg Asn Ser Ser Gly Cys Glu Ala Arg Ser Asp Glu Tyr Arg
            405                 410                 415

Thr Glu Phe Thr Thr Ala Leu Gln Arg Val Asp Leu Phe Met Gly Arg
            420                 425                 430

Leu Asn Gln Val Leu Leu Thr Ser Ile Ser Thr Phe Ile Lys Gly Asp
            435                 440                 445

Leu Thr Ile Ala Asn Leu Gly Thr Ser Glu Gly Arg Phe Met Gln Val
450                 455                 460

Val Leu Ser Arg Thr Ala His Leu Thr Pro His Val Asn Phe Leu Leu
465                 470                 475                 480

Asp Ser His Pro Val Ser Pro Glu Val Ile Val Glu His Pro Ser Asn
            485                 490                 495

Gln Asn Gly Tyr Thr Leu Val Val Thr Gly Lys Lys Ile Thr Lys Ile
            500                 505                 510

Pro Leu Asn Gly Leu Gly Cys Gly His Phe Gln Ser Cys Ser Gln Cys
            515                 520                 525

Leu Ser Ala Pro Tyr Phe Ile Gln Cys Gly Trp Cys His Asn Gln Cys
530                 535                 540

Val Arg Phe Asp Glu Cys Pro Ser Gly Thr Trp Thr Gln Glu Ile Cys
545                 550                 555                 560

Leu Pro Ala Val Tyr Lys Val Phe Pro Thr Ser Ala Pro Leu Glu Gly
            565                 570                 575

Gly Thr Val Leu Thr Ile Cys Gly Trp Asp Phe Gly Phe Arg Lys Asn
            580                 585                 590

Asn Lys Phe Asp Leu Arg Lys Thr Lys Val Leu Leu Gly Asn Glu Ser
            595                 600                 605

Cys Thr Leu Thr Leu Ser Glu Ser Thr Thr Asn Thr Leu Lys Cys Thr
610                 615                 620

Val Gly Pro Ala Met Ser Glu His Phe Asn Val Ser Val Ile Ile Ser
625                 630                 635                 640

Asn Ser Arg Glu Thr Thr Gln Tyr Ser Ala Phe Ser Tyr Val Asp Pro
            645                 650                 655

Val Ile Thr Ser Ile Ser Pro Arg Tyr Gly Pro Gln Ala Gly Gly Thr
            660                 665                 670

Leu Leu Thr Leu Thr Gly Lys Tyr Leu Asn Ser Gly Asn Ser Arg His
            675                 680                 685

Ile Ser Ile Gly Gly Lys Thr Cys Thr Leu Lys Ser Val Ser Asp Ser
690                 695                 700

Ile Leu Glu Cys Tyr Thr Pro Ala Gln Thr Thr Ser Asp Glu Phe Pro
705                 710                 715                 720

Val Lys Leu Lys Ile Asp Leu Ala Asn Arg Glu Thr Ser Ser Phe Ser
            725                 730                 735

Tyr Arg Glu Asp Pro Val Val Tyr Glu Ile His Pro Thr Lys Ser Phe
            740                 745                 750

Ile Ser Gly Gly Ser Thr Ile Thr Gly Ile Gly Lys Thr Leu Asn Ser
            755                 760                 765

Val Ser Leu Pro Lys Leu Val Ile Asp Val His Glu Val Gly Val Asn
770                 775                 780

Tyr Thr Val Ala Cys Gln His Arg Ser Asn Ser Glu Ile Ile Cys Cys
```

-continued

```
            785                 790                 795                 800
Thr Thr Pro Ser Leu Lys Gln Leu Gly Leu Gln Leu Pro Leu Lys Thr
                805                 810                 815
Lys Ala Phe Phe Leu Leu Asp Gly Ile Leu Ser Lys His Phe Asp Leu
                820                 825                 830
Thr Tyr Val His Asn Pro Val Phe Glu Pro Phe Glu Lys Pro Val Met
                835                 840                 845
Ile Ser Ile Gly Asn Glu Asn Val Val Glu Ile Lys Gly Asn Asn Ile
            850                 855                 860
Asp Pro Glu Ala Val Lys Gly Glu Val Leu Lys Val Gly Asn Gln Ser
865                 870                 875                 880
Cys Glu Ser Leu His Trp His Ser Gly Ala Val Leu Cys Thr Val Pro
                885                 890                 895
Ser Asp Leu Leu Lys Leu Asn Ser Glu Leu Asn Ile Glu Trp Lys Gln
                900                 905                 910
Ala Val Ser Ser Thr Val Leu Gly Lys Val Ile Val Gln Pro Asp Gln
                915                 920                 925
Asn Phe Ala Gly Leu Ile Ile Gly Ala Val Ser Ile Ser Val Val Val
            930                 935                 940
Leu Leu Leu Ser Gly Leu Phe Leu Trp Met Arg Lys Arg Lys His Lys
945                 950                 955                 960
Asp Leu Gly Ser Glu Leu Val Arg Tyr Asp Ala Arg Val His Thr Pro
                965                 970                 975
His Leu Asp Arg Leu Val Ser Ala Arg Ser Val Ser Pro Thr Thr Glu
                980                 985                 990
Met Val Ser Asn Glu Ser Val Asp Tyr Arg Ala Thr Phe Pro Glu Asp
                995                 1000                1005
Gln Phe Pro Asn Ser Ser Gln Asn Gly Ala Cys Arg Gln Val Gln Tyr
            1010                1015                1020
Pro Leu Thr Asp Leu Ser Pro Ile Leu Thr Ser Gly Asp Ser Asp Ile
1025                1030                1035                1040
Ser Ser Pro Leu Leu Gln Asn Thr Val His Ile Asp Leu Ser Ala Leu
                1045                1050                1055
Asn Pro Glu Leu Val Gln Ala Val Gln His Val Val Ile Gly Pro Ser
                1060                1065                1070
Ser Leu Ile Val His Phe Asn Glu Val Ile Gly Arg Gly His Phe Gly
                1075                1080                1085
Cys Val Tyr His Gly Thr Leu Leu Asp Asn Asp Gly Lys Lys Ile His
            1090                1095                1100
Cys Ala Val Lys Ser Leu Asn Arg Ile Thr Asp Ile Glu Glu Val Ser
1105                1110                1115                1120
Gln Phe Leu Thr Glu Gly Ile Ile Met Lys Asp Phe Ser His Pro Asn
                1125                1130                1135
Val Leu Ser Leu Leu Gly Ile Cys Leu Arg Ser Glu Gly Ser Pro Leu
                1140                1145                1150
Val Val Leu Pro Tyr Met Lys His Gly Asp Leu Arg Asn Phe Ile Arg
                1155                1160                1165
Asn Glu Thr His Asn Pro Thr Val Lys Asp Leu Ile Gly Phe Gly Leu
            1170                1175                1180
Gln Val Ala Lys Gly Met Lys Tyr Leu Ala Ser Lys Lys Phe Val His
1185                1190                1195                1200
Arg Asp Leu Ala Ala Arg Asn Cys Met Leu Asp Glu Lys Phe Thr Val
                1205                1210                1215
```

-continued

```
Lys Val Ala Asp Phe Gly Leu Ala Arg Asp Met Tyr Asp Lys Glu Tyr
         1220                1225                1230

Tyr Ser Val His Asn Lys Thr Gly Ala Lys Leu Pro Val Lys Trp Met
         1235                1240                1245

Ala Leu Glu Ser Leu Gln Thr Gln Lys Phe Thr Thr Lys Ser Asp Val
    1250                1255                1260

Trp Ser Phe Gly Val Leu Leu Trp Glu Leu Met Thr Arg Gly Ala Pro
1265                1270                1275                1280

Pro Tyr Pro Asp Val Asn Thr Phe Asp Ile Thr Ile Tyr Leu Leu Gln
             1285                1290                1295

Gly Arg Arg Leu Leu Gln Pro Glu Tyr Cys Pro Asp Ala Leu Tyr Glu
         1300                1305                1310

Val Met Leu Lys Cys Trp His Pro Lys Ala Glu Met Arg Pro Ser Phe
    1315                1320                1325

Ser Glu Leu Val Ser Arg Ile Ser Ser Ile Phe Ser Thr Phe Ile Gly
1330                1335                1340

Glu His Tyr Val His Val Asn Ala Thr Tyr Val Asn Val Lys Cys Val
1345                1350                1355                1360

Ala Pro Tyr Pro Ser Leu Leu Pro Ser Gln Asp Asn Ile Asp Gly Glu
             1365                1370                1375

Gly Asn Thr

<210> SEQ ID NO 130
<211> LENGTH: 1382
<212> TYPE: PRT
<213> ORGANISM: Artificial Sequence
<220> FEATURE:
<223> OTHER INFORMATION: Synthetic rat c-Met (NP_113705.1)

<400> SEQUENCE: 130

Met Lys Ala Pro Thr Ala Leu Ala Pro Gly Ile Leu Leu Leu Leu Leu
1               5                   10                  15

Thr Leu Ala Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Val Leu His Gly His His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Val Glu His Pro Asp Cys Phe
                85                  90                  95

Pro Cys Gln Asp Cys Ser Ser Lys Ala Asn Val Ser Gly Gly Val Trp
            100                 105                 110

Lys Asp Asn Val Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ala Ala Asp Ile Gln Ser Glu Val His Cys
145                 150                 155                 160

Met Phe Ser Pro Leu Ala Glu Glu Ser Gly Gln Cys Pro Asp Cys
                165                 170                 175

Val Val Ser Ala Leu Gly Ala Lys Val Leu Leu Ser Glu Lys Asp Arg
            180                 185                 190
```

```
Phe Ile Asn Phe Phe Val Gly Asn Thr Ile Asn Ser Ser Tyr Pro Pro
            195                 200                 205

Asp Tyr Ser Leu His Ser Ile Ser Val Arg Arg Leu Lys Glu Thr Gln
    210                 215                 220

Asp Gly Phe Lys Phe Leu Thr Asp Gln Ser Tyr Ile Asp Val Leu Gly
225                 230                 235                 240

Glu Phe Arg Asp Ser Tyr Pro Ile Lys Tyr Ile His Ala Phe Glu Ser
                245                 250                 255

Asn His Phe Ile Tyr Phe Leu Thr Val Gln Lys Glu Thr Leu Asp Ala
            260                 265                 270

Gln Thr Phe His Thr Arg Ile Ile Arg Phe Cys Ser Val Asp Ser Gly
        275                 280                 285

Leu His Ser Tyr Met Glu Met Pro Leu Glu Cys Ile Leu Thr Glu Lys
    290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala Asn Leu Ala Lys Gln Ile Gly Ala
                325                 330                 335

Ser Pro Tyr Asp Asp Ile Leu Tyr Gly Val Phe Ala Gln Ser Lys Pro
            340                 345                 350

Asp Ser Ala Glu Pro Met Asn Arg Ser Ala Val Cys Ala Phe Pro Ile
        355                 360                 365

Lys Tyr Val Asn Asp Phe Phe Asn Lys Ile Val Asn Lys Asn Asn Val
    370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Val Arg Ser Asp Glu
                405                 410                 415

Tyr Arg Thr Glu Phe Thr Thr Ala Leu Gln Ala Val Asp Leu Phe Met
            420                 425                 430

Gly Arg Leu Asn His Val Leu Leu Thr Ser Ile Ser Thr Phe Ile Lys
        435                 440                 445

Gly Asp Leu Thr Ile Ala Asn Leu Gly Thr Ser Glu Gly Arg Phe Met
    450                 455                 460

Gln Val Val Leu Ser Arg Thr Ala His Phe Thr Pro His Val Asn Phe
465                 470                 475                 480

Leu Leu Asp Ser His Pro Val Ser Pro Glu Val Ile Val Glu His Pro
                485                 490                 495

Ser Asn Gln Asn Gly Tyr Thr Leu Val Val Thr Gly Lys Lys Ile Thr
            500                 505                 510

Lys Ile Pro Leu Asn Gly Leu Gly Cys Gly His Phe Gln Ser Cys Ser
        515                 520                 525

Gln Cys Leu Ser Ala Pro Tyr Phe Ile Gln Cys Gly Trp Cys His Asn
    530                 535                 540

Arg Cys Val His Ser Asn Glu Cys Pro Ser Gly Thr Trp Thr Gln Glu
545                 550                 555                 560

Ile Cys Leu Pro Ala Val Tyr Lys Val Phe Pro Thr Ser Ala Pro Leu
                565                 570                 575

Glu Gly Gly Thr Met Leu Thr Ile Cys Gly Trp Asp Phe Gly Phe Lys
            580                 585                 590

Lys Asn Asn Lys Phe Asp Leu Arg Lys Thr Lys Val Leu Leu Gly Asn
        595                 600                 605

Glu Ser Cys Thr Leu Thr Leu Ser Glu Ser Thr Thr Asn Thr Leu Lys
```

-continued

```
            610                 615                 620
Cys Thr Val Gly Pro Ala Met Ser Glu His Phe Asn Val Ser Val Ile
625                 630                 635                 640

Val Ser Asn Ser Arg Glu Thr Thr Gln Tyr Ser Ala Phe Ser Tyr Val
                645                 650                 655

Asp Pro Val Ile Thr Ser Ile Ser Pro Arg Tyr Gly Pro His Ala Gly
                660                 665                 670

Gly Thr Leu Leu Thr Leu Thr Gly Lys Tyr Leu Asn Ser Gly Asn Ser
                675                 680                 685

Arg His Ile Ser Ile Gly Gly Lys Thr Cys Thr Leu Lys Ser Val Ser
                690                 695                 700

Asp Ser Ile Leu Glu Cys Tyr Thr Pro Gly His Thr Val Ser Ala Glu
705                 710                 715                 720

Phe Pro Val Lys Leu Lys Ile Asp Leu Ala Asp Arg Val Thr Ser Ser
                725                 730                 735

Phe Ser Tyr Gly Glu Asp Pro Phe Val Ser Glu Ile His Pro Thr Lys
                740                 745                 750

Ser Phe Ile Ser Gly Gly Ser Thr Ile Thr Gly Ile Gly Lys Asn Leu
                755                 760                 765

Asn Ser Val Ser Thr Pro Lys Leu Val Ile Glu Val His Asp Val Gly
                770                 775                 780

Val Asn Tyr Thr Val Ala Cys Gln His Arg Ser Ser Glu Ile Ile
785                 790                 795                 800

Cys Cys Thr Thr Pro Ser Leu Gln Gln Leu Asp Leu Gln Leu Pro Leu
                805                 810                 815

Lys Thr Lys Ala Phe Phe Leu Leu Asp Gly Ile Leu Ser Lys His Phe
                820                 825                 830

Asp Leu Thr Tyr Val His Asp Pro Met Phe Lys Pro Phe Glu Lys Pro
                835                 840                 845

Val Met Ile Ser Met Gly Asn Glu Asn Val Val Glu Ile Lys Gly Asp
                850                 855                 860

Asp Ile Asp Pro Glu Ala Val Lys Gly Glu Val Leu Lys Val Gly Asn
865                 870                 875                 880

Lys Ser Cys Glu Asn Leu His Trp His Ser Glu Ala Leu Leu Cys Thr
                885                 890                 895

Val Pro Ser Asp Leu Leu Lys Leu Asn Gly Gly Glu Leu Asn Ile Glu
                900                 905                 910

Trp Lys Gln Ala Val Ser Ser Thr Val Leu Gly Lys Val Ile Val Gln
                915                 920                 925

Pro Asp Gln Asn Phe Ala Gly Leu Ile Ile Gly Ala Val Ser Ile Ser
                930                 935                 940

Val Val Val Leu Leu Val Ser Gly Leu Phe Leu Trp Leu Arg Lys Arg
945                 950                 955                 960

Lys His Lys Asp Leu Gly Ser Glu Leu Val Arg Tyr Asp Ala Arg Val
                965                 970                 975

His Thr Pro His Leu Asp Arg Leu Val Ser Ala Arg Ser Val Ser Pro
                980                 985                 990

Thr Thr Glu Met Val Ser Asn Glu Ser Val Asp Tyr Arg Ala Thr Phe
                995                 1000                1005

Pro Glu Asp Gln Phe Pro Asn Ser Ser Gln Asn Gly Ala Cys Arg Gln
                1010                1015                1020

Val Gln Tyr Pro Leu Thr Asp Leu Ser Pro Ile Leu Thr Ser Gly Asp
1025                1030                1035                1040
```

-continued

Ser Asp Ile Ser Ser Pro Leu Leu Gln Asn Thr Val His Ile Asp Leu
            1045                1050                1055

Ser Ala Leu Asn Pro Glu Leu Val Gln Ala Val Gln His Val Val Ile
            1060                1065                1070

Gly Pro Ser Ser Leu Ile Val His Phe Asn Glu Val Ile Gly Arg Gly
            1075                1080                1085

His Phe Gly Cys Val Tyr His Gly Thr Leu Leu Asp Ser Asp Gly Lys
        1090                1095                1100

Lys Ile His Cys Ala Val Lys Ser Leu Asn Arg Ile Thr Asp Ile Glu
1105                1110                1115                1120

Glu Val Ser Gln Phe Leu Thr Glu Gly Ile Ile Met Lys Asp Phe Ser
            1125                1130                1135

His Pro Asn Val Leu Ser Leu Leu Gly Ile Cys Leu Arg Ser Glu Gly
            1140                1145                1150

Ser Pro Leu Val Val Leu Pro Tyr Met Lys His Gly Asp Leu Arg Asn
            1155                1160                1165

Phe Ile Arg Asn Glu Thr His Asn Pro Thr Val Lys Asp Leu Ile Gly
            1170                1175                1180

Phe Gly Leu Gln Val Ala Lys Gly Met Lys Tyr Leu Ala Ser Lys Lys
1185                1190                1195                1200

Phe Val His Arg Asp Leu Ala Ala Arg Asn Cys Met Leu Asp Glu Lys
            1205                1210                1215

Phe Thr Val Lys Val Ala Asp Phe Gly Leu Ala Arg Asp Met Tyr Asp
            1220                1225                1230

Lys Glu Tyr Tyr Ser Val His Asn Lys Thr Gly Ala Lys Leu Pro Val
            1235                1240                1245

Lys Trp Met Ala Leu Glu Ser Leu Gln Thr Gln Lys Phe Thr Thr Lys
            1250                1255                1260

Ser Asp Val Trp Ser Phe Gly Val Leu Leu Trp Glu Leu Met Thr Arg
1265                1270                1275                1280

Gly Ala Pro Pro Tyr Pro Asp Val Asn Thr Phe Asp Ile Thr Ile Tyr
            1285                1290                1295

Leu Leu Gln Gly Arg Arg Leu Leu Gln Pro Glu Tyr Cys Pro Asp Ala
            1300                1305                1310

Leu Tyr Glu Val Met Leu Lys Cys Trp His Pro Lys Ala Glu Met Arg
            1315                1320                1325

Pro Ser Phe Ser Glu Leu Val Ser Arg Ile Ser Ser Ile Phe Ser Thr
            1330                1335                1340

Phe Ile Gly Glu His Tyr Val His Val Asn Ala Thr Tyr Val Asn Val
1345                1350                1355                1360

Lys Cys Val Ala Pro Tyr Pro Ser Leu Leu Pro Ser Gln Asp Asn Ile
            1365                1370                1375

Asp Gly Glu Ala Asn Thr
        1380

<210> SEQ ID NO 131
<211> LENGTH: 6641
<212> TYPE: DNA
<213> ORGANISM: Artificial Sequence
<220> FEATURE:
<223> OTHER INFORMATION: Synthetic gene encoding NP_000236
<220> FEATURE:
<221> NAME/KEY: misc_feature
<222> LOCATION: (188)..(4360)
<223> OTHER INFORMATION: CDS

<400> SEQUENCE: 131

```
gccctcgccg cccgcggcgc cccgagcgct ttgtgagcag atgcggagcc gagtggaggg      60
cgcgagccag atgcggggcg acagctgact tgctgagagg aggcggggag gcgcggagcg     120
cgcgtgtggt ccttgcgccg ctgacttctc cactggttcc tgggcaccga aagataaacc     180
tctcataatg aaggcccccg ctgtgcttgc acctggcatc ctcgtgctcc tgtttacctt     240
ggtgcagagg agcaatgggg agtgtaaaga ggcactagca aagtccgaga tgaatgtgaa     300
tatgaagtat cagcttccca acttcaccgc ggaaacaccc atccagaatg tcattctaca     360
tgagcatcac attttccttg gtgccactaa ctacatttat gttttaaatg aggaagacct     420
tcagaaggtt gctgagtaca agactgggcc tgtgctggaa cacccagatt gtttcccatg     480
tcaggactgc agcagcaaag ccaatttatc aggaggtgtt tggaaagata acatcaacat     540
ggctctagtt gtcgacacct actatgatga tcaactcatt agctgtggca gcgtcaacag     600
agggacctgc cagcgacatg tctttcccca caatcatact gctgacatac agtcggaggt     660
tcactgcata ttctcccccac agatagaaga gcccagccag tgtcctgact gtgtggtgag     720
cgccctggga gccaaagtcc tttcatctgt aaaggaccgg ttcatcaact tctttgtagg     780
caataccata aattcttctt atttcccaga tcatccattg cattcgatat cagtgagaag     840
gctaaaggaa acgaaagatg gttttatgtt tttgacggac cagtcctaca ttgatgtttt     900
acctgagttc agagattctt accccattaa gtatgtccat gcctttgaaa gcaacaattt     960
tatttacttc ttgacggtcc aaagggaaac tctagatgct cagacttttc acacaagaat    1020
aatcaggttc tgttccataa actctggatt gcattcctac atggaaatgc ctctggagtg    1080
tattctcaca gaaaagagaa aaaagagatc cacaaagaag gaagtgttta atatacttca    1140
ggctgcgtat gtcagcaagc ctggggccca gcttgctaga caaataggag ccagcctgaa    1200
tgatgacatt cttttcgggg tgttcgcaca aagcaagcca gattctgccg aaccaatgga    1260
tcgatctgcc atgtgtgcat tccctatcaa atatgtcaac gacttcttca acaagatcgt    1320
caacaaaaac aatgtgagat gtctccagca tttttacgga cccaatcatg agcactgctt    1380
taataggaca cttctgagaa attcatcagg ctgtgaagcg cgccgtgatg aatatcgaac    1440
agagtttacc acagctttgc agcgcgttga cttattcatg ggtcaattca gcgaagtcct    1500
cttaacatct atatccacct tcattaaagg agacctcacc atagctaatc ttgggacatc    1560
agagggtcgc ttcatgcagg ttgtggtttc tcgatcagga ccatcaaccc ctcatgtgaa    1620
ttttctcctg gactcccatc cagtgtctcc agaagtgatt gtggagcata cattaaacca    1680
aaatggctac acactggtta tcactgggaa gaagatcacg aagatcccat tgaatggctt    1740
gggctgcaga catttccagt cctgcagtca atgcctctct gccccaccct ttgttcagtg    1800
tggctggtgc cacgacaaat gtgtgcgatc ggaggaatgc ctgagcggga catggactca    1860
acagatctgt ctgcctgcaa tctacaaggt tttcccaaat agtgcacccc ttgaaggagg    1920
gacaaggctg accatatgtg gctgggactt tgggatttcgg aggaataata aatttgattt    1980
aaagaaaact agagttctcc ttggaaatga gagctgcacc ttgactttaa gtgagagcac    2040
gatgaataca ttgaaatgca cagttggtcc tgccatgaat aagcatttca atatgtccat    2100
aattatttca aatggccacg ggacaacaca atacagtaca ttctcctatg tggatcctgt    2160
aataacaagt atttcgccga aatacggtcc tatggctggt ggcactttac ttactttaac    2220
tggaaattac ctaaacagtg ggaattctag acacatttca attggtggaa aaacatgtac    2280
tttaaaaagt gtgtcaaaca gtattcttga atgttatacc ccagcccaaa ccatttcaac    2340
```

-continued

```
tgagtttgct gttaaattga aaattgactt agccaaccga gagacaagca tcttcagtta    2400
ccgtgaagat cccattgtct atgaaattca tccaaccaaa tctttttatta gtggtgggag   2460
cacaataaca ggtgttggga aaaacctgaa ttcagttagt gtcccgagaa tggtcataaa    2520
tgtgcatgaa gcaggaagga actttacagt ggcatgtcaa catcgctcta attcagagat    2580
aatctgttgt accactcctt ccctgcaaca gctgaatctg caactccccc tgaaaaccaa    2640
agccttttc atgttagatg ggatcctttc caaatacttt gatctcattt atgtacataa     2700
tcctgtgttt aagccttttg aaaagccagt gatgatctca atgggcaatg aaaatgtact    2760
ggaaattaag ggaaatgata ttgaccctga agcagttaaa ggtgaagtgt taaaagttgg    2820
aaataagagc tgtgagaata tacacttaca ttctgaagcc gttttatgca cggtccccaa    2880
tgacctgctg aaattgaaca gcgagctaaa tatagagtgg aagcaagcaa tttcttcaac    2940
cgtccttgga aaagtaatag ttcaaccaga tcagaatttc acaggattga ttgctggtgt    3000
tgtctcaata tcaacagcac tgttattact acttgggttt ttcctgtggc tgaaaaagag    3060
aaagcaaatt aaagatctgg gcagtgaatt agttcgctac gatgcaagag tacacactcc    3120
tcatttggat aggcttgtaa gtgcccgaag tgtaagccca actacagaaa tggtttcaaa    3180
tgaatctgta gactaccgag ctacttttcc agaagatcag tttcctaatt catctcagaa    3240
cggttcatgc cgacaagtgc agtatcctct gacagacatg tcccccatcc taactagtgg    3300
ggactctgat atatccagtc cattactgca aaatactgtc cacattgacc tcagtgctct    3360
aaatccagag ctggtccagg cagtgcagca tgtagtgatt gggcccagta gcctgattgt    3420
gcatttcaat gaagtcatag aagagggca ttttggttgt gtatatcatg ggactttgtt    3480
ggacaatgat ggcaagaaaa ttcactgtgc tgtgaaatcc ttgaacagaa tcactgacat    3540
aggagaagtt tcccaatttc tgaccgaggg aatcatcatg aaagatttta gtcatcccaa    3600
tgtcctctcg ctcctgggaa tctgcctgcg aagtgaaggg tctccgctgg tggtcctacc    3660
atacatgaaa catggagatc ttcgaaattt cattcgaaat gagactcata atccaactgt    3720
aaaagatctt attggctttg gtcttcaagt agccaaaggc atgaaatatc ttgcaagcaa    3780
aaagtttgtc cacagagact tggctgcaag aaactgtatg ctggatgaaa aattcacagt    3840
caaggttgct gattttggtc ttgccagaga catgtatgat aaagaatact atagtgtaca    3900
caacaaaaca ggtgcaaagc tgccagtgaa gtggatggct ttggaaagtc tgcaaactca    3960
aaagtttacc accaagtcag atgtgtggtc ctttggcgtg ctcctctggg agctgatgac    4020
aagaggagcc ccaccttatc ctgacgtaaa caccttttga taactgtttt acttgttgca    4080
agggagaaga ctcctacaac ccgaatactg cccagacccc ttatatgaag taatgctaaa    4140
atgctggcac cctaaagccg aaatgcgccc atccttttct gaactggtgt cccggatatc    4200
agcgatcttc tctactttca ttggggagca ctatgtccat gtgaacgcta cttatgtgaa    4260
cgtaaaatgt gtcgctccgt atccttctct gttgtcatca aagataacg ctgatgatga     4320
ggtggacaca cgaccagcct ccttctggga gacatcatag tgctagtact atgtcaaagc    4380
aacagtccac actttgtcca atggtttttt cactgcctga cctttaaaag gccatcgata    4440
ttctttgctc ttgccaaaat tgcactatta taggacttgt attgttattt aaattactgg    4500
attctaagga atttcttatc tgacagagca tcagaaccag aggcttggtc ccacaggcca    4560
cggaccaatg gcctgcagcc gtgacaacac tcctgtcata ttggagtcca aaacttgaat    4620
tctgggttga attttttaaa aatcaggtac cacttgattt catatgggaa attgaagcag    4680
```

```
gaaatattga gggcttcttg atcacagaaa actcagaaga gatagtaatg ctcaggacag    4740
gagcggcagc cccagaacag gccactcatt tagaattcta gtgtttcaaa acactttgt    4800
gtgttgtatg gtcaataaca tttttcatta ctgatggtgt cattcaccca ttaggtaaac    4860
attccctttt aaatgtttgt ttgttttttg agacaggatc tcactctgtt gccagggctg    4920
tagtgcagtg gtgtgatcat agctcactgc aacctccacc tcccaggctc aagcctcccg    4980
aatagctggg actacaggcg cacaccacca tccccggcta attttgtat tttttgtaga    5040
gacggggttt tgccatgttg ccaaggctgg tttcaaactc ctggactcaa gaatccacc    5100
cacctcagcc tcccaaagtg ctaggattac aggcatgagc cactgcgccc agcccttata    5160
aatttttgta tagacattcc tttggttgga agaatattta taggcaatac agtcaaagtt    5220
tcaaaatagc atcacacaaa acatgtttat aaatgaacag gatgtaatgt acatagatga    5280
cattaagaaa atttgtatga aataatttag tcatcatgaa atatttagtt gtcatataaa    5340
aacccactgt ttgagaatga tgctactctg atctaatgaa tgtgaacatg tagatgtttt    5400
gtgtgtattt ttttaaatga aaactcaaaa taagacaagt aatttgttga taaatatttt    5460
taaagataac tcagcatgtt tgtaaagcag gatacatttt actaaaaggt tcattggttc    5520
caatcacagc tcataggtag agcaaagaaa gggtggatgg attgaaaaga ttagcctctg    5580
tctcggtggc aggttcccac ctcgcaagca attggaaaca aaacttttgg ggagttttat    5640
tttgcattag ggtgtgtttt atgttaagca aaacatactt tagaaacaaa tgaaaaaggc    5700
aattgaaaat cccagctatt tcacctagat ggaatagcca ccctgagcag aactttgtga    5760
tgcttcattc tgtggaattt tgtgcttgct actgtatagt gcatgtggtg taggttactc    5820
taactggttt tgtcgacgta aacatttaaa gtgttatatt ttttataaaa atgtttattt    5880
ttaatgatat gagaaaaatt ttgttaggcc acaaaaacac tgcactgtga acattttaga    5940
aaaggtatgt cagactggga ttaatgacag catgattttc aatgactgta aattgcgata    6000
aggaaatgta ctgattgcca atacacccca ccctcattac atcatcagga cttgaagcca    6060
agggttaacc cagcaagcta caaagagggt gtgtcacact gaaactcaat agttgagttt    6120
ggctgttgtt gcaggaaaat gattataact aaaagctctc tgatagtgca gagacttacc    6180
agaagacaca aggaattgta ctgaagagct attacaatcc aaatattgcc gtttcataaa    6240
tgtaataagt aatactaatt cacagagtat tgtaaatggt ggatgacaaa agaaaatctg    6300
ctctgtggaa agaaagaact gtctctacca gggtcaagag catgaacgca tcaatagaaa    6360
gaactcgggg aaacatccca tcaacaggac tacacacttg tatatacatt cttgagaaca    6420
ctgcaatgtg aaaatcacgt ttgctattta taaacttgtc cttagattaa tgtgtctgga    6480
cagattgtgg gagtaagtga ttcttctaag aattagatac ttgtcactgc ctatacctgc    6540
agctgaactg aatggtactt cgtatgttaa tagttgttct gataaatcat gcaattaaag    6600
taaagtgatg caacatcttg taaaaaaaaa aaaaaaaaa a                         6641
```

<210> SEQ ID NO 132
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 132

Asp Ile Gln Met Thr Gln Ser Pro Ser Ser Leu Ser Ala Ser Val Gly
 1               5                  10                  15

```
Asp Arg Val Thr Ile Thr Cys Lys Ser Ser Gln Ser Leu Leu Ala Ser
            20              25              30

Gly Asn Gln Asn Asn Tyr Leu Ala Trp Tyr Gln Gln Lys Pro Gly Lys
        35              40              45

Ala Pro Lys Met Leu Ile Ile Trp Ala Ser Thr Arg Val Ser Gly Val
    50              55              60

Pro Ser Arg Phe Ser Gly Ser Gly Ser Gly Thr Asp Phe Thr Leu Thr
65              70              75              80

Ile Ser Ser Leu Gln Pro Glu Asp Phe Ala Thr Tyr Tyr Cys Gln Gln
                85              90              95

Ser Tyr Ser Arg Pro Tyr Thr Phe Gly Gln Gly Thr Lys Val Glu Ile
            100             105             110

Lys Arg
```